(12) United States Patent
Connor

(10) Patent No.: US 10,137,023 B2
(45) Date of Patent: Nov. 27, 2018

(54) COLONNADE (TM) EXPANDABLE INTRAGASTRIC FOOD FLOW LUMEN DEVICE

(71) Applicant: Robert A. Connor, Forest Lake, MN (US)

(72) Inventor: Robert A. Connor, Forest Lake, MN (US)

(73) Assignee: Medibotics LLC, St. Paul, MN (US)

( * ) Notice: Subject to any disclaimer, the term of this patent is extended or adjusted under 35 U.S.C. 154(b) by 378 days.

(21) Appl. No.: 14/967,309

(22) Filed: Dec. 13, 2015

(65) Prior Publication Data

US 2016/0095731 A1  Apr. 7, 2016

Related U.S. Application Data

(63) Continuation-in-part of application No. 13/616,238, filed on Sep. 14, 2012, now abandoned, and a continuation-in-part of application No. 13/797,955, filed on Mar. 12, 2013, now Pat. No. 9,456,916.

(60) Provisional application No. 62/096,199, filed on Dec. 23, 2014.

(51) Int. Cl.
*A61F 5/00* (2006.01)
*G06F 19/00* (2018.01)

(52) U.S. Cl.
CPC .......... *A61F 5/0033* (2013.01); *A61F 5/0036* (2013.01); *A61F 5/0076* (2013.01); *G06F 19/3475* (2013.01)

(58) Field of Classification Search
CPC ..... A61F 5/0033; A61F 5/0036; A61F 5/0043
USPC ............................. 604/8, 9, 103.06–103.08
See application file for complete search history.

(56) References Cited

U.S. PATENT DOCUMENTS

| | | |
|---|---|---|
| 4,416,267 A | 11/1983 | Garren et al. |
| 4,694,827 A | 9/1987 | Weiner et al. |
| 4,899,747 A | 2/1990 | Garren et al. |
| 5,234,454 A | 8/1993 | Bangs |
| 5,259,399 A | 11/1993 | Brown |
| 5,993,473 A | 11/1999 | Chan et al. |
| 6,454,785 B2 | 9/2002 | De Hoyos Garza |
| 6,579,301 B1 | 6/2003 | Bales et al. |
| 6,733,512 B2 | 5/2004 | McGhan |
| 6,981,980 B2 | 1/2006 | Sampson et al. |
| 7,056,305 B2 | 6/2006 | Garza Alvarez |
| 7,112,186 B2 | 9/2006 | Shah |
| 7,470,251 B2 | 12/2008 | Shah |
| 7,682,306 B2 | 3/2010 | Shah |
| 7,854,745 B2 | 12/2010 | Brister et al. |
| 7,947,038 B2 | 5/2011 | Edwards |
| 8,001,974 B2 | 8/2011 | Makower et al. |
| 8,066,780 B2 | 11/2011 | Chen et al. |
| 8,070,768 B2 | 12/2011 | Kim et al. |

(Continued)

*Primary Examiner* — Matthew F Desanto

(57) ABSTRACT

This invention is an expandable intragastric device for reducing food consumption and/or absorption. In an example, this device can be embodied in a plurality of longitudinal expandable members which are arranged in a colonnade configuration to form a restrictive food lumen within a stomach. Pumping a flowable substance between the interiors of these expandable members changes the rate of food flow through the stomach, the capacity of the stomach to hold food, and/or the amount of food absorbed by the body. This offers some of the beneficial effects of gastric sleeve surgery, while also being adjustable and reversible.

11 Claims, 25 Drawing Sheets

(56) References Cited

U.S. PATENT DOCUMENTS

| Patent/Publication | Date | Inventor |
|---|---|---|
| 8,100,932 B2 | 1/2012 | Nihalani |
| 8,142,469 B2 | 3/2012 | Sosnowski et al. |
| 8,162,969 B2 | 4/2012 | Brister et al. |
| 8,187,297 B2 | 5/2012 | Makower et al. |
| 8,192,455 B2 | 6/2012 | Brazzini et al. |
| 8,202,291 B1 | 6/2012 | Brister et al. |
| 8,226,602 B2 | 7/2012 | Quijana et al. |
| 8,236,023 B2 | 8/2012 | Birk et al. |
| 8,282,666 B2 | 10/2012 | Birk |
| 8,292,911 B2 | 10/2012 | Brister et al. |
| 8,343,031 B2 | 1/2013 | Gertner |
| 8,740,927 B2 | 6/2014 | Brister et al. |
| 2001/0037127 A1 | 11/2001 | De Hoyos Garza |
| 2004/0059289 A1 | 3/2004 | Garza Alvarez |
| 2004/0122526 A1* | 6/2004 | Imran ............... A61F 2/04 623/23.65 |
| 2005/0159769 A1 | 7/2005 | Alverdy |
| 2005/0267405 A1 | 12/2005 | Shah |
| 2005/0267596 A1 | 12/2005 | Chen et al. |
| 2006/0020278 A1 | 1/2006 | Burnett et al. |
| 2006/0058829 A1 | 3/2006 | Sampson et al. |
| 2007/0078476 A1 | 4/2007 | Hull et al. |
| 2007/0118168 A1 | 5/2007 | Lointier et al. |
| 2007/0149994 A1 | 6/2007 | Sosnowski et al. |
| 2007/0173881 A1 | 7/2007 | Birk et al. |
| 2007/0239284 A1 | 11/2007 | Skerven et al. |
| 2007/0265598 A1 | 11/2007 | Karasik |
| 2007/0265646 A1 | 11/2007 | McCoy et al. |
| 2007/0265709 A1* | 11/2007 | Rajan ............... A61F 2/04 623/23.64 |
| 2008/0097513 A1* | 4/2008 | Kaji ............... A61B 17/12099 606/192 |
| 2008/0147002 A1 | 6/2008 | Gertner |
| 2008/0161717 A1 | 7/2008 | Gertner |
| 2008/0188766 A1 | 8/2008 | Gertner |
| 2008/0208240 A1 | 8/2008 | Paz |
| 2008/0208241 A1 | 8/2008 | Weiner et al. |
| 2008/0243071 A1 | 10/2008 | Quijano et al. |
| 2008/0243166 A1 | 10/2008 | Paganon et al. |
| 2008/0306506 A1 | 12/2008 | Leatherman |
| 2008/0319471 A1 | 12/2008 | Sosnowski et al. |
| 2009/0048624 A1 | 2/2009 | Alverdy |
| 2009/0082644 A1 | 3/2009 | Li |
| 2009/0131968 A1 | 5/2009 | Birk |
| 2009/0171383 A1 | 7/2009 | Cole et al. |
| 2009/0187200 A1 | 7/2009 | Burnett et al. |
| 2009/0187201 A1 | 7/2009 | Burnett et al. |
| 2009/0216262 A1 | 8/2009 | Burnett et al. |
| 2009/0259236 A2 | 10/2009 | Burnett et al. |
| 2009/0275973 A1 | 11/2009 | Chen et al. |
| 2010/0049224 A1 | 2/2010 | Vargas |
| 2010/0100115 A1 | 4/2010 | Soetermans et al. |
| 2010/0100116 A1 | 4/2010 | Brister et al. |
| 2010/0100117 A1 | 4/2010 | Brister et al. |
| 2010/0130998 A1 | 5/2010 | Alverdy |
| 2010/0137897 A1 | 6/2010 | Brister et al. |
| 2010/0152764 A1 | 6/2010 | Merkle |
| 2010/0191270 A1 | 7/2010 | Garza Alvarez |
| 2010/0331617 A1 | 12/2010 | Forsell |
| 2010/0332000 A1 | 12/2010 | Forsell |
| 2011/0034760 A1 | 2/2011 | Brynelsen et al. |
| 2011/0092998 A1 | 4/2011 | Hirszowicz et al. |
| 2011/0178544 A1 | 7/2011 | Sosnowski et al. |
| 2011/0295056 A1 | 12/2011 | Aldridge et al. |
| 2011/0295057 A1 | 12/2011 | Aldridge et al. |
| 2011/0319924 A1 | 12/2011 | Cole et al. |
| 2012/0004676 A1 | 1/2012 | Vargas |
| 2012/0022322 A1 | 1/2012 | Pasricha |
| 2012/0053613 A1 | 3/2012 | Weitzner et al. |
| 2012/0089170 A1 | 4/2012 | Dominguez |
| 2012/0089172 A1 | 4/2012 | Babkes et al. |
| 2012/0095494 A1 | 4/2012 | Dominguez et al. |
| 2012/0095495 A1 | 4/2012 | Babkes et al. |
| 2012/0095496 A1 | 4/2012 | Dominguez et al. |
| 2012/0191123 A1 | 7/2012 | Brister et al. |
| 2012/0191124 A1 | 7/2012 | Brister et al. |
| 2012/0191125 A1 | 7/2012 | Babkes et al. |
| 2012/0191126 A1 | 7/2012 | Pecor et al. |
| 2012/0215249 A1 | 8/2012 | Brazzini et al. |
| 2012/0232361 A1 | 9/2012 | Birk |
| 2012/0232576 A1 | 9/2012 | Brister et al. |
| 2012/0232577 A1 | 9/2012 | Birk et al. |
| 2012/0245553 A1 | 9/2012 | Raven et al. |
| 2012/0253378 A1 | 10/2012 | Makower et al. |
| 2012/0265030 A1 | 10/2012 | Li |
| 2012/0265234 A1 | 10/2012 | Brister et al. |
| 2012/0283766 A1 | 11/2012 | Makower et al. |
| 2012/0289992 A1 | 11/2012 | Quijano et al. |
| 2012/0323160 A1 | 12/2012 | Babkes |
| 2013/0012980 A1 | 1/2013 | Brister et al. |
| 2013/0079603 A1 | 3/2013 | Vargas |
| 2013/0226219 A1 | 8/2013 | Brister et al. |
| 2013/0226221 A1 | 8/2013 | Hyde et al. |
| 2013/0274789 A1 | 10/2013 | Brooks et al. |
| 2014/0221899 A1 | 8/2014 | Vargas |
| 2015/0150699 A1 | 6/2015 | Pattison et al. |
| 2015/0223956 A1 | 8/2015 | Nadler et al. |

\* cited by examiner

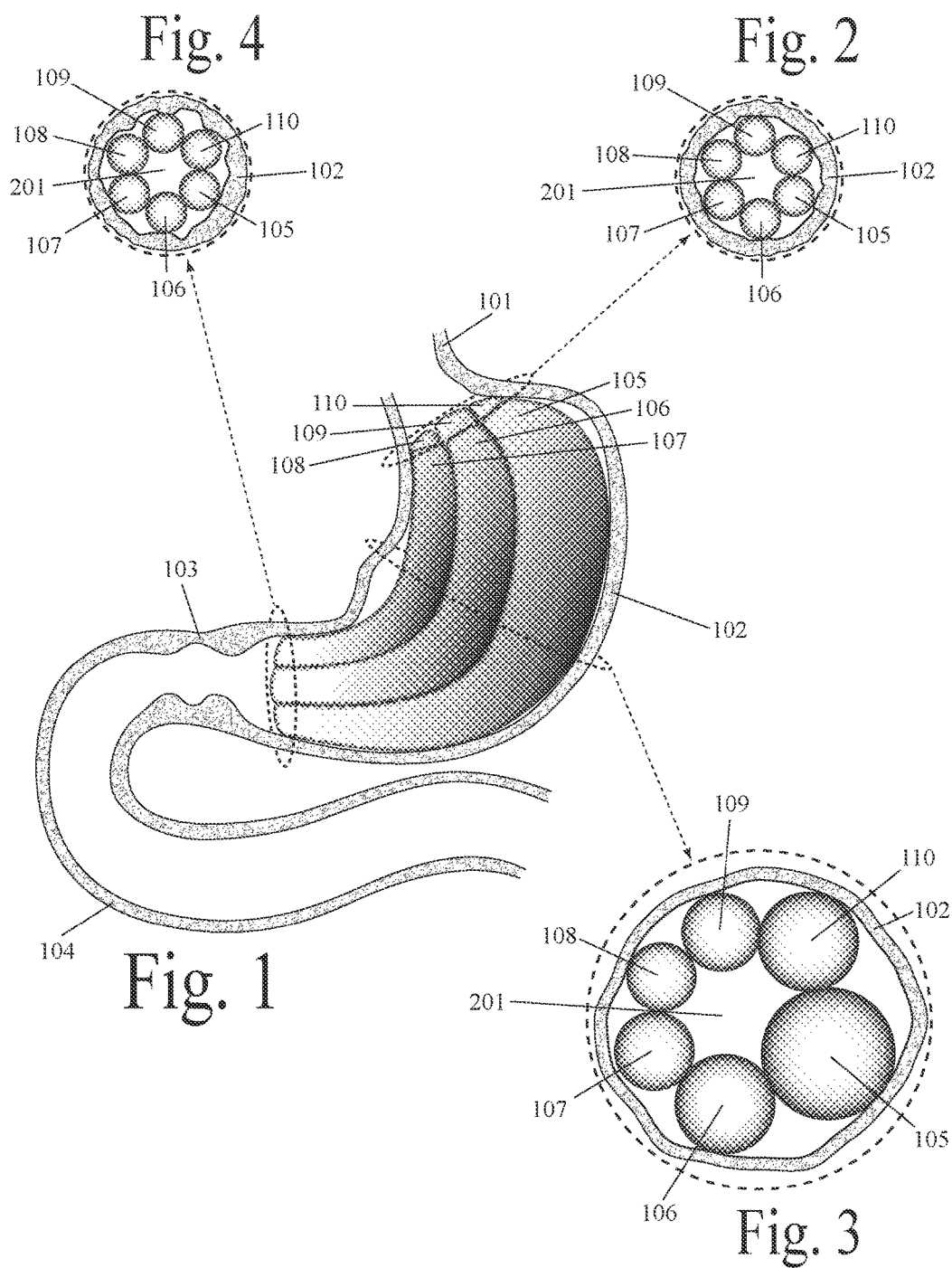

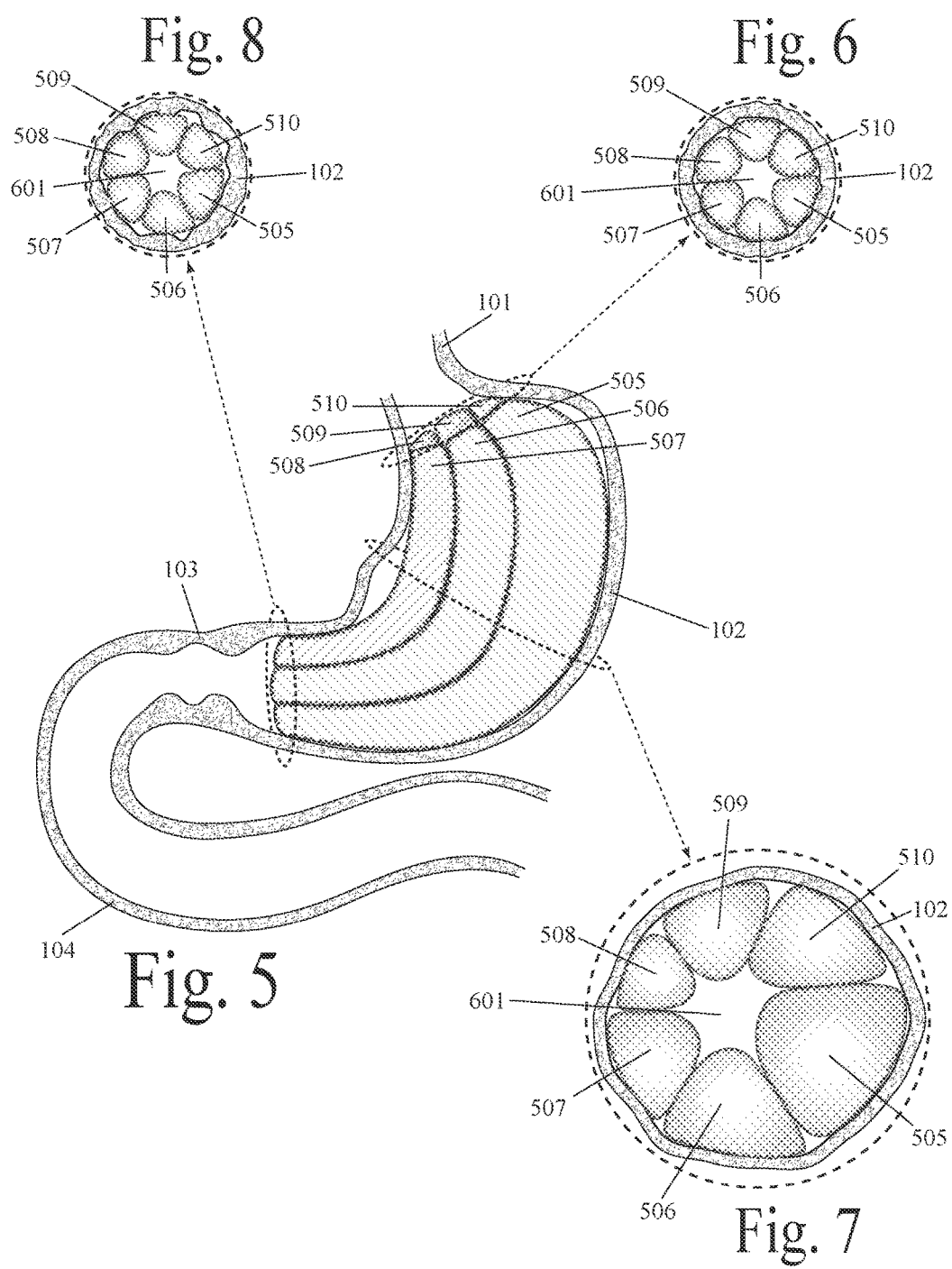

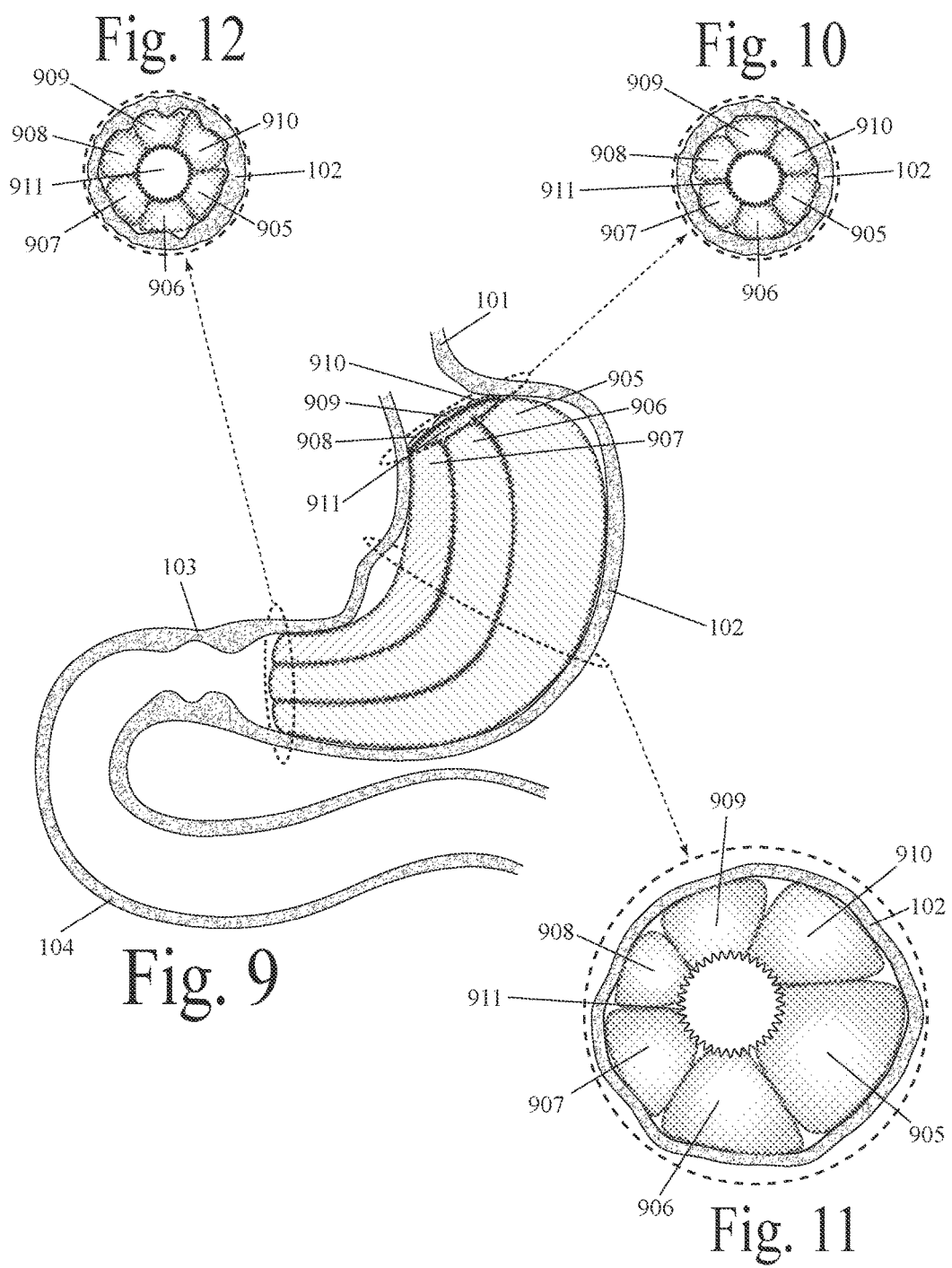

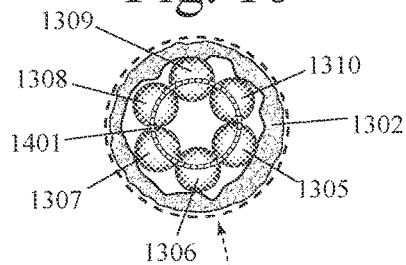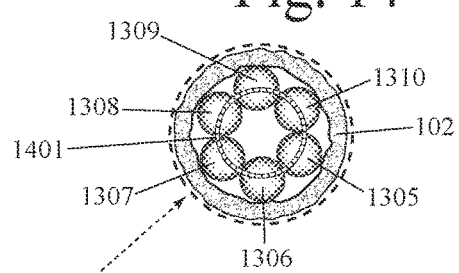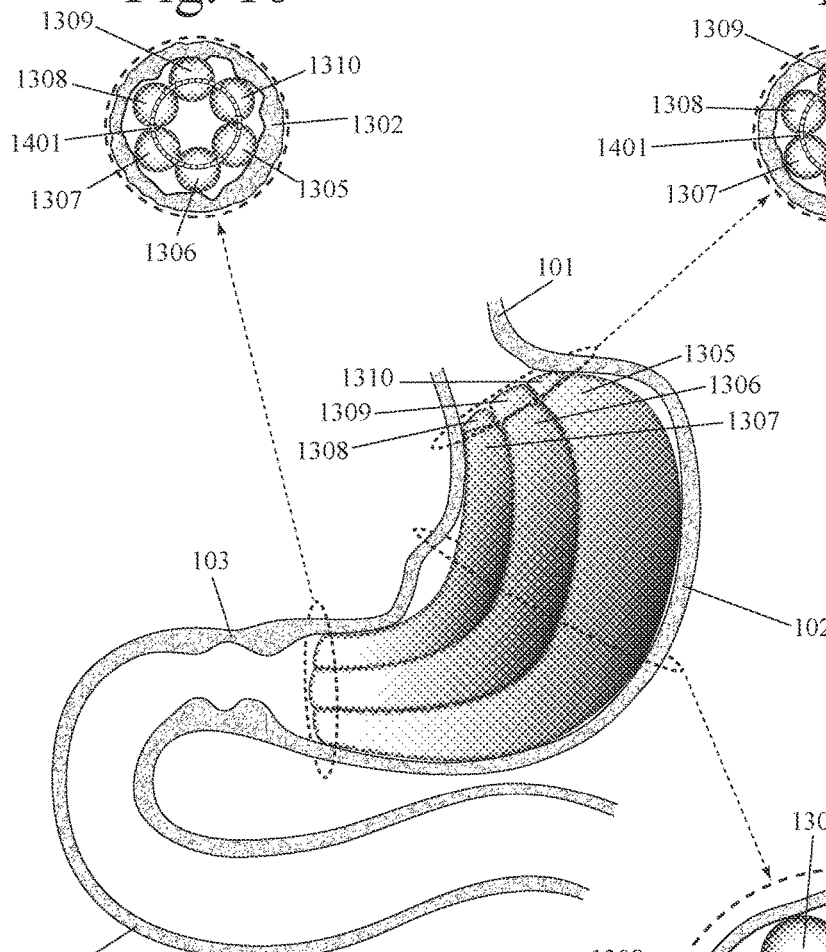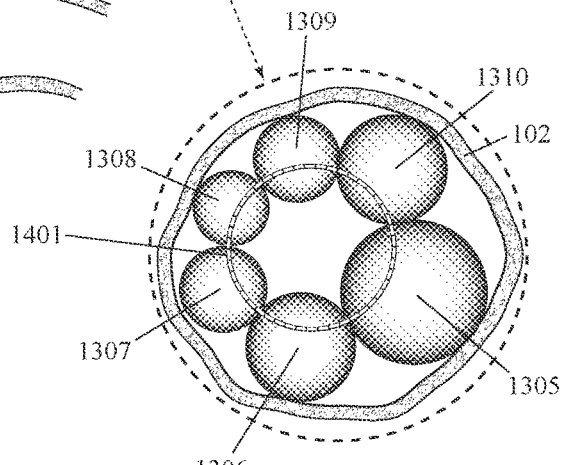

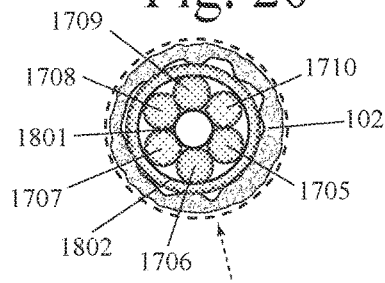
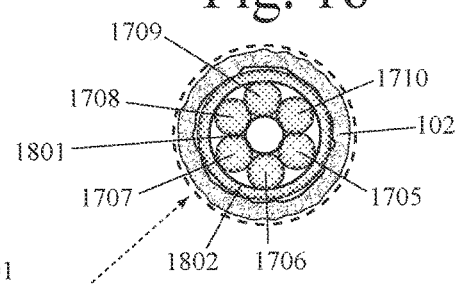
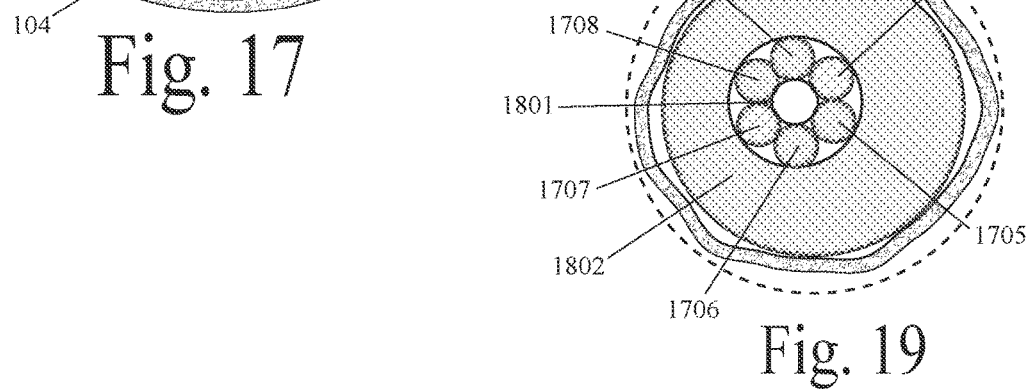

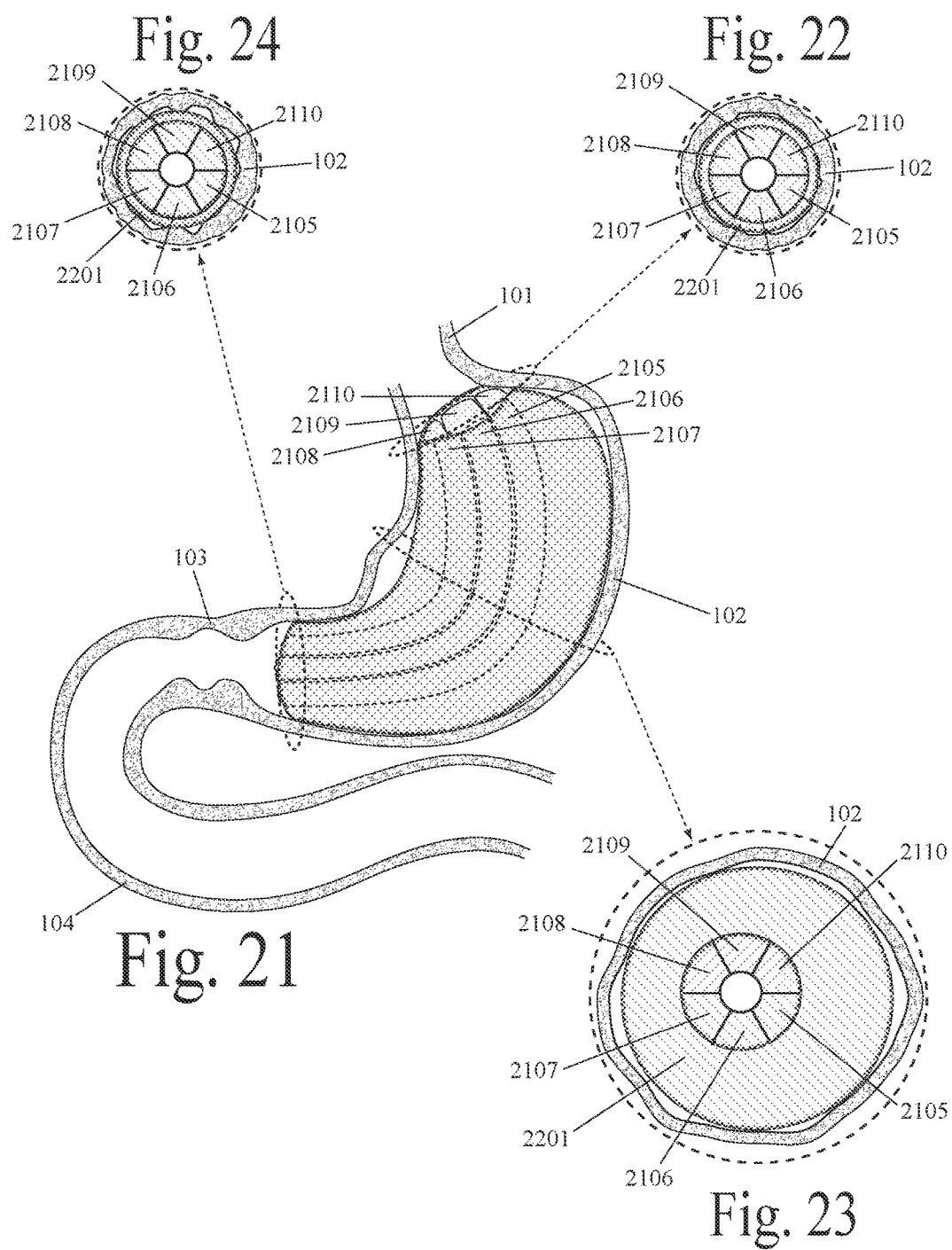

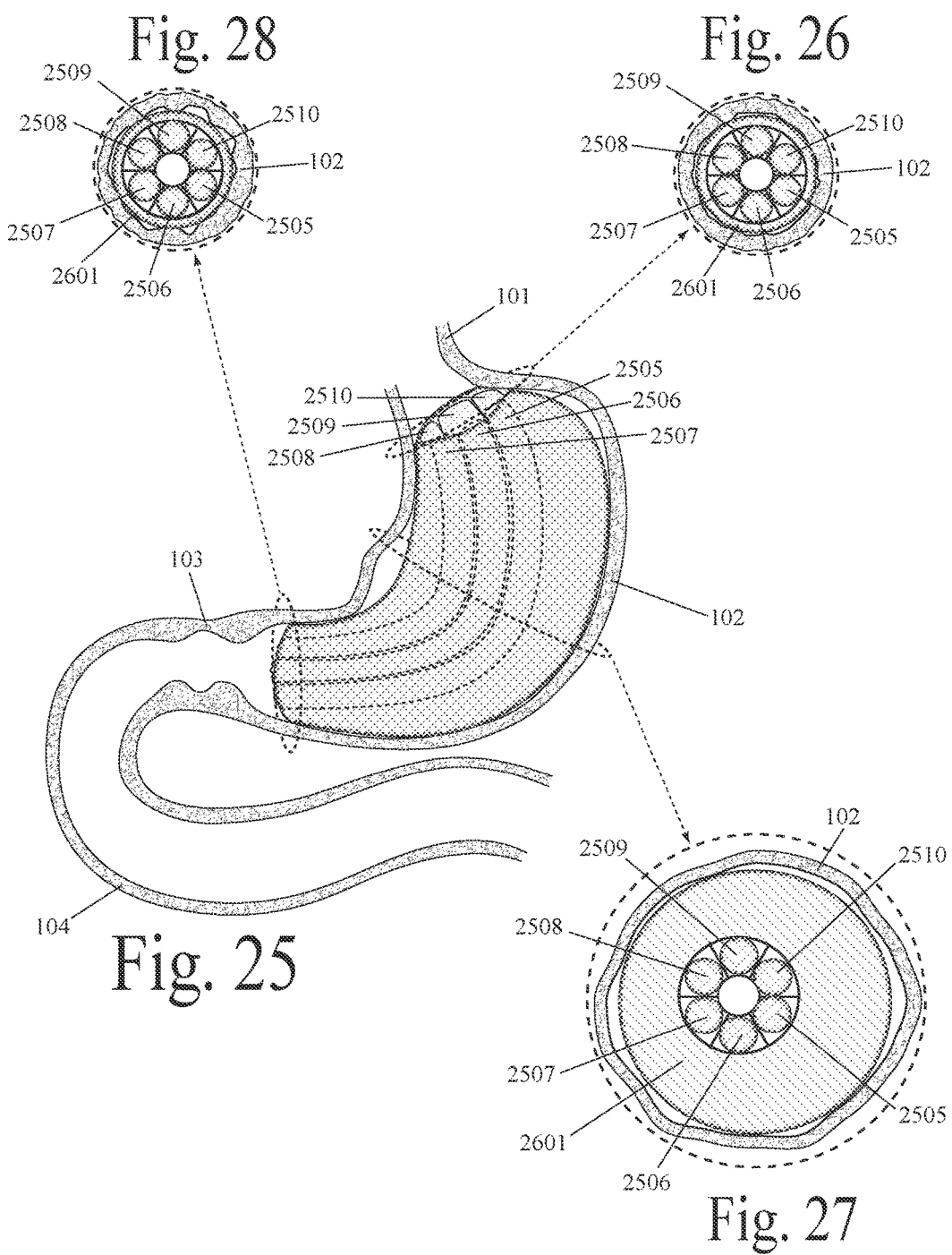

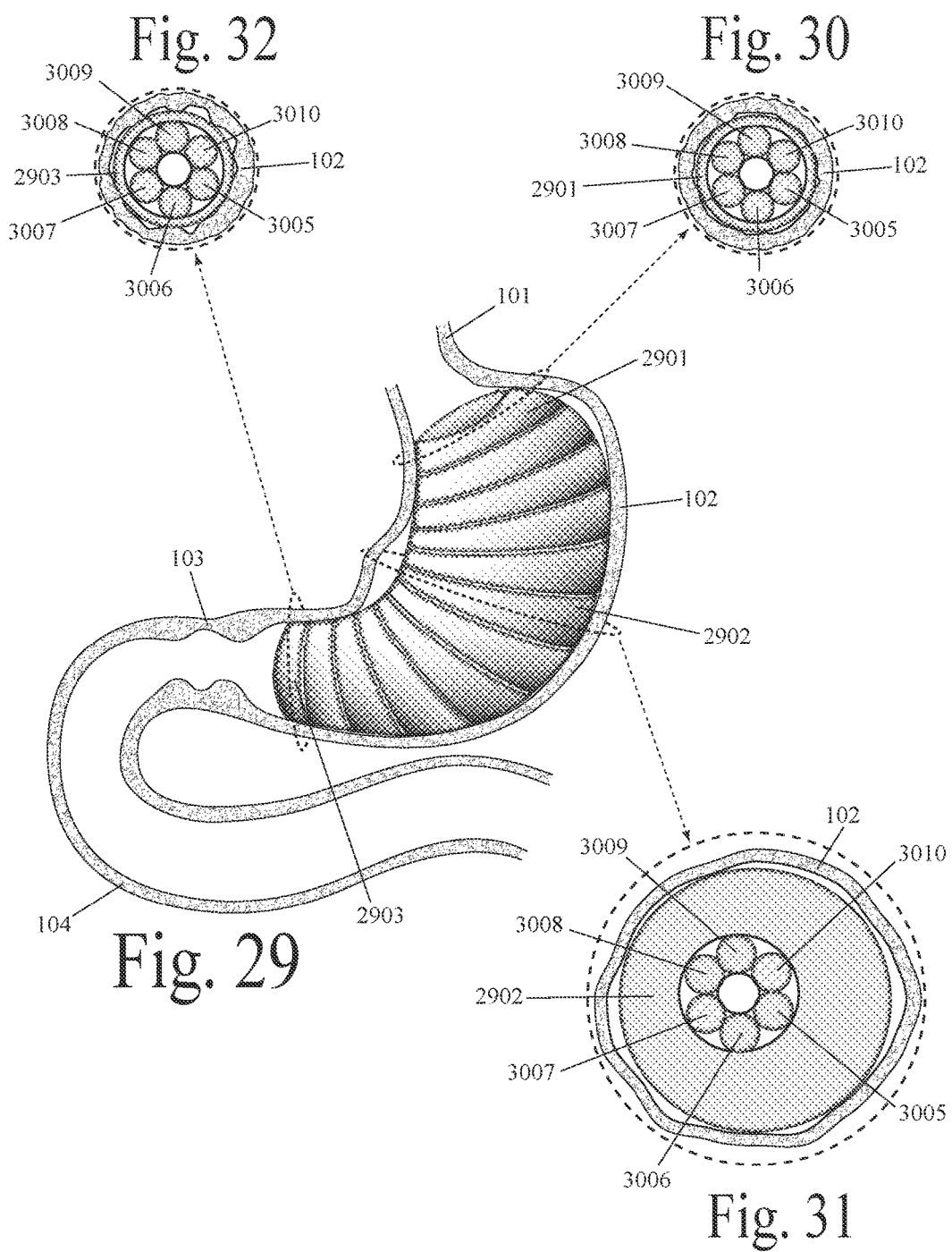

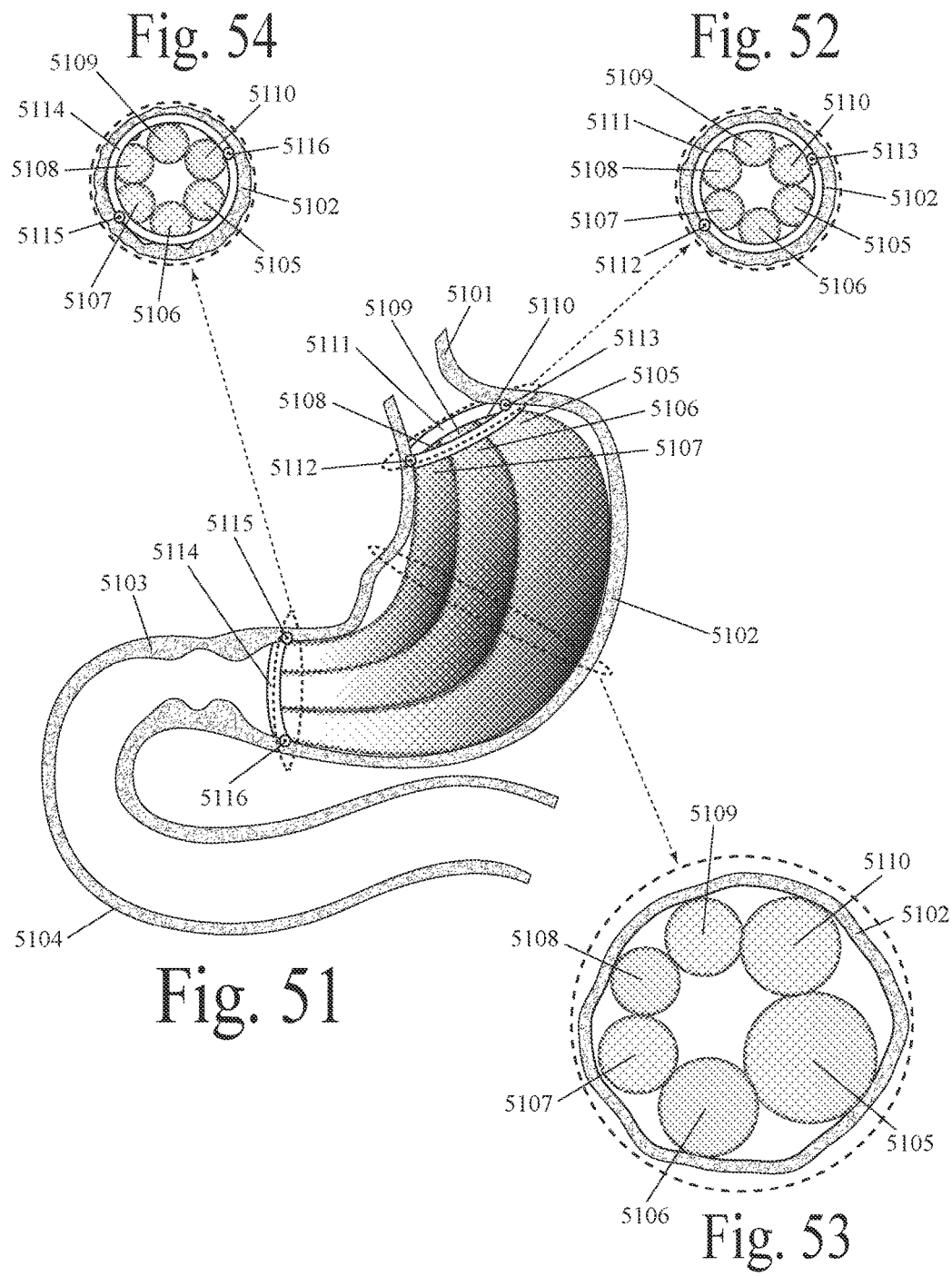

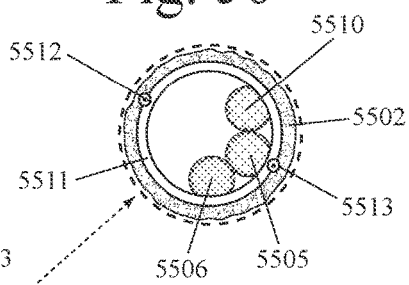
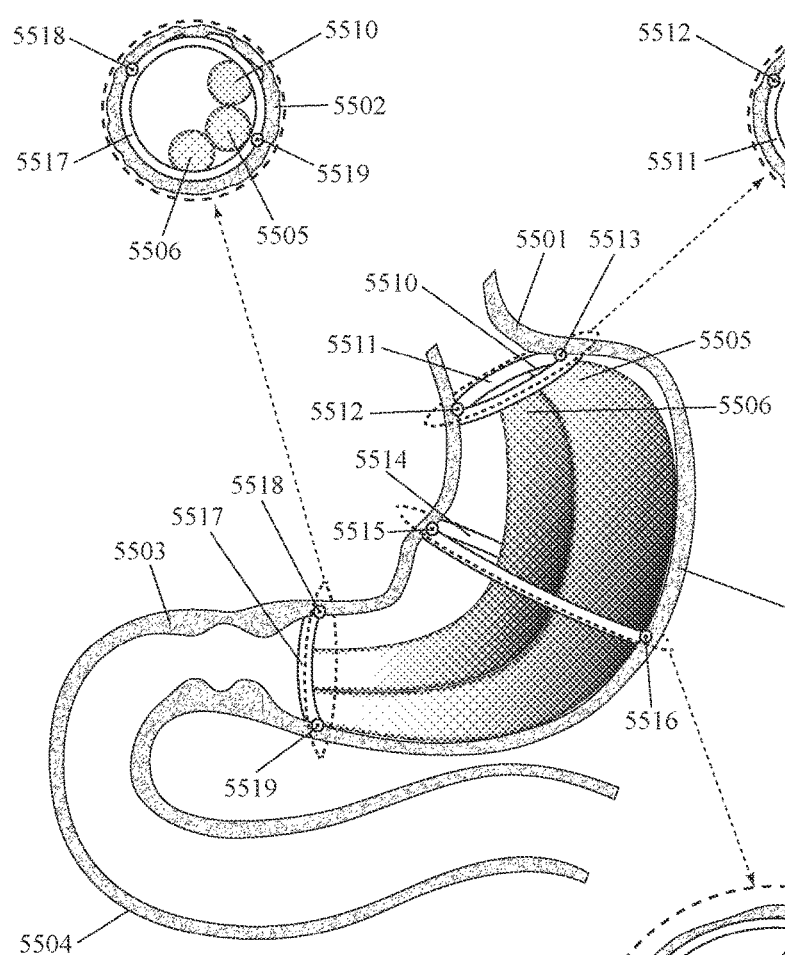
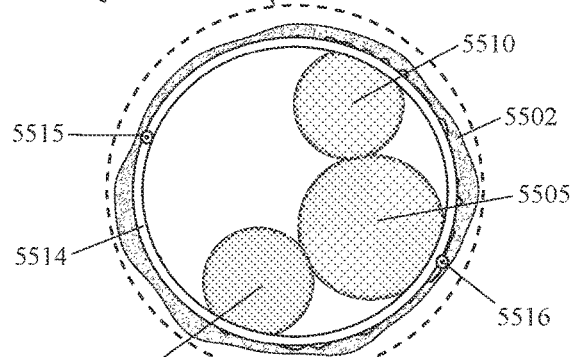

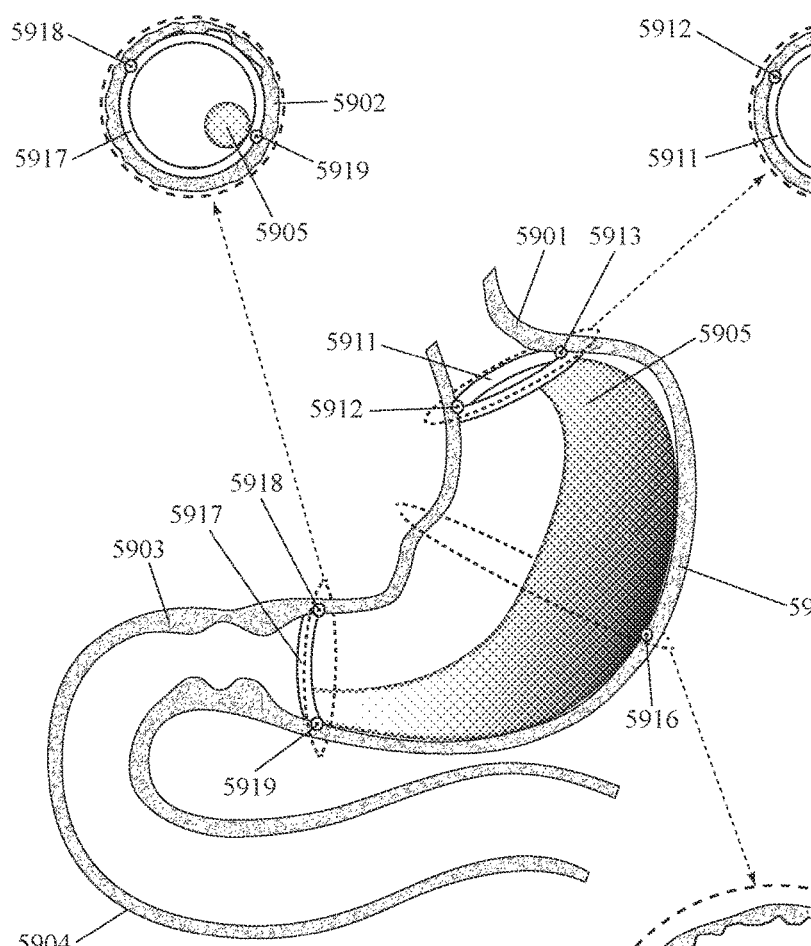
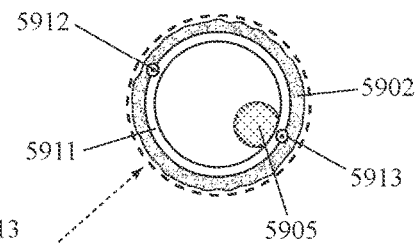
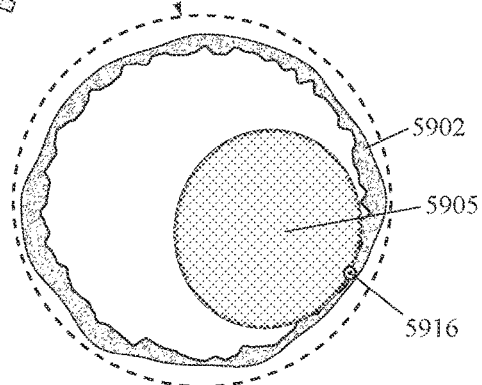
Fig. 62
Fig. 60
Fig. 59
Fig. 61

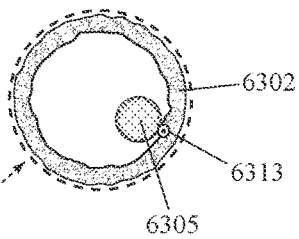
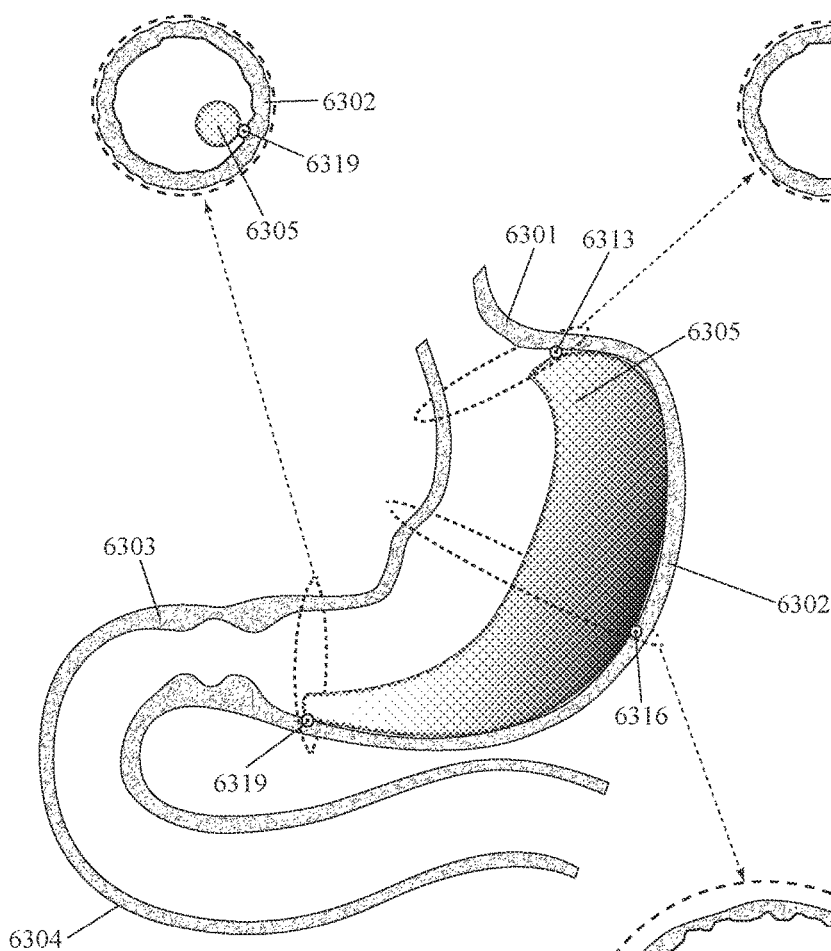
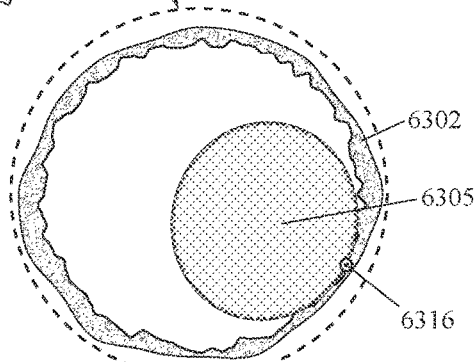

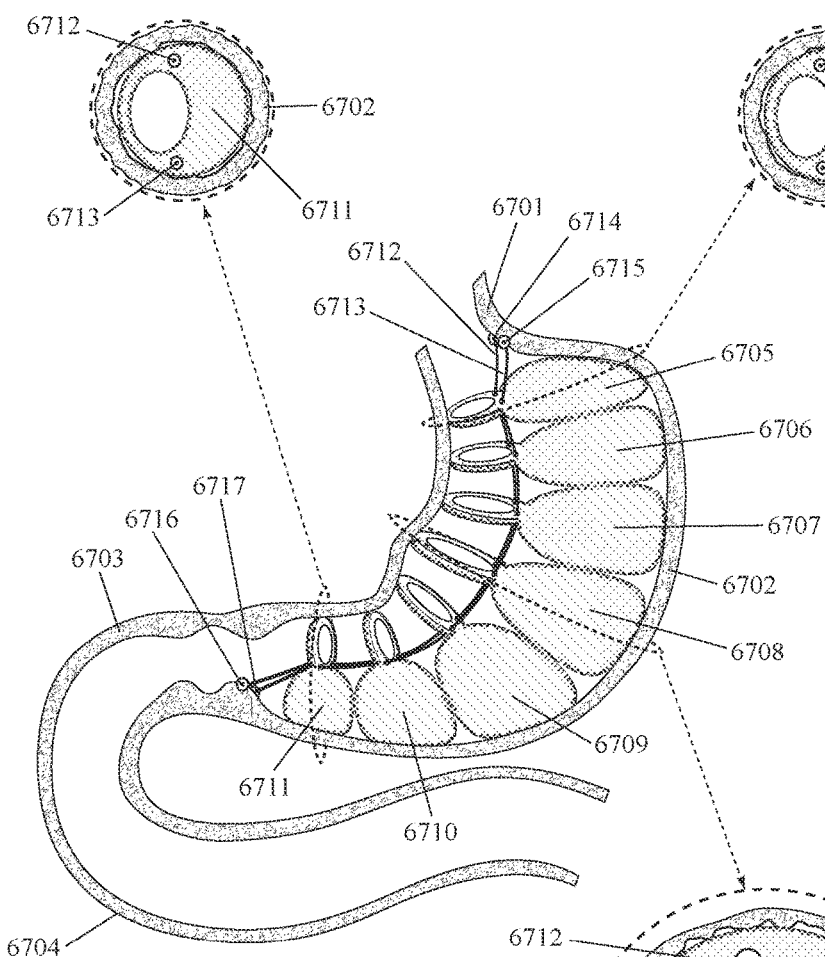
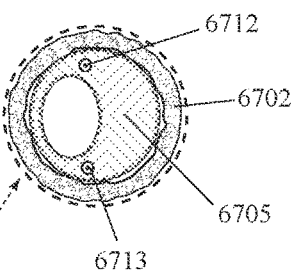
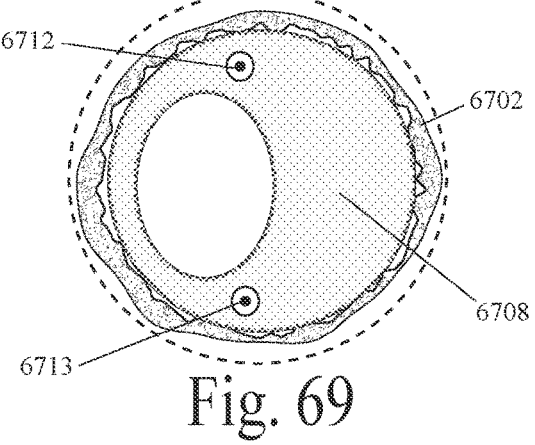
Fig. 67
Fig. 68
Fig. 69
Fig. 70

COLONNADE (TM) EXPANDABLE INTRAGASTRIC FOOD FLOW LUMEN DEVICE

CROSS-REFERENCE TO RELATED APPLICATIONS

This patent application: (a) is a continuation-in-part of U.S. patent application Ser. No. 13/616,238 entitled "Interactive Voluntary and Involuntary Caloric Intake Monitor" by Robert A. Connor filed on Sep. 14, 2012; (b) is a continuation-in-part of U.S. patent application Ser. No. 13/797,955 entitled "Device for Selectively Reducing Absorption of Unhealthy Food" by Robert A. Connor filed on Mar. 12, 2013; and also (c) claims the priority benefit of U.S. Provisional Patent Application 62/096,199 entitled "Colonnade (TM): Expandable Intragastric Food Flow Lumen Device" by Robert A. Connor filed on Dec. 23, 2014. The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to intragastric devices for reducing food consumption and/or absorption.

INTRODUCTION

The United States population has some of the highest prevalence rates of obese and overweight people in the world. Further, these rates have increased dramatically during recent decades. In the late 1990's, around one in five Americans was obese. Today, that figure has increased to around one in three. It is estimated that around one in five American children is now obese. The prevalence of Americans who are generally overweight is estimated to be as high as two out of three. Despite the considerable effort that has been focused on developing new approaches for preventing and treating obesity, the problem is growing. Metabolic surgery (such as gastric bypass surgery or gastric sleeve surgery) offers approaches for reducing food consumption and/or absorption which are appropriate for some people, but are not appropriate for everyone with a weight problem and are generally not adjustable or reversible. There is an unmet need for an intragastric device which can simulate some of the beneficial effects of gastric sleeve surgery, but which is adjustable and reversible. Such a device is disclosed herein.

REVIEW OF THE PRIOR ART

It can be challenging trying to classify relevant art into discrete categories. However, classification of relevant art into categories, even if imperfect, can be an invaluable tool for reviewing a large body of relevant art. Towards this end, I herein identify eight categories of relevant art and provide examples of relevant art in each category (including patent or patent application number, inventor, publication date, and title). Some examples of relevant art disclose multiple concepts and thus appear in more than one category.

The eight categories of relevant art herein are as follows: (1) general intragastric balloon art; (2) intragastric balloon with (automatically) adjustable size; (3) multiple intragastric balloons or intragastric balloon with multiple chambers; (4) balloons within a non-balloon intragastric structure; (5) intragastric balloon with lumens or holes for food flow; (6) intragastric balloon with drug delivery mechanism; (7) balloon and/or expandable member outside the stomach; and (8) other art relevant to intragastric balloons. Art with a priority date after that of this present invention is relevant art, but not necessarily prior art.

1) General Intragastric Balloon Art

This category includes early and general art related to the use of balloons within the stomach. Relevant art that appears to be in this category includes U.S. Pat. No. 4,694,827 (Weiner et al., Sep. 22, 1987, "Inflatable Gastric Device for Treating Obesity and Method of Using the Same"); Pat. No. 5,234,454 (Bangs, Aug. 10, 1993, "Percutaneous Intragastric Balloon Catheter and Method for Controlling Body Weight Therewith"); Pat. No. 5,993,473 (Chan et al., Nov. 30, 1999, "Expandable Body Device for the Gastric Cavity and Method"); Pat. No. 8,202,291 (Brister et al., Jun. 19, 2012, "Intragastric Device"); and Pat. No. 8,740,927 (Brister et al., Jun. 3, 2014, "Intragastric Device").

Relevant art that appears to be in this category also includes U.S. patent applications: 20050267405 (Shah, Dec. 1, 2005, "Gastro-Occlusive Device"); 20080208241 (Weiner et al., Aug. 28, 2008, "Multi-Method and Multi-Apparatus for Treating Obesity"); 20100100115 (Soetermans et al., Apr. 22, 2010, "Foam Filled Intragastric Balloon for Treating Obesity"); 20100191270 (Garza Alvarez, Jul. 29, 2010, "Intragastric Balloon Assembly"); 20110092998 (Hirszowicz et al., Apr. 21, 2011, "Balloon Hydraulic and Gaseous Expansion System"); 20120191123 (Brister et al., Jul. 26, 2012, "Intragastric Device"); 20120191124 (Brister et al., Jul. 26, 2012, "Intragastric Device"); 20120232576 (Brister et al., Sep. 13, 2012, "Intragastric Device"); 20130012980 (Brister et al., Jan. 10, 2013, "Intragastric Device"); 20130226219 (Brister et al., Aug. 29, 2013, "Intragastric Device"); and 20150223956 (Nadler et al., Aug. 13, 2015, "Anchored Non-Spherical Balloon for the Treatment of Obesity").

2) Intragastric Balloon with (Automatically) Adjustable Size

This category includes intragastric balloons whose size can be adjusted manually and/or whose size is automatically adjusted in vivo. Relevant art that appears to be in this category includes U.S. Pat. No. 5,259,399 (Brown, Nov. 9, 1993, "Device and Method of Causing Weight Loss Using Removable Variable Volume Intragastric Bladder"); U.S. Pat. No. 6,454,785 (De Hoyos Garza, Sep. 24, 2002, "Percutaneous Intragastric Balloon Catheter for the Treatment of Obesity"); U.S. Pat. No. 6,579,301 (Bales et al., Jun. 17, 2003, "Intragastric Balloon Device Adapted to be Repeatedly Varied in Volume Without External Assistance"); U.S. Pat. No. 6,733,512 (McGhan, May 11, 2004, "Self-Deflating Intragastric Balloon"); U.S. Pat. No. 6,981,980 (Sampson et al., Jan. 3, 2006, "Self-Inflating Intragastric Volume-Occupying Device"); U.S. Pat. No. 7,056,305 (Garza Alvarez, Jun. 6, 2006, "Intragastric Balloon Assembly"); U.S. Pat. No. 7,112,186 (Shah, Sep. 26, 2006, "Gastro-Occlusive Device"); U.S. Pat. No. 7,470,251 (Shah, Dec. 30, 2008, "Gastro-Occlusive Device"); Pat. No. 8,236,023 (Birk et al., Aug. 7, 2012, "Apparatus and Method for Volume Adjustment of Intragastric Balloons"); Pat. No. 8,282,666 (Birk, Oct. 9, 2012, "Pressure Sensing Intragastric Balloon"); and Pat. No. 8,292,911 (Brister et al., Oct. 23, 2012, "Intragastric Device").

Relevant art that appears to be in this category also includes U.S. patent applications: 20010037127 (De Hoyos Garza, Nov. 1, 2001, "Percutaneous Intragastric Balloon Catheter for the Treatment of Obesity"); 20040059289 (Garza Alvarez, Mar. 25, 2004, "Intragastric Balloon Assembly"); 20050159769 (Alverdy, Jul. 21, 2005, "Balloon System and Methods for Treating Obesity"); 20060058829 (Sampson et al., Mar. 16, 2006, "Intragastric Volume-Occupying Device"); 20070173881 (Birk et al., Jul. 26, 2007, "Apparatus and Method for Volume Adjustment of Intragastric Balloons"); 20080306506 (Leatherman, Dec. 11, 2008, "Self-Inflating and Deflating Intragastric Balloon Implant Device"); and 20090048624 (Alverdy, Feb. 19, 2009, "Balloon System and Methods for Treating Obesity").

Relevant art that appears to be in this category also includes U.S. patent applications: 20090131968 (Birk, May 21, 2009, "Pressure Sensing Intragastric Balloon"); 20090131968 (Birk, May 21, 2009, "Pressure Sensing Intragastric Balloon"); 20100130998 (Alverdy, May 27, 2010, "Balloon System and Methods for Treating Obesity"); 20100152764 (Merkle, Jun. 17, 2010, "Device for Treating Obesity"); 20110034760 (Brynelsen et al., Feb. 10, 2011, "Feedback Systems and Methods to Enhance Obstructive and Other Obesity Treatments"); 20120095496 (Dominguez et al., Apr. 19, 2012, "Reactive Intragastric Implant Devices"); 20130274789 (Brooks et al., Oct. 17, 2013, "Floating Gastrointestinal Anchor"); and 20150150699 (Pattison et al., Jun. 4, 2015, "Anchorable Size-Varying Gastric Balloons for Weight Loss").

3) Multiple Intragastric Balloons or Intragastric Balloon with Multiple Chambers This category includes devices with multiple intragastric balloons and/or intragastric balloons with multiple chambers. Relevant art that appears to be in this category includes: U.S. Pat. No. 8,066,780 (Chen et al., Nov. 29, 2011, "Methods for Gastric Volume Control"); Pat. No. 8,142,469 (Sosnowski et al., Mar. 27, 2012, "Gastric Space Filler Device, Delivery System, and Related Methods"); and U.S. patent applications: 20050267596 (Chen et al., Dec. 1, 2005, "Devices and Systems for Gastric Volume Control"); 20070118168 (Lointier et al., May 24, 2007, "Multiple-Pouch Intragastric Balloons, Surgical Device for Expanding Said Balloon and Method for Making Same"); 20070149994 (Sosnowski et al., Jun. 28, 2007, "Intragastric Space Filler and Methods of Manufacture"); 20080243166 (Paganon et al., Oct. 2, 2008, "Pouch-Equipped Intragastric Balloon"); and 20080319471 (Sosnowski et al., Dec. 25, 2008, "Gastric Space Filler Device, Delivery System, and Related Methods").

Relevant art that appears to be in this category also includes U.S. patent applications: 20090082644 (Li, Mar. 26, 2009, "Devices, Systems, Kits and Methods for Treatment of Obesity"); 20090275973 (Chen et al., Nov. 4, 2009, "Devices and Systems for Gastric Volume Control"); 20090275973 (Chen et al., Nov. 4, 2009, "Devices and Systems for Gastric Volume Control"); 20110178544 (Sosnowski et al., Jul. 21, 2011, "Gastric Space Filler Delivery System and Related Methods"); 20120089170 (Dominguez, Apr. 12, 2012, "Intragastric Balloon Geometries"); 20120089172 (Babkes et al., Apr. 12, 2012, "Re-Shaping Intragastric Implants"); 20120095495 (Babkes et al., Apr. 19, 2012, "Space-Filling Intragastric Implants with Fluid Flow"); 20120191125 (Babkes et al., Jul. 26, 2012, "Intragastric Implants with Multiple Fluid Chambers"); and 20120265030 (Li, Oct. 18, 2012, "Devices Systems Kits and Methods for Treatment of Obesity").

4) Balloon(s) within a Non-Balloon Intragastric Structure

This category includes devices wherein one or more intragastric balloons are expanded within a non-balloon intragastric structure. Relevant art that appears to be in this category includes: U.S. Pat. No. 8,066,780 (Chen et al., Nov. 29, 2011, "Methods for Gastric Volume Control"); and U.S. patent applications 20050267596 (Chen et al., Dec. 1, 2005, "Devices and Systems for Gastric Volume Control"); 20090275973 (Chen et al., Nov. 5, 2009, "Devices and Systems for Gastric Volume Control"); and 20090275973 (Chen et al., Nov. 5, 2009, "Devices and Systems for Gastric Volume Control").

5) Intragastric Balloon with Lumen(s) or Hole(s) for Food Flow

This category includes intragastric balloons with one or more lumens or holes through which food can flow. Relevant art that appears to be in this category includes U.S. Pat. No. 4,416,267 (Garren et al., Nov. 22, 1983, "Method and Apparatus for Treating Obesity"); Pat. No. 4,899,747 (Garren et al., Feb. 13, 1990, "Method and Apparatus for Treating Obesity"); and Pat. No. 8,142,469 (Sosnowski et al., Mar. 27, 2012, "Gastric Space Filler Device, Delivery System, and Related Methods").

Relevant art that appears to be in this category also includes U.S. patent applications: 20070078476 (Hull et al., Apr. 4, 2007, "Overweight Control Apparatuses for Insertion into the Stomach"); 20070149994 (Sosnowski et al., Jun. 28, 2007, "Intragastric Space Filler and Methods of Manufacture"); 20070239284 (Skerven et al., Nov. 11, 2007, "Coiled Intragastric Member for Treating Obesity"); 20080097513 (Kaji et al., Apr. 24, 2008, "Intragastric Balloon"); 20080319471 (Sosnowski et al., Dec. 25, 2008, "Gastric Space Filler Device, Delivery System, and Related Methods"); 20110178544 (Sosnowski et al., Jul. 21, 2011, "Gastric Space Filler Delivery System and Related Methods"); 20120022322 (Pasricha, Jan. 26, 2012, "Methods and Devices for Treating Obesity"); 20120089170 (Dominguez, Apr. 12, 2012, "Intragastric Balloon Geometries"); 20120089172 (Babkes et al., Apr. 12, 2012, "Re-Shaping Intragastric Implants"); 20120095495 (Babkes et al., Apr. 19, 2012, "Space-Filling Intragastric Implants with Fluid Flow"); and 20150150699 (Pattison et al., Jun. 4, 2015, "Anchorable Size-Varying Gastric Balloons for Weight Loss").

6) Intragastric Balloon with Drug Delivery Mechanism

This category includes intragastric balloons which include a drug delivery mechanism. Relevant art that appears to be in this category includes U.S. Pat. No. 7,854,745 (Brister et al., Dec. 21, 2010, "Intragastric Device"); Pat. No. 8,162,969 (Brister et al., Apr. 24, 2012, "Intragastric Device"); and 8226602 (Quijana et al., Jul. 24, 2012, "Intragastric Balloon System and Therapeutic Processes and Products").

Relevant art that appears to be in this category also includes U.S. patent applications: 20070265598 (Karasik, Nov. 15, 2007, "Device and Method for Treating Weight Disorders"); 20080243071 (Quijano et al., Oct. 2, 2008, "Intragastric Balloon System and Therapeutic Processes and Products"); 20100100116 (Brister et al., Apr. 22, 2010, "Intragastric Volume-Occupying Device and Method for Fabricating Same"); 20100100117 (Brister et al., Apr. 22, 2010, "Intragastric Device"); 20100137897 (Brister et al., Jun. 3, 2010, "Intragastric Device"); 20120245553 (Raven et al., Sep. 27, 2012, "Intragastric Volume Occupying Device with Active Agents"); 20120265234 (Brister et al., Oct. 18, 2012, "Intragastric Device"); 20120289992 (Quijano et al., Nov. 15, 2012, "Intragastric Balloon System and Therapeutic Processes and Products"); and 20130226221 (Hyde et al., Aug. 29, 2013, "Devices, Systems, and Methods to Control Stomach Volume").

7) Balloon and/or Expandable Member Outside the Stomach

This category includes balloons or other expandable members which are located outside the stomach, but can press against the stomach when expanded. Relevant art that appears to be in this category includes U.S. Pat. No. 8,001,974 (Makower et al., Aug. 23, 2011, "Devices and Methods for Treatment of Obesity"); Pat. No. 8,070,768 (Kim et al., Dec. 6, 2011, "Devices and Methods for Treatment of Obesity"); Pat. No. 8,187,297 (Makower et al., May 29, 2012, "Devices and Methods for Treatment of Obesity"); Pat. No. 8,192,455 (Brazzini et al., Jun. 5, 2012, "Compressive Device for Percutaneous Treatment of Obesity"); and Pat. No. 8,343,031 (Gertner, Jan. 1, 2013, "Obesity Treatment Systems").

Relevant art that appears to be in this category also includes U.S. patent applications: 20080147002 (Gertner, Jun. 19, 2008, "Obesity Treatment Systems"); 20080161717 (Gertner, Jul. 3, 2008, "Obesity Treatment Systems"); 20080188766 (Gertner, Aug. 7, 2008, "Obesity Treatment Systems"); 20080208240 (Paz, Aug. 28, 2008, "Implantable Device for Obesity Prevention"); 20110295056 (Aldridge et al., Dec. 1, 2011, "Systems and Methods for Gastric Volume Regulation"); 20110295057 (Aldridge et al., Dec. 1, 2011, "Systems and Methods for Gastric Volume Regulation"); 20120215249 (Brazzini et al., Aug. 23, 2012, "Compressive Device for Percutaneous Treatment of obesity"); 20120253378 (Makower et al., Oct. 4, 012, "Devices and Methods for Treatment of Obesity"); and 20120283766 (Makower et al., Nov. 8, 2012, "Devices and Methods for Treatment of Obesity").

8) Other Art Relevant to Intragastric Balloons

This category includes other art which is relevant to intragastric balloons but does not fit (only) into one of the above categories. Relevant art that appears to be in this category includes U.S. Pat. No. 7,682,306 (Shah, Mar. 23, 2010, "Therapeutic Intervention Systems Employing Implantable Balloon Devices"); Pat. No. 7,947,038 (Edwards, May 24, 2011, "Obesity Treatment System Including Inflatable Balloon Structures with Micropores for Transport of Liquid"); and Pat. No. 8,100,932 (Nihalani, Jan. 24, 2012, "Method and Apparatus for Treating Obesity and Controlling Weight Gain Using Self-Expanding Intragastric Devices").

Relevant art that appears to be in this category also includes U.S. patent applications: 20060020278 (Burnett et al., Jan. 26, 2006, "Gastric Retaining Devices and Methods"); 20070239284 (Skerven et al., Nov. 11, 2007, "Coiled Intragastric Member for Treating Obesity"); 20070265646 (McCoy et al., Nov. 15, 2007, "Dynamically Adjustable Gastric Implants"); 20090171383 (Cole et al., Jul. Feb. 2009, "Gastric Space Occupier Systems and Methods of Use"); 20090187200 (Burnett et al., Jul. 23, 2009, "Gastric Retaining Devices and Methods"); 20090187201 (Burnett et al., Jul. 23, 2009, "Gastric Retaining Devices and Methods"); 20090216262 (Burnett et al., Aug. 27, 2009, "Gastric Retaining Devices and Methods"); 20090259236 (Burnett et al., Oct. 15, 2009, "Gastric Retaining Devices and Methods"); 20100049224 (Vargas, Feb. 25, 2010, "Intragastric Implant Devices"); 20100331617 (Forsell, Dec. 30, 2010, "Device, System and Method for Treating Obesity"); and 20100332000 (Forsell, Dec. 30, 2010, "Device for Treating Obesity").

Relevant art that appears to be in this category also includes U.S. patent applications: 20110319924 (Cole et al., Dec. 29, 2011, "Gastric Space Occupier Systems and Methods of Use"); 20120004676 (Vargas, Jan. 5, 2012, "Intragastric Implant Devices"); 20120053613 (Weitzner et al., Mar. 1, 2012, "Gastric Filler Devices for Obesity Therapy"); 20120095494 (Dominguez et al., Apr. 19, 2012, "Intragastric Implants with Collapsible Frames"); 20120095496 (Dominguez et al., Apr. 19, 2012, "Reactive Intragastric Implant Devices"); 20120191126 (Pecor et al., Jul. 26, 2012, "Inflation and Deflation Mechanisms for Inflatable Medical Devices"); 20120232361 (Birk, Sep. 13, 2012, "Bariatric Instrument or Accessory with Sensors"); 20120232577 (Birk et al., Sep. 13, 2012, "Bariatric Device and Method for Weight Loss"); 20120323160 (Babkes, Dec. 20, 2012, "Upper Stomach Gastric Implants"); 20130079603 (Vargas, Mar. 28, 2013, "Intragastric Implant Devices"); and 20140221899 (Vargas, Aug. 7, 2014, "Intragastric Implant Devices").

SUMMARY OF THE INVENTION

This invention is an implantable expandable intragastric device for reducing food consumption and/or absorption. This device comprises one or more expandable members which collectively form a restrictive food lumen within a stomach which offers some of the beneficial effects of gastric sleeve surgery, while also being adjustable and reversible. In an example, this device can be embodied in a plurality of longitudinal expandable members which are arranged in a colonnade configuration within the stomach to form a restrictive food lumen within a stomach. In an example, this device can be embodied in a longitudinal series of toroidal expandable members which forms a restrictive food lumen within a stomach.

In an example, the configuration of this device can be remotely adjusted by wireless control of implanted pumps which pump a flowable substance between the interiors of one or more of the expandable members. In an example, pumping a flowable substance between the interiors of one or more expandable members changes the shape and/or size of the restrictive food lumen created by this device. In an example, pumping a flowable substance between the interiors one or more expandable members changes the rate of food flow through the stomach, the capacity of the stomach to hold food, and/or the amount of food absorbed by the body.

BRIEF DESCRIPTION OF THE FIGURES

FIGS. 1 through 83 show examples of how this invention can be embodied, but they do not limit the full generalizability of the claims.

FIG. 1 shows a side view of an intragastric device comprising expandable members with circular cross sections which form a food flow lumen.

FIG. 2 shows a cross-sectional view of the device in FIG. 1 near the gastroesophageal junction.

FIG. 3 shows a cross-sectional view of the device in FIG. 1 near the middle of the stomach.

FIG. 4 shows a cross-sectional view of the device in FIG. 1 near the pylorus.

FIG. 5 shows a side view of an intragastric device comprising expandable members with trapezoidal cross sections which form a food flow lumen.

FIG. 6 shows a cross-sectional view of the device in FIG. 5 near the gastroesophageal junction.

FIG. 7 shows a cross-sectional view of the device in FIG. 5 near the middle of the stomach.

FIG. 8 shows a cross-sectional view of the device in FIG. 5 near the pylorus.

FIG. 9 shows a side view of an intragastric device comprising expandable members and a sinusoidal ring which forms a food flow lumen.

FIG. 10 shows a cross-sectional view of the device in FIG. 9 near the gastroesophageal junction.

FIG. 11 shows a cross-sectional view of the device in FIG. 9 near the middle of the stomach.

FIG. 12 shows a cross-sectional view of the device in FIG. 9 near the pylorus.

FIG. 13 shows a side view of an intragastric device comprising expandable members, centrally connected by ring, which form a food flow lumen.

FIG. 14 shows a cross-sectional view of the device in FIG. 13 near the gastroesophageal junction.

FIG. 15 shows a cross-sectional view of the device in FIG. 13 near the middle of the stomach.

FIG. 16 shows a cross-sectional view of the device in FIG. 13 near the pylorus.

FIG. 17 shows a side view of an intragastric device comprising expandable members in inner and outer rings which form a food lumen.

FIG. 18 shows a cross-sectional view of the device in FIG. 17 near the gastroesophageal junction.

FIG. 19 shows a cross-sectional view of the device in FIG. 17 near the middle of the stomach.

FIG. 20 shows a cross-sectional view of the device in FIG. 17 near the pylorus.

FIG. 21 shows a side view of an intragastric device comprising expandable members with keystone-shaped cross sections in an inner ring.

FIG. 22 shows a cross-sectional view of the device in FIG. 21 near the gastroesophageal junction.

FIG. 23 shows a cross-sectional view of the device in FIG. 21 near the middle of the stomach.

FIG. 24 shows a cross-sectional view of the device in FIG. 21 near the pylorus.

FIG. 25 shows a side view of an intragastric device comprising expandable members in keystone-shaped chambers in an inner ring.

FIG. 26 shows a cross-sectional view of the device in FIG. 25 near the gastroesophageal junction.

FIG. 27 shows a cross-sectional view of the device in FIG. 25 near the middle of the stomach.

FIG. 28 shows a cross-sectional view of the device in FIG. 25 near the pylorus.

FIG. 29 shows a side view of an intragastric device with a longitudinal stack of toroidal expandable members in an outer ring.

FIG. 30 shows a cross-sectional view of the device in FIG. 29 near the gastroesophageal junction.

FIG. 31 shows a cross-sectional view of the device in FIG. 29 near the middle of the stomach.

FIG. 32 shows a cross-sectional view of the device in FIG. 29 near the pylorus.

FIG. 51 shows a side view of an intragastric device comprising upper and lower intragastric rings to which a circular array of longitudinal expandable members are connected to form a food lumen.

FIG. 52 shows a cross-sectional view of the device in FIG. 51 near the gastroesophageal junction.

FIG. 53 shows a cross-sectional view of the device in FIG. 51 near the middle of the stomach.

FIG. 54 shows a cross-sectional view of the device in FIG. 51 near the pylorus.

FIG. 55 shows a side view of an intragastric device comprising upper, middle, and lower intragastric rings to which a semi-circular array of longitudinal expandable members are connected to form a food lumen.

FIG. 56 shows a cross-sectional view of the device in FIG. 55 near the gastroesophageal junction.

FIG. 57 shows a cross-sectional view of the device in FIG. 55 near the middle of the stomach.

FIG. 58 shows a cross-sectional view of the device in FIG. 55 near the pylorus.

FIG. 59 shows a side view of an intragastric device comprising upper and lower intragastric rings to which a longitudinal expandable member along the greater curve of the stomach is connected to form a food lumen.

FIG. 60 shows a cross-sectional view of the device in FIG. 59 near the gastroesophageal junction.

FIG. 61 shows a cross-sectional view of the device in FIG. 59 near the middle of the stomach.

FIG. 62 shows a cross-sectional view of the device in FIG. 59 near the pylorus.

FIG. 63 shows a side view of an intragastric device comprising a longitudinal expandable member connected to the greater curve of the stomach.

FIG. 64 shows a cross-sectional view of the device in FIG. 63 near the gastroesophageal junction.

FIG. 65 shows a cross-sectional view of the device in FIG. 63 near the middle of the stomach.

FIG. 66 shows a cross-sectional view of the device in FIG. 63 near the pylorus.

FIG. 67 shows a side view of an intragastric device comprising a longitudinal series of expandable members with toriodal portions along the lesser curve of the stomach which form a food lumen.

FIG. 68 shows a cross-sectional view of the device in FIG. 67 near the gastroesophageal junction.

FIG. 69 shows a cross-sectional view of the device in FIG. 67 near the middle of the stomach.

FIG. 70 shows a cross-sectional view of the device in FIG. 67 near the pylorus.

FIG. 83 shows the device in FIG. 82 after the spiral has been inserted into the stomach and the upper ends of the longitudinal flexible members have been attached to stomach walls.

DETAILED DESCRIPTION OF THE FIGURES

Figure 83:
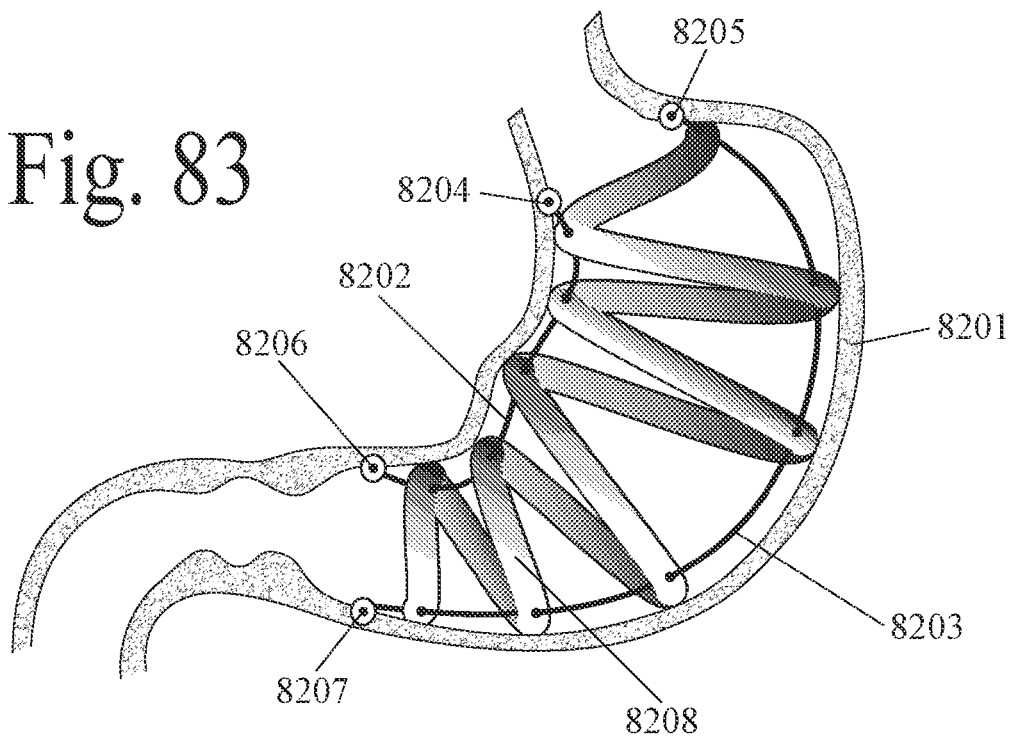

FIGS. 1 through 83 show examples of how this invention can be embodied, but they do not limit the full generalizability of the claims. This invention is an implantable expandable intragastric device for reducing food consumption and/or absorption. This device comprises one or more expandable members which collectively form a restrictive food lumen within a stomach which offers some of the beneficial effects of gastric sleeve surgery, while also being adjustable and reversible. In an example, this device can be embodied in a plurality of longitudinal expandable members which are arranged in a colonnade configuration within the stomach to form a restrictive food lumen within a stomach. In an example, this device can be embodied in a longitudinal series of toroidal expandable members which forms a restrictive food lumen within a stomach.

In an example, the configuration of this device can be remotely adjusted by wireless control of implanted pumps which pump a flowable substance between the interiors of one or more of the expandable members. In an example, pumping a flowable substance between the interiors of one or more expandable members changes the shape and/or size of the restrictive food lumen created by this device. In an example, pumping a flowable substance between the interiors one or more expandable members changes the rate of food flow through the stomach, the capacity of the stomach to hold food, and/or the amount of food absorbed by the body.

In an example, this invention can be embodied in an expandable intragastric food flow lumen device which comprises: (a) a plurality of expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) a food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

In an example, a plurality of expandable members can be inserted into a stomach through the esophagus and then expanded within the stomach by filling them with a flowable substance (such as a liquid or a gas). In an example, at a later time the flowable substance can be removed from this plurality of expandable members and these members can be removed from the stomach through the esophagus. In an example, the expandable members can be left within the stomach for a period of several months or years before being removed. In an example, the expandable members can restrict the flow of food through the stomach and/or the amount of food which the stomach can contain during this period of time. In an example, the expandable members can restrict the flow of food through the stomach to food flow through a food flow lumen which is encircled, encompassed, contained, formed, and/or surrounded by the expandable members.

In an example, a plurality of expandable members can be separate from each other. In an example, a plurality of expandable members can be connected to each other. In an example, a plurality of expandable members can be pairwise connected and their central axes can be arranged in a circular or polygonal formation. In an example, expandable members can be longitudinal expandable members. In an example, there can be between 3 and 12 expandable members. In an example, a plurality of expandable members can be chambers in a multi-chamber member. In an example, a multi-chamber member can have between 3 and 12 chambers. In an example, expandable members or chambers can be separately or individually expanded by being filled with a flowable substance after insertion into a stomach. In an example, expandable members or chambers can be jointly or simultaneously expanded by being filled with a flowable substance after insertion into a stomach.

In an example, the walls of a plurality of expandable members can form a food flow lumen. In an example, the walls of a plurality of expandable members which are connected and their central axes can be arranged in a circular or polygonal formation can form a central food flow lumen. In an example, expandable members can be arranged in a circle and the center-facing portions of the walls of the expandable members can collectively form a food flow lumen. In an example, a food flow lumen can have walls which are encircled by, but not formed by, expandable members.

In an example, expandable members can be distributed around at least 50% of the perimeter of a food flow lumen. In an example, expandable members can be distributed around at least 75% of the perimeter of a food flow lumen. In an example, expandable members can be distributed around the entire perimeter of a food flow lumen. In an example, expandable members can form a circle, oval, egg shape, or polygon around a food flow lumen. In an example, expandable members can collectively comprise a ring of arcuate columns (or colonnade) around a food flow lumen. In an example, expandable members can collectively comprise a ring of arcuate columns (or colonnade) with a food flow lumen in the middle.

In an example, expandable members can collectively comprise a ring (or section of a ring) which forms, encircles, encompasses, encloses, contains, and/or surrounds at least 50% of the perimeter of an artificial food flow lumen. In an example, expandable members can collectively comprise a ring (or section of a ring) which forms, encircles, encompasses, encloses, contains, and/or surrounds at least 75% of the perimeter of an artificial food flow lumen. In an example, expandable members can collectively comprise a ring (or section of a ring) which forms, encircles, encompasses, encloses, contains, and/or surrounds the entire perimeter of an artificial food flow lumen.

In an example, expandable members can be longitudinal expandable members. In an example, a longitudinal expandable member can have a proximal end which is configured to be closer to the gastroesophageal junction after expansion, a distal end which is configured to be closer to the pylorus after expansion, and a central longitudinal axis which spans from its proximal end to its distal end. In an example, central longitudinal axes of expandable members can be distributed around at least 50% of the perimeter of an artificial food flow lumen. In an example, central longitudinal axes of expandable members can be distributed around at least 75% of the perimeter of an artificial food flow lumen. In an example, central longitudinal axes of expandable members can be distributed around the entire perimeter of an artificial food flow lumen.

In an example, longitudinal expandable members can collectively comprise a ring (or section of a ring) and/or arcuate colonnade which forms, encircles, encompasses, encloses, contains, and/or surrounds at least 50% of the perimeter of an artificial food flow lumen. In an example, expandable members can collectively comprise a ring (or section of a ring) and/or arcuate colonnade which forms, encircles, encompasses, encloses, contains, and/or surrounds at least 75% of the perimeter of an artificial food flow lumen. In an example, expandable members can collectively comprise a ring (or section of a ring) or arcuate colonnade which forms, encircles, encompasses, encloses, contains, and/or surrounds the entire perimeter of an artificial food flow lumen.

In an example, there can be at least one plane which contains cross-sections of the expandable members and the food flow lumen. In an example, the centroids of the cross-sections of the expandable members can be geometrically connected to form a polygon. In an example, the centroid of the cross-section of the food flow lumen is located inside this polygon. In an example, there can be at least one plane which is intersected by the expandable members and by the food flow lumen. In an example, the centers of the intersections the expandable members within this plane can be geometrically connected to form a polygon. In an example, the center of the intersection of the food flow lumen with this plane is inside this polygon. In an example, there are multiple cross-sectional planes which are intersected by the expandable members and by the food flow lumen. In an example, in each of these multiple cross-sectional planes, the centers of the intersections the expandable members within this plane can be geometrically connected to form a polygon and the center of the intersection of the food flow lumen within this plane is inside this polygon.

In an example, there can be three expandable members around a food flow lumen. In an example, connecting the cross-sectional centers of these three expandable members forms a triangle and the cross-sectional center of the food flow lumen is located inside this triangle. In an example, there can be four expandable members around a food flow lumen. In an example, connecting the cross-sectional centers of these four expandable members forms a quadrilateral and the cross-sectional center of the food flow lumen is located inside this quadrilateral. In an example, there can be six expandable members around a food flow lumen. In an example, connecting the cross-sectional centers of these six expandable members forms a hexagon and the cross-sectional center of the food flow lumen is located inside this hexagon. In an example, there can be eight expandable members around a food flow lumen. In an example, connecting the cross-sectional centers of these eight expandable members forms an octagon and the cross-sectional center of the food flow lumen is located inside this octagon. In an example, there can be more than eight expandable members. In an example, the cross-sectional centers of expandable members can be connected within a selected plane to form a polygon and the cross-sectional center of a food flow lumen within this plane is located within this polygon.

In an example, geometrically connecting the central longitudinal axes of expandable members can form a circle, oval, egg shape, or polygon around a food flow lumen. In an example, geometrically connecting the cross-sectional centers of expandable members can form a circle, oval, egg shape, or polygon around a food flow lumen. In an example, expandable members can be configured in a radially symmetric manner around the cross-sectional perimeter of a food flow lumen. In an example, expandable members can be configured in a radially asymmetric manner around the cross-sectional perimeter of a food flow lumen. In an example, the ends of longitudinal expandable members can be configured in a radially symmetric manner around a food flow lumen and the middle portions of longitudinal expandable members can be configured in an asymmetric manner around a food flow lumen. In an example, expandable members can be arranged symmetrically around a food flow lumen in a first cross-sectional plane which is nearest to the gastroesophageal junction and a second cross-sectional plane which is nearest to the pylorus, but can be arranged asymmetrically around the food flow lumen in a third cross-sectional plane which is in between the first and second cross-sectional planes.

In an example, the proximal ends or surfaces of expandable members can be connected. In an example, the distal ends or surfaces of expandable members can be connected. In an example, longitudinal expandable members can be connected along the majority of their length. In an example, expandable members can be connected by a wire, spring, ring, tube, fiber, filament, elastic band, and/or strip. In an example, expandable members can be connected by a sinusoidal wire or spring. In an example, expandable members can be pair-wise connected to each other. For example, there can be six connections between six expandable members whose central axes are arranged in a hexagon. In an example, expandable members can be connected to each other where their perimeters are closest to each other. In an example, expandable members can have generally circular cross-sectional shapes and be connected to each other along points of circumferential tangency. In an example, expandable members can be arranged in a circle and be connected by an inner ring and/or outer ring.

In an example, expandable members can have cross-sectional shapes selected from the group consisting of: a circle, an oval, an ellipse, an egg shape, a trapezoid, a keystone shape, a triangle, a rounded triangle, a convex lens shape, and hexagon. In an example, expandable members can have uniform size cross-sections. In an example, expandable members can have smaller cross sections at their end portions and larger cross sections in their middle portions. In an example, expandable members can collectively comprise an asymmetric ring of arcuate columns. In an example, expandable members in selected radial locations can have larger cross sections than those of other expandable members. In an example, expandable members near the greater curve of the stomach can have larger cross sections and columns near the lesser curve of the stomach can have smaller cross sections. In an example, a plurality of expandable members can be configured like a wagon wheel with inflatable members or chambers between flexible spokes, with a food flow lumen in the central hub position.

In an example, expandable members can have circular cross sections. In an example, expandable members can be longitudinal columns with circular cross-sections before expansion and egg-shaped cross sections after expansion. In an example, expandable members can be longitudinal with arcuate longitudinal axes. In an example, the curvatures of longitudinal axes of longitudinal expandable members can correspond to the curvatures of the stomach walls. In an example, the longitudinal axes of longitudinal expandable members can be parallel to each other prior to expansion. In an example, the longitudinal axes of longitudinal expandable members can also be parallel to the longitudinal axis of a food flow lumen. In example, longitudinal axes of expandable members can be more than 6" in length. In example, longitudinal axes of expandable members can be more than one foot in length.

In an example, the walls of expandable members can be impermeable to gas and/or fluid. In an example, the walls of the expandable members can have uniform thickness and elasticity. In an example, expandable members can be configured in a circle wherein the center-facing portions of their walls are thicker or less elastic than the outward-facing portions of their walls. In an example, expandable members that are closer to the food flow lumen can have thicker walls than expandable members that are further from the food flow lumen. In an example, expandable members that are closer to the food flow lumen can have less elastic walls than expandable members that are further from the food flow lumen. In an example, the portions of expandable member walls that are closer to the food flow lumen can be thicker than the portions of expandable member walls that are further from the food flow lumen. In an example, the portions of expandable member walls that are closer to the food flow lumen can be less elastic than the portions of expandable member walls that are further from the food flow lumen. In an example, the walls of expandable members can be thicker at the ends of the expandable members than in the middle portions of the expandable members. In an example, the walls of expandable members can be less elastic at the ends of the expandable members than in the middle portions of the expandable members.

In an example, this invention can comprise an inner set or inner ring of expandable members which are closer to a food flow lumen and an outer set or outer ring of expandable members which are further from the food flow lumen. In an example, these two sets or two rings can be concentric. In an example, these two sets or two rings can be nested. In an example, an inner set or inner ring can comprise multiple expandable members and an outer set or ring can comprise a single expandable member. In an example, an inner set or inner ring can comprise multiple longitudinal expandable members and an outer set or outer ring can comprise a single toroidal expandable member. In an example, an inner set or inner ring can comprise an arcuate colonnade of expandable members and an outer set or outer ring can comprise one or more toriodal members. In an example, the inner set or inner ring can comprise a multi-chamber expandable member and the outer set or outer ring can comprise a single-chamber member. In an example, an inner set or inner ring can comprise a single expandable member and an outer set or outer ring can comprise multiple expandable members.

In an example, expandable members or chambers in an inner set or inner ring can have one or more cross-sectional shapes selected from the group consisting of: circle, oval, ellipse, keystone, rhombus, triangle, rounded triangle, egg-shape, and torus. In an example, expandable members or chambers in an outer set or outer ring can have one or more cross-sectional shapes selected from the group consisting of: circle, oval, ellipse, keystone, rhombus, triangle, rounded triangle, egg-shape, and torus. In an example, an inner set or inner ring of expandable members can have different (e.g. more or less arcuate) cross-sectional shapes than an outer set or inner ring of expandable members. In an example, the first set of expandable members can form a circular colonnade around a central food flow lumen. In an example, the first set of expandable members can form a semi-circular colonnade around a central food flow lumen. In an example, the first set of expandable members can form an arcuate colonnade around a central food flow lumen.

In an example, an outer set or outer ring can be wider than an inner set or inner ring. In an example, an inner set or inner ring of expandable members can have different (e.g. smaller or larger) cross-sectional sizes than an outer set or inner ring of expandable members. In an example, an outer set or ring can expand more during expansion than an inner set or inner ring. In an example, an outer ring can be more elastic or have more folds (prior to expansion) than an inner ring. In an example, an inner set or inner ring of expandable members can have different (e.g. less elastic or more elastic) walls than an outer set or inner ring of expandable members.

In an example, an inner set or inner ring of expandable members can have different (e.g. thicker or thinner) walls than an outer set or inner ring of expandable members. In an example, an inner set or inner ring of expandable members can be filled with a different (e.g. more or less dense) flowable substance than an outer set or inner ring of expandable members. In an example, an inner set or inner ring of expandable members can be filled to a different (e.g. higher or lower) pressure level than an outer set or inner ring of expandable members.

In an example, there can be a first set of expandable members in an first ring (or ring segment) around a food flow lumen, a second set of expandable members in a second ring (or ring segment) around a food flow lumen, wherein members in these two sets differ in one or more aspects selected from the group consisting of: cross-sectional shape, cross-sectional size, diameter, internal pressure, length, longitudinal curvature, longitudinal shape, number of members per set or ring, type of internal flowable substance, wall elasticity, wall material, wall thickness, and wall uniformity. In an example, the first set of expandable members can be expanded before the second set of expandable members is expanded.

In an example, expandable members can be balloons. In an example, expandable members can be chambers of a multi-chamber balloon. In an example, expandable members can be expanded after insertion into a stomach by being filled with one or more flowable substances selected from the group consisting of a gas, a liquid, a gel, and a foam. In an example, expandable members can be filled separately. In an example, the interiors of expandable members can be in fluid communication with each other and expandable members can be filled together. In an example, the interiors of expandable members can be connected by one-way valves for easy removal of a flowable substance. In an example, each expandable member can have two lumens which are in fluid communication with their interiors—a first lumen which allows separate inflow or outflow of a flowable substance and a second lumen which allows common inflow or outflow of the flowable substance.

In an example, different expandable members can be filled with different flowable substances. In an example, different expandable members can be filled to different pressure levels. In an example, expandable members which are closer to a food flow lumen can be filled in a liquid and expandable members which are further from the flood flow lumen can be filled with a gas. In an example, expandable members that are closer to the food flow lumen can be filled with a more dense flowable substance or filled to a higher pressure level than expandable members that are further from the food flow lumen.

In an example, expandable members can be radially symmetric around the cross-sectional perimeter of a food flow lumen before they are expanded and can be radially asymmetric around this perimeter after they are expanded. In an example, expandable members are expanded in a primarily cross-sectional manner within the stomach. In an example, expandable members are expanded in a primarily longitudinal manner within the stomach. In an example, expandable members are expanded both longitudinally and cross-sectionally within the stomach.

In an example, one or more expandable members can be toriodal in shape. In an example, one or more expandable members can be shaped like doughnuts and (in a bit of geometric irony) help reduce the consumption of real doughnuts. In an example, a plurality of expandable members can comprise a stack of coaxial toroidal expandable members. In an example, one or more toriodal members can encircle, encompass, contain, and/or surround a central food lumen. In an example, an inner set or inner ring of expandable members can comprise one or more toriodal members. In an example, an outer set or outer ring of expandable members can comprise one or more toriodal members.

In an example, a longitudinal series or coaxial stack of toroidal expandable members can be configured to span from the esophageal junction to the pylorus. In an example, the middle portions of a longitudinal series or coaxial stack of toriodal expandable members can be expanded to occupy more than 75% of the central cross-sectional area of the stomach. In an example, the middle portions of a longitudinal series or coaxial stack of toroidal expandable members can be expanded to occupy the entire central cross-sectional area of the stomach.

In an example, a plurality of toriodal expandable members can be concentric. In an example, a plurality of toriodal expandable members can comprise a plurality of rings around a central food flow lumen. In an example, toriodal expandable members which are closer to the food flow lumen can have less wall elasticity, greater wall pressure, greater internal pressure, and/or be filled with a more dense flowable substance than toroidal expandable members which are further from the food flow lumen.

In an example, the walls of a plurality of expandable members can form a food flow lumen. In an example, the inner walls of a circle of expandable members can form a food flow lumen. In an example, the inner walls of an arcuate colonnade of longitudinal expandable members can form a food flow lumen. In an example, the inner walls of one or more toriodal expandable members can form a food flow lumen. In an example, the inner circles of a stack of coaxial toroidal expandable members can form a food flow lumen. In an example, a food flow lumen can have its own walls, but can be encircled by a plurality of expandable members. In an example, the walls of a plurality of expandable members can form more than one food flow lumen.

In an example, at least 50% of the perimeter of a food flow lumen can be encircled, encompassed, contained, and/or surrounded by a plurality of expandable members. In an example, at least 75% of the perimeter of a food flow lumen can be encircled, encompassed, contained, and/or surrounded by a plurality of expandable members. In an example, the entire perimeter of a food flow lumen can be encircled, encompassed, contained, and/or surrounded by a plurality of expandable members.

In an example, a food flow lumen can have a proximal opening which is closest to the gastroesophageal junction and a distal opening which is closest to the pylorus. In an example, a food flow lumen can have a proximal opening which is closest to the gastroesophageal junction and a distal opening which is in the small intestine. In an example, a food flow lumen can have a longitudinal axis which spans from its proximal opening to its distal opening. In an example, food flows into the proximal opening of the food flow lumen and flows out of the distal opening of the food flow lumen.

In an example, the proximal opening of a food flow lumen can be held close to the gastroesophageal junction by pressure from a plurality of expandable members. In an example, the proximal opening of a food flow lumen is contiguous to the gastroesophageal junction. In an example, the proximal opening of the food flow lumen can be held close to the gastroesophageal junction by attachment to the stomach walls and/or gastroesophageal junction. In an example, the distal opening of a food flow lumen is held close to the pylorus pressure from a plurality of expandable members. In an example, the distal opening of a food flow lumen is contiguous to the pylorus junction. In an example, the proximal opening of the food flow lumen is held close to the pylorus by attachment to the stomach walls and/or pylorus. In an example, expandable members and a food flow lumen are not attached to stomach walls, but rather are held in place by pressure from the expandable members against the stomach walls. In an alternative example, expandable members and a food flow lumen can be attached (e.g. anchored) to stomach walls at one or more locations.

In an example, a central longitudinal axis of a food flow lumen can be straight and parallel to straight central longitudinal axes of expandable members. In an example, a central longitudinal axis of a food flow lumen can be arcuate and parallel to arcuate central longitudinal axes of expandable members. In an example, the cross-sectional shape of a food flow lumen can be selected from the group consisting of: circle, oval, ellipse, egg shape, polygon, and a ring of inward-bending arcs.

In an example, a plurality of expandable members can restrict the flow of food through a stomach. In an example, a plurality of expandable members can restrict the flow of food from the gastroesophageal junction to the pylorus such that the majority of food must flow through a food flow lumen. In an example, the proximal opening of a food flow lumen can have a cross-sectional area between ½ sq. in. and 12 sq. in. In an example, the distal opening of a food flow lumen can have a cross-sectional area between ½ sq. in. and 12 sq. in. In an example, a food flow lumen can have a maximum cross-sectional area along its length of between ½ sq. in. and 12 sq. in.

In an example, there can be a first cross-sectional plane which perpendicularly intersects the longitudinal axis of a food flow lumen at a location which is in the proximal quarter of the longitudinal axis of a food flow lumen which is closest to the gastroesophageal junction, there can be a second cross-sectional plane which perpendicularly intersects the longitudinal axis of a food flow lumen at a location which is in the distal quarter of the longitudinal axis of a food flow lumen which is closest to the pylorus, and there can be a third cross-sectional plane which perpendicularly intersects the longitudinal axis of a food flow lumen at a location which is in the middle two quarters of the longitudinal axis of a food flow lumen between the first cross-sectional plane and the second cross-sectional plane. In an example, the food flow lumen can have a post-expansion first cross-sectional area as it intersects the first cross-sectional plane, second cross-sectional area as it intersects the second cross-sectional plane, and third cross-sectional area as it intersects the third cross-sectional plane. In an example, the post-expansion first, second, and third cross-sectional areas can be equal. In an example, the post-expansion third cross-sectional area can be at least 25% greater than the post-expansion first or second cross-sectional areas.

In an example, a food flow lumen can be configured to span the majority of the longitudinal axis of the stomach from the gastroesophageal junction to the pylorus. In an example, the middle portion of a food flow lumen can be configured to be closer to the lesser curve of the stomach than to the greater curve of the stomach. In an example, up to 50% of the perimeter of a food flow lumen can be comprised of the wall of the stomach, with the remaining portion of the perimeter comprised of the walls of expandable members. In an example, up to 25% of the perimeter of a food flow lumen can be comprised of the wall of the stomach, with the remaining portion of the perimeter comprised of the walls of expandable members. In an example, the entire perimeter of a food flow lumen can be comprised of the walls of expandable members.

In an example, the proximal opening of a food flow lumen can be configured to receive food flowing into the stomach from the gastroesophageal junction. In an example, the distal opening of a food flow lumen can be configured to send food flowing into the duodenum through the pylorus. In an example, a food flow lumen can be held within 3" of the gastroesophageal junction by pressure from a plurality of expandable members. In an example, a food flow lumen can be held within 3" of the pylorus by pressure from a plurality of expandable members. In an example, the proximal opening of a food flow lumen can be coaxial with the gastroesophageal junction. In an example, the distal opening of a food flow lumen can be coaxial with the pylorus. In an example, a food flow lumen can be contiguous to the gastroesophageal junction. In an example, a food flow lumen can be contiguous to the pylorus. In an example, a food flow lumen can extend through the pylorus into the duodenum.

In an example, a food flow lumen can be connected to a gastric sleeve which extends through the pylorus and into the duodenum. In an example, a food flow lumen can be attached to the gastroesophageal junction, stomach walls, and/or pylorus. In an example, a food flow lumen can be attached (e.g. anchored) to the gastroesophageal junction, stomach walls, and/or pylorus using a staple, suture, or clip. In an example, expandable members encircling, encompassing, containing, forming, and/or surrounding a food flow lumen can be attached to the gastroesophageal junction, stomach walls, and/or pylorus. In an example, expandable members can be attached (e.g. anchored) to the gastroesophageal junction, stomach walls, and/or pylorus using a staple, suture, or clip.

In an example, a plurality of expandable members and one or more food flow lumens can collectively occupy at least half of the volume of the stomach. In an example, a plurality of expandable members and one or more food flow lumens can collectively occupy at least 75% of the volume of the stomach. In an example, a plurality of expandable members and one or more food flow lumens can collectively occupy at least 95% of the volume of the stomach.

In an example, a plurality of expandable members and one or more food flow lumens can collectively span at least half of the maximum cross-sectional area of the stomach. In an example, a plurality of expandable members and one or more food flow lumens can collectively span at least 75% of the maximum cross-sectional area of the stomach. In an example, a plurality of expandable members and one or more food flow lumens can collectively span at least 95% of the maximum cross-sectional area of the stomach.

In an example, a plurality of expandable members and one or more food flow lumens can collectively span at least half of the cross-sectional area of the stomach at the mid-point between the gastroesophageal junction and the pylorus. In an example, a plurality of expandable members and one or more food flow lumens can collectively span at least 75% of the cross-sectional area of the stomach at the mid-point between the gastroesophageal junction and the pylorus. In an example, a plurality of expandable members and one or more food flow lumens can collectively span at least 95% of the cross-sectional area of the stomach at the mid-point between the gastroesophageal junction and the pylorus.

In an example, a food flow lumen can be configured to span at least 50% of the distance between the esophageal junction and the pylorus. In an example, a food flow lumen can be configured to span at least 75% of the distance between the esophageal junction and the pylorus. In an example, a food flow lumen can be configured to span at least 95% of the distance between the esophageal junction and the pylorus. In an example, a food flow lumen can be configured to span the entire distance between the esophageal junction and the pylorus.

In an example, a food flow lumen can be configured so that its proximal opening is no more than 6" away from the esophageal junction and its distal opening is no more than 6" away from the pylorus. In an example, a food flow lumen can be configured so that its proximal opening is no more than 3" away from the esophageal junction and its distal opening is no more than 3" away from the pylorus. In an example, a food flow lumen can be configured so that its proximal opening is contiguous to the esophageal junction and its distal opening is contiguous to the pylorus.

In an example, a plurality of expandable members and one or more food flow lumens can collectively direct at least half of the food flowing through a stomach through the one or more food flow lumens. In an example, a plurality of expandable members and one or more food flow lumens can collectively direct at least 75% of the food flowing through a stomach through the one or more food flow lumens. In an example, a plurality of expandable members and one or more food flow lumens can collectively direct at least 95% of the food flowing through a stomach through the one or more food flow lumens.

In an example, this device can further comprise one or more additional components selected from the group consisting of: a pumping mechanism, one or more sensors, a data processor, a data transmitter, a data receiver, and a power source. In an example, this device can be part of a system that further comprises an external remote control unit and/or wearable accessory with which it is in wireless communication.

In an example, the flow of food through a food flow lumen can be adjusted. In an example, the flow of food through the food flow lumen can be non-invasively and reversibly adjusted. In an example, the flow of food through the food flow lumen can be adjusted by pumping a flowable substance from the interior of a first set of one or more expandable members into the interior of second set of one or more expandable members. In an example, pumping a flowable substance from the interior of a first set of expandable members into the interior of a second set of expandable members can be used to adjust the flow of food through the food flow lumen by adjusting the size and/or shape of the food flow lumen. In an example, pumping a flowable substance from the interior of a first set of expandable members into the interior of a second set of expandable members can be used to adjust the cross-sectional size of the food flow lumen.

In an example, this device can further comprise a pumping mechanism which pumps a flowable substance from the interior of a first expandable member into the interior of a second expandable member, wherein this pump is selected from the group consisting of: Archimedes pump, axial pump, balloon pump, centripetal/fugal pump, ciliary motion pump, compressive pump, continuous flow pump, diaphragm pump, elastomeric pump, electromagnetic field pump, electromechanical pump, electroosmotic pump, gear pump, hybrid pulsatile and continuous pump, hydrodynamically-levitated pump, hydroelastic pump, impedance pump, longitudinal-membrane-wave pump, magnetic flux pump, Micro Electro Mechanical System (MEMS) pump, peristaltic pump, piston pump, pump with a helical impeller, pump with a parallel-axis impeller, pump with a perpendicular-axis impeller, pump with a series of circumferentially-compressive members, pump with an expansion chamber and one-way valve, pump with an impeller with multiple vans, fins, and/or blades, pump with electromagnetically-driven magnetic impeller, rotary pump, and worm pump.

In an example, the flow of food through a food flow lumen can be non-invasively and reversibly adjusted by an internal pumping mechanism which is in wireless communication with an external remote control unit. In an example, the flow of food through the food flow lumen can be non-invasively and reversibly adjusted by an internal pumping mechanism which is in wireless communication with an external wearable accessory. In an example, the flow of food through the food flow lumen can be non-invasively and reversibly adjusted by an internal pumping mechanism based on data from one or more internal sensors. In an example, a pumping mechanism can automatically change the cross-sectional size of a food flow lumen based on food consumption data from one or more sensors. In an example, a pumping mechanism can automatically change the cross-sectional size of a food flow lumen when a person consumes an unhealthy type and/or quantity of food based on data from one or more sensors.

In an example, this device can further comprise a wireless data receiver and transmitter which is in wireless communication with an external remote control unit. In an example, the cross-sectional size and/or shape of a food flow lumen can be reversibly and post-operatively adjusted by a remote control unit which activates a pumping mechanism to pump a flowable substance from one expandable member to another. In an example, the cross-sectional size and/or shape of a food flow lumen can be post-operatively, non-invasively, and reversibly adjusted by wireless communication from an external remote control unit which triggers a pumping mechanism to pump a flowable substance from one expandable member to another.

In an example, this device can be part of a system which further comprises a wearable accessory. In an example, a wearable accessory can be selected from the group consisting of: a wrist band, a watch, an arm band, electronically-functional eyewear, smart clothing, electronically-functional earware, a necklace or pendant, electronically-functional tattoo and/or patch, and oral appliance or dental implant. In an example, this wearable accessory can be in wireless communication with a pumping mechanism which pumps a flowable substance from one expandable member to another. In an example, the cross-sectional size and/or shape of the food flow lumen can be remotely adjustable via wireless communication between an external wearable accessory and an internal pumping mechanism which pumps a flowable substance from one expandable member to another. In an example, a pumping mechanism can be triggered manually. In an example, a pumping mechanism can be triggered automatically based on food consumption detected by the wearable accessory. In an example, the cross-sectional size and/or shape of the food flow lumen can be reduced when a person eats an unhealthy type and/or amount of food.

In an example, this device can further comprise one or more implanted sensors. In an example, one or more sensors can be in wireless communication with a pumping mechanism which pumps a flowable substance from one expandable member to another. In an example, the cross-sectional size and/or shape of the food flow lumen can be automatically adjusted based on data received from one or more sensors. In an example, the pumping mechanism can be triggered automatically based on data from one or more sensors. In an example, the cross-sectional size and/or shape of the food flow lumen can be reduced when one or more sensors indicate that a person is eating an unhealthy type and/or amount of food.

In an example, data from one or more sensors can identify food as unhealthy by identifying food that is high in simple carbohydrates, food that is high in simple sugars, food that is high in saturated or trans fat, fried food, food that is high in Low Density Lipoprotein (LDL), and/or food that is high in sodium. In an example, data from one or more sensors can be used to identify one or more nutrients selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, data from one or more sensors can be used to identify one or more nutrients selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a selected type of carbohydrate, class of carbohydrates, or all carbohydrates; a selected type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a selected type of fat, class of fats, or all fats; fatty acids, monounsaturated fat, polyunsaturated fat, saturated fat, trans fat, and unsaturated fat; a selected type of cholesterol, a class of cholesterols, or all cholesterols; Low Density Lipoprotein (LDL), High Density Lipoprotein (HDL), Very Low Density Lipoprotein (VLDL), and triglycerides; a selected type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a selected type of fiber, a class of fiber, or all fiber; dietary fiber, insoluble fiber, soluble fiber, and cellulose; a specific sodium compound, a class of sodium compounds, and all sodium compounds; salt; a selected type of meat, a class of meats, and all meats; a selected type of vegetable, a class of vegetables, and all vegetables; a selected type of fruit, a class of fruits, and all fruits; a selected type of grain, a class of grains, and all grains; high-carbohydrate food, high-sugar food, high-fat food, fried food, high-cholesterol food, high-protein food, high-fiber food, and high-sodium food.

In an example, a sensor can be a chemical sensor for detecting food consumption and/or identifying food type. In an example, a chemical sensor can be in fluid communication with the food flow lumen and/or the interior of the person's stomach. In an example, a sensor can be a light energy sensor for detecting food consumption and/or identifying food type. In an example, a chemical sensor can be in optical communication with the food flow lumen and/or the interior of the person's stomach. In an example, this light energy sensor can be a spectroscopic sensor. In an example, a sensor can be a motion sensor for detecting food consumption. In an example, a sensor can be a sonic energy sensor for identifying food consumption. In an example, a sensor can be an electromagnetic energy sensor for detecting food consumption and/or identifying food type.

In an example, this device and system can further comprise one or more sensors selected from the group consisting of: motion sensor, inertial sensor, single axis, biaxial, or multi-axial accelerometer, kinematic sensor, gyroscope, tilt sensor, inclinometer, vibration sensor, bend sensor, goniometer, strain gauge, stretch sensor, pressure sensor, force sensor, flow sensor, blood flow monitor, blood pressure monitor, microcantilever sensor, microfluidic sensor, and manometer.

In an example, this device and system can further comprise one or more sensors selected from the group consisting of: electromagnetic energy sensor, electromagnetic conductivity sensor, electromagnetic resistance sensor, variable resistance sensor, electromagnetic impedance sensor, variable impedance sensor, amp meter, voltmeter, magnetometer, magnetic field sensor, compass, radio frequency (RF) sensor, Hall-effect sensor, piezocapacitive sensor, piezoelectric sensor, electrogoniometer, electrochemical sensor, electromagnetic electrode, electroosmotic sensor, electrophoresis sensor, electroporation sensor, neural impulse monitor and/or sensor, neurosensor, action potential sensor, electrocardiography (ECG) or EKG sensor and/or monitor, electroencephalography (EEG) sensor and/or monitor, electromagnetic brain activity sensor and/or monitor, electrogastrography (EGG) sensor and/or monitor, electromyography (EMG) sensor and/or monitor, electromagnetic muscle activity sensor, electrooculography (EOG) sensor and/or monitor, hemoencephalography (HEG) monitor, micro electromechanical system (MEMS) sensor, cardiac function monitor, cardiotachometer, cardiovascular monitor, heart rate monitor, heart sensor, pulse monitor, pulmonary function and/or respiratory function monitor, respiration rate monitor, tidal volume sensor, spirometry monitor, pneumography sensor, and breathing monitor.

In an example, this device and system can further comprise one or more sensors selected from the group consisting of: light energy sensor, electro-optical sensor, infrared sensor, laser sensor, light intensity sensor, optical sensor, optoelectronic sensor, photochemical sensor, photoelectric sensor, photometer, ultraviolet light sensor, thermoluminescence sensor, variable-translucence sensor, photoplethysmography (PPG) sensor, chemiluminescence sensor, fluorescence sensor, camera, video recorder, spectroscopic sensor, light-spectrum-analyzing sensor, color sensor, spectral analysis sensor, spectrometry sensor, spectrophotometric sensor, spectroscopy sensor, near-infrared, infrared, ultraviolet, or white light spectroscopy sensor, mass spectrometry sensor, Raman spectroscopy sensor, ion mobility spectroscopic sensor, backscattering spectrometry sensor, chromatography sensor, optical glucose sensor, gas chromatography sensor, and analytical chromatography sensor.

In an example, this device and system can further comprise one or more sensors selected from the group consisting of: sound sensor, sonic energy sensor, microphone, chewing and/or swallowing monitor, ambient sound sensor or monitor, ultrasound sensor, Doppler ultrasound sensor, audiometer, temperature and/or thermal energy sensor, thermistor, thermometer, thermopile, body temperature sensor, ambient temperature sensor, biochemical sensor, amino acid sensor, artificial olfactory sensor, blood glucose monitor, blood oximeter, body fat sensor, caloric expenditure monitor, caloric intake monitor, capnography sensor, carbon dioxide sensor, carbon monoxide sensor, cerebral oximetry monitor, chemical sensor, chemiresistor sensor, chemoreceptor sensor, cholesterol sensor, cutaneous oxygen monitor, ear oximeter, food composition analyzer, food identification sensor, food consumption monitor, caloric intake monitor, gas composition sensor, glucometer, glucose monitor, humidity sensor, hydration sensor, laboratory-on-a-chip, microbial sensor, moisture sensor, osmolality sensor, oximeter, oximetry sensor, oxygen consumption monitor, oxygen level monitor or sensor, oxygen saturation monitor, pH level sensor, porosity sensor, pulse oximeter, skin moisture sensor, sodium sensor, tissue oximetry sensor, and tissue saturation oximeter.

In an example, this device can further comprise a data processor which receives data from the one or more sensors. In an example, this data processor can analyze this data to detect food consumption and identify the types and/or amounts of food consumed. In an example, this device can further comprise a data transmitter and receiver. In an example, a data transmitter can transmit data from one or more sensors to an external and/or remote data processor which analyzes this data to detect food consumption and identify the types and/or amounts of food consumed. In an example, a data receiver can receive data from a remote control unit to trigger activation of the pumping mechanism to change the cross-sectional size and/or shape of the food flow lumen. In an example, this device can further comprise a power source (such as a battery). In an example, this device can further comprise a power transducer which generates electricity from the kinetic energy or body motion. In an example, energy harvested from kinetic energy can be used to recharge a power source (such as a battery).

In an example, this device can further comprise at least one pumping mechanism which pumps a flowable substance from the interior of one expandable member into the interior of another expandable member. In an example, this device can further comprise at least one pumping mechanism which pumps a flowable substance from the interior of one or more expandable members in an inner set or inner ring of such members into the interior of one or more expandable members in an outer set or outer ring of such members. In an example, such pumping can change the cross-sectional size and/or shape of a central food flow lumen. In an example, this pumping can be triggered manually through the use of an external remote control unit. In an example, this pumping can be triggered automatically based on data from one or more implanted sensors. In an example, this pumping can be triggered automatically when this data indicates that the person is consuming an unhealthy type and/or amount of food.

In an example, this invention can be embodied in a device and system comprising: an expandable intragastric food flow lumen device comprising: (a) at least three expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

In an example, this invention can be embodied in a device and system comprising: an expandable intragastric food flow lumen device comprising: (a) an expandable multi-chambered member with at least three expandable chambers which is configured to be inserted into and expanded within a person's stomach; wherein these expandable chambers are expanded by being filled with one or more flowable substances selected from the group consisting of a gas, a liquid, a gel, and a foam; wherein each expandable chamber has a proximal surface which is configured to be closer to the gastroesophageal junction and a distal surface which is configured to be closer to the pylorus; wherein each expandable chamber has a central axis which spans from its proximal surface to its distal surface; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable chambers; wherein the points where the central axes of the expandable chambers intersect this plane can be geometrically connected to form a polygon; and wherein the point where the central axis of the food flow lumen intersects this plane is located inside this polygon.

In an example, this invention can be embodied in a device and system comprising: an expandable intragastric food flow lumen device comprising: (a) at least three expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the expandable members collectively encircle, encompass, enclose, contain, and/or surround at least 50% of the perimeter of the artificial food flow lumen.

In an example, this invention can be embodied in a device and system comprising: an expandable intragastric food flow lumen device comprising: (a) an expandable multi-chambered member with at least three expandable chambers which is configured to be inserted into and expanded within a person's stomach; wherein these expandable chambers are expanded by being filled with one or more flowable substances selected from the group consisting of a gas, a liquid, a gel, and a foam; wherein each expandable chamber has a proximal surface which is configured to be closer to the gastroesophageal junction and a distal surface which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the expandable chambers collectively encircle, encompass, enclose, contain, and/or surround at least 50% of the perimeter of the artificial food flow lumen.

In an example, this invention can be embodied in a device and system comprising: a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; wherein each longitudinal expandable member has a central longitudinal axis which spans from its proximal end to its distal end; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central longitudinal axis which spans from its proximal opening to its distal opening; wherein there is at least one cross-sectional plane of this device which is intersected by the central longitudinal axis of the food flow lumen and the central longitudinal axes of the longitudinal expandable members; wherein the points where the central longitudinal axes of the longitudinal expandable members intersect this cross-sectional plane can be geometrically connected to form a polygon; and wherein the point where the central longitudinal axis of the food flow lumen intersects this cross-sectional plane is located inside this polygon.

In an example, this invention can be embodied in a device and system comprising: a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; wherein each longitudinal expandable chamber has a central longitudinal axis which spans from its proximal end to its distal end; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central longitudinal axis which spans from its proximal opening to its distal opening; wherein there is at least one cross-sectional plane of this device which is intersected by the central longitudinal axis of the food flow lumen and the central longitudinal axes of the longitudinal expandable chambers; wherein the points where the central longitudinal axes of the longitudinal expandable chambers intersect this cross-sectional plane can be geometrically connected to form a polygon; and wherein the point where the central longitudinal axis of the food flow lumen intersects this cross-sectional plane is located inside this polygon.

In an example, this invention can be embodied in a device and system comprising: a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable members collectively encircle, encompass, enclose, contain, and/or surround at least 50% of the perimeter of the artificial food flow lumen.

In an example, this invention can be embodied in a device and system comprising: a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable chambers collectively encircle, encompass, enclose, contain, and/or surround at least 50% of the perimeter of the artificial food flow lumen.

In an example, this invention can be embodied in a device and system comprising: a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable members collectively comprise a ring of columns and/or an arcuate colonnade which encircles, encompasses, encloses, contains, and/or surrounds at least 50% of the perimeter of the artificial food flow lumen.

In an example, this invention can be embodied in a device and system comprising: a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable chambers collectively comprise a ring of columns and/or an arcuate colonnade which encircles, encompasses, encloses, contains, and/or surrounds at least 50% of the perimeter of the artificial food flow lumen.

In an example, this invention can be embodied in a device and system comprising: a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable members collectively comprise an inner ring or ring section and an outer ring or ring section which each encircle, encompass, enclose, contain, and/or surround at least 50% of the perimeter of the artificial food flow lumen.

In an example, this invention can be embodied in a device and system comprising: a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable chambers collectively comprise an inner ring or ring section and an outer ring or ring section which each encircle, encompass, enclose, contain, and/or surround at least 50% of the perimeter of the artificial food flow lumen.

In an example, this invention can be embodied in a device and system comprising: a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable members are radially distributed around at least 50% of the perimeter of the artificial food flow lumen.

In an example, this invention can be embodied in a device and system comprising: a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable chambers are radially distributed around at least 50% of the perimeter of the artificial food flow lumen.

In an example, this invention can be embodied in a device and system comprising: a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; wherein each longitudinal expandable member has a central longitudinal axis which spans from its proximal end to its distal end; and (b) an artificial food flow lumen; wherein this food flow lumen has a proximal opening which is configured to be closer to the gastroesophageal junction and a distal opening which is configured to be closer to the pylorus; wherein this food flow lumen has a central longitudinal axis which spans from its proximal opening to its distal opening; wherein food flows into the proximal opening and out of the distal opening; and wherein the central longitudinal axis of the food flow lumen is straight parallel or arcuately parallel to the central longitudinal axes of the longitudinal expandable members.

In an example, this invention can be embodied in a device and system comprising: a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; wherein each longitudinal expandable chamber has a central longitudinal axis which spans from its proximal end to its distal end; and (b) an artificial food flow lumen; wherein this food flow lumen has a proximal opening which is configured to be closer to the gastroesophageal junction and a distal opening which is configured to be closer to the pylorus; wherein this food flow lumen has a central longitudinal axis which spans from its proximal opening to its distal opening; wherein food flows into the proximal opening and out of the distal opening; and wherein the central longitudinal axis of the food flow lumen is straight parallel or arcuately parallel to the central longitudinal axes of the longitudinal expandable chambers.

In an example, this invention can be embodied in a device and system comprising: a multi-columnar expandable intragastric food flow lumen device comprising: at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; and wherein the walls of these longitudinal expandable members collectively form an artificial food flow lumen with a proximal opening which is configured to be closer to the gastroesophageal junction and a distal opening which is configured to be closer to the pylorus.

In an example, this invention can be embodied in a device and system comprising: a multi-columnar expandable intragastric food flow lumen device comprising: an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; and wherein the walls of the expandable multi-chambered member form an artificial food flow lumen with a proximal opening which is configured to be closer to the gastroesophageal junction and a distal opening which is configured to be closer to the pylorus.

In an example, this invention can be embodied in a device and system comprising: an expandable intragastric food flow lumen device comprising: one or more toroidal expandable members; wherein these one or more toroidal expandable members are configured to be inserted into and expanded within a person's stomach; wherein these one or more toroidal expandable members are expanded by being filled with one or more flowable substances selected from the group consisting of a gas, a liquid, a gel, and a foam; and wherein the walls of these one or more toroidal expandable members form an artificial food flow lumen with a proximal opening which is configured to be closer to the gastroesophageal junction and a distal opening which is configured to be closer to the pylorus.

In an example, this invention can be embodied in a device and system comprising: an expandable intragastric food flow lumen device comprising: an expandable multi-chambered member with one or more expandable toroidal expandable chambers which is configured to be inserted into and expanded within a person's stomach; wherein these one or more toroidal expandable chambers are expanded by being filled with one or more flowable substances selected from the group consisting of a gas, a liquid, a gel, and a foam; and wherein this expandable multi-chambered member forms an artificial food flow lumen with a proximal opening which is configured to be closer to the gastroesophageal junction and a distal opening which is configured to be closer to the pylorus.

FIGS. 1 through 4 show an example of this invention which is embodied as an expandable intragastric food flow lumen device comprising: (a) a plurality of expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) a food flow lumen; wherein this food flow lumen has a proximal opening which is configured to be closer to the gastroesophageal junction and a distal opening which is configured to be closer to the pylorus;

wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

FIG. 1 shows a side view of this device after it has been inserted into and expanded within a stomach. In order to show anatomical context for this device, FIG. 1 also shows a cross-sectional side view of the gastroesophageal junction 101, stomach 102, pylorus 103, and duodenum 104. FIG. 2 shows a circular cross-sectional view of this same device near the gastroesophageal junction. FIG. 3 shows a circular cross-sectional view of this same device near the middle of the stomach (between the gastroesophageal junction and the pylorus). FIG. 4 shows a circular cross-sectional view of this same device near the pylorus. FIGS. 1 through 4 show that this device has a plurality of longitudinal expandable members (105, 106, 107, 108, 109, and 110) which encircle, encompass, form, contain, and surround a central food lumen 201. Relevant examples and variations which are discussed elsewhere in this detailed description of the figures also apply to this example shown in FIGS. 1 through 4.

In FIGS. 1 through 4, a plurality of expandable members (105, 106, 107, 108, 109, and 110) are shown after they have been inserted into stomach 102 through the esophagus and expanded within stomach 102 by being filled with a flowable substance. At a later time, this flowable substance can be removed from these expandable members and these expandable members can be removed from the stomach. In the meantime, this device is left within the stomach (for months or years) to restrict and/or control food intake. These figures show an example of a device wherein expandable members restrict the flow of food through a stomach and/or the amount of food which the stomach can contain. These figures show an example of a device wherein expandable members (105, 106, 107, 108, 109, and 110) restrict the flow of food through the stomach to food flow lumen 201 and wherein this food flow lumen is encircled, encompassed, contained, formed, and/or surrounded by expandable members (105, 106, 107, 108, 109, and 110).

FIGS. 1 through 4 show an example of this device wherein a plurality of expandable members (105, 106, 107, 108, 109, and 110) are connected to each other. In this example, a plurality of expandable members are pair-wise connected and their central axes are arranged in a circular or polygonal formation. In this example, expandable members are longitudinal expandable members. In this example, there are six expandable members. In this example, the walls of a plurality of expandable members form a food flow lumen. In this example, the walls of a plurality of expandable members are connected and their central axes are arranged in a circular or polygonal formation which forms a central food flow lumen. In this example, expandable members are arranged in a circle and the center-facing portions of the walls of these expandable members collectively form a food flow lumen.

FIGS. 1 through 4 show an example of this device wherein expandable members are distributed around at least 50% of the perimeter of a food flow lumen. In this example, wherein expandable members are distributed around at least 75% of the perimeter of a food flow lumen. Also, in this example, expandable members are distributed around the entire perimeter of a food flow lumen. In this example, expandable members form a circle or egg shape around a food flow lumen. In this example, expandable members collectively comprise a ring of arcuate columns (or colonnade) around a food flow lumen. In this example, expandable members collectively comprise a ring of arcuate columns (or colonnade) with a food flow lumen in the middle.

FIGS. 1 through 4 show an example of this device wherein expandable members collectively comprise a ring (or section of a ring) which forms, encircles, encompasses, encloses, contains, and/or surrounds at least 50% of the perimeter of an artificial food flow lumen. In this example, expandable members collectively comprise a ring (or section of a ring) which forms, encircles, encompasses, encloses, contains, and/or surrounds at least 75% of the perimeter of an artificial food flow lumen. Also, in this example, expandable members collectively comprise a ring (or section of a ring) which forms, encircles, encompasses, encloses, contains, and/or surrounds the entire perimeter of an artificial food flow lumen.

FIGS. 1 through 4 show an example of this device wherein expandable members are longitudinal expandable members. In this example, a longitudinal expandable member has a proximal end which is configured to be closer to the gastroesophageal junction after expansion, a distal end which is configured to be closer to the pylorus after expansion, and a central longitudinal axis which spans from its proximal end to its distal end. These figures also show an example wherein the central longitudinal axes of expandable members are distributed around at least 50% of the perimeter of an artificial food flow lumen. Also, in this example, central longitudinal axes of expandable members are distributed around at least 75% of the perimeter of an artificial food flow lumen. Also, in this example, central longitudinal axes of expandable members are distributed around the entire perimeter of an artificial food flow lumen.

FIGS. 1 through 4 show an example of a device wherein longitudinal expandable members collectively comprise a ring (or section of a ring) and/or arcuate colonnade which forms, encircles, encompasses, encloses, contains, and/or surrounds at least 50% of the perimeter of an artificial food flow lumen. In this example, expandable members collectively comprise a ring (or section of a ring) and/or arcuate colonnade which forms, encircles, encompasses, encloses, contains, and/or surrounds at least 75% of the perimeter of an artificial food flow lumen. Also, in this example, expandable members collectively comprise a ring (or section of a ring) or arcuate colonnade which forms, encircles, encompasses, encloses, contains, and/or surrounds the entire perimeter of an artificial food flow lumen.

FIGS. 1 through 4 show an example of a device wherein there is at least one plane which contains cross-sections of the expandable members and the food flow lumen. In this example, the centroids of the cross-sections of the expandable members can be geometrically connected to form a polygon and the centroid of the cross-section of the food flow lumen is located inside this polygon. In this example, there is at least one plane which is intersected by the expandable members and by the food flow lumen. In this example, the centers of the intersections the expandable members within this plane can be geometrically connected to form a polygon and the center of the intersection of the food flow lumen with this plane is inside this polygon. In this example, there are multiple cross-sectional planes which are intersected by the expandable members and by the food flow lumen. In this example, in each of these multiple cross-sectional planes, the centers of the intersections the expandable members within this plane can be geometrically connected to form a polygon and the center of the intersection of the food flow lumen within this plane is inside this polygon.

FIGS. 1 through 4 show an example of this device wherein connecting the cross-sectional centers of these six expandable members forms a hexagon and the cross-sectional center of the food flow lumen is located inside this hexagon. In this example, the cross-sectional centers of expandable members can be connected within a selected plane to form a polygon and the cross-sectional center of a food flow lumen within this plane is located within this polygon. In this example, geometrically connecting the central longitudinal axes of expandable members forms a circle or egg shape.

FIGS. 1 through 4 show an example of this device wherein expandable members are configured in a radially asymmetric manner around the cross-sectional perimeter of a food flow lumen. In this example, the ends of longitudinal expandable members are configured in a radially symmetric manner around a food flow lumen and the middle portions of longitudinal expandable members are configured in an asymmetric manner around a food flow lumen. In this example, expandable members are arranged symmetrically around a food flow lumen in a first cross-sectional plane which is nearest to the gastroesophageal junction and a second cross-sectional plane which is nearest to the pylorus, but are arranged asymmetrically around the food flow lumen in a third cross-sectional plane which is between the first and second cross-sectional planes.

FIGS. 1 through 4 show an example of this device wherein longitudinal expandable members are connected along the majority of their length. In this example, expandable members are pair-wise connected to each other and there are six connections between them. In this example, six expandable members have central axes which are arranged in a hexagon. In this example, expandable members are connected to each other where their perimeters are closest to each other. In this example, expandable members have generally circular cross-sectional shapes and are connected to each other along points of circumferential tangency.

FIGS. 1 through 4 show an example of this device wherein expandable members have cross-sectional shapes selected from the group consisting of: a circle, an oval, an ellipse, an egg shape, a trapezoid, a keystone shape, a triangle, a rounded triangle, a convex lens shape, and hexagon. In this example, expandable members have smaller cross sections at their end portions and larger cross sections in their middle portions. In this example, expandable members collectively comprise an asymmetric ring of arcuate columns. In this example, expandable members in selected radial locations have larger cross sections than those of other expandable members. In this example, expandable members near the greater curve of the stomach have larger cross sections and those near the lesser curve of the stomach have smaller cross sections.

FIGS. 1 through 4 show an example of this device wherein expandable members have circular cross sections. In this example, expandable members are arcuate longitudinal columns with circular cross-sections before expansion and egg-shaped cross sections after expansion. In this example, expandable members are longitudinal with arcuate longitudinal axes. In this example, the curvatures of longitudinal axes of longitudinal expandable members correspond to the curvatures of the stomach walls. In this example, longitudinal axes of expandable members are more than 6" in length.

In the example shown in FIGS. 1 through 4, the walls of expandable members are impermeable to gas and/or fluid. In this example, expandable members are configured in a circle wherein the center-facing portions of their walls are thicker or less elastic than the outward-facing portions of their walls. In this example, expandable members that are closer to the food flow lumen have less elastic walls than expandable members that are further from the food flow lumen. In this example, the portions of expandable member walls that are closer to the food flow lumen are less elastic than the portions of expandable member walls that are further from the food flow lumen. In this example, the walls of expandable members are less elastic at the ends of the expandable members than in the middle portions of the expandable members.

FIGS. 1 through 4 show an example of this device wherein expandable members are balloons. In another example, expandable members can be chambers of a multi-chamber balloon. In this example, expandable members have been expanded after insertion into a stomach by being filled with one or more flowable substances selected from the group consisting of a gas, a liquid, a gel, and a foam. In an example, different expandable members can be filled with different flowable substances or filled to different pressure levels.

FIGS. 1 through 4 show an example of this device wherein the walls of a plurality of expandable members form a food flow lumen. In this example, the inner walls of a circle of expandable members form a food flow lumen. In this example, the inner walls of an arcuate colonnade of longitudinal expandable members form a food flow lumen. In this example, at least 50% of the perimeter of a food flow lumen is encircled, encompassed, contained, and/or surrounded by a plurality of expandable members. Also, in this example, at least 75% of the perimeter of a food flow lumen is encircled, encompassed, contained, and/or surrounded by a plurality of expandable members. Also, in this example, the entire perimeter of a food flow lumen is encircled, encompassed, contained, and/or surrounded by a plurality of expandable members.

FIGS. 1 through 4 show an example of a device wherein a food flow lumen has a proximal opening which is closest to the gastroesophageal junction and a distal opening which is closest to the pylorus. In this example, a food flow lumen has a proximal opening which is closest to the gastroesophageal junction and a distal opening which is in the small intestine. In this example, a food flow lumen has a longitudinal axis which spans from its proximal opening to its distal opening. In this example, food flows into the proximal opening of the food flow lumen and flows out of the distal opening of the food flow lumen.

FIGS. 1 through 4 show an example of this device wherein the proximal opening of a food flow lumen is held close to the gastroesophageal junction by pressure from a plurality of expandable members. In this example, the proximal opening of a food flow lumen is contiguous to the gastroesophageal junction. In this example, the proximal opening of the food flow lumen is held close to the gastroesophageal junction by attachment to the stomach walls and/or gastroesophageal junction. In this example, the distal opening of a food flow lumen is held close to the pylorus pressure from a plurality of expandable members. FIGS. 1 through 4 show an example of this device wherein expandable members and a food flow lumen are not attached to stomach walls, but rather are held in place by pressure from the expandable members against the stomach walls. In an alternative example, expandable members and a food flow lumen can be attached (e.g. anchored) to stomach walls at one or more locations.

FIGS. 1 through 4 show an example of this device wherein a central longitudinal axis of a food flow lumen is arcuate and parallel to arcuate central longitudinal axes of expandable members. In this example, the cross-sectional shape of a food flow lumen is a ring of inward-bending arcs. In this example, a plurality of expandable members restrict the flow of food through a stomach. In this example, a plurality of expandable members restrict the flow of food from the gastroesophageal junction to the pylorus such that the majority of food must flow through a food flow lumen. In this example, the proximal opening of a food flow lumen has a cross-sectional area between ½ sq. in. and 12 sq. in.

FIGS. 1 through 4 show an example of this device wherein there is a first cross-sectional plane which perpendicularly intersects the longitudinal axis of a food flow lumen at a location which is in the proximal quarter of the longitudinal axis of a food flow lumen which is closest to the gastroesophageal junction, there is a second cross-sectional plane which perpendicularly intersects the longitudinal axis of a food flow lumen at a location which is in the distal quarter of the longitudinal axis of a food flow lumen which is closest to the pylorus, and there is a third cross-sectional plane which perpendicularly intersects the longitudinal axis of a food flow lumen at a location which is in the middle two quarters of the longitudinal axis of a food flow lumen between the first cross-sectional plane and the second cross-sectional plane. Further, the food flow lumen has a post-expansion first cross-sectional area as it intersects the first cross-sectional plane, a second cross-sectional area as it intersects the second cross-sectional plane, and a third cross-sectional area as it intersects the third cross-sectional plane. Further, in this example, the post-expansion third cross-sectional area is at least 25% greater than the post-expansion first or second cross-sectional areas.

FIGS. 1 through 4 show an example of this device wherein a food flow lumen is configured to span the majority of the longitudinal axis of the stomach from the gastroesophageal junction to the pylorus. In this example, the middle portion of a food flow lumen is configured to be closer to the lesser curve of the stomach than to the greater curve of the stomach. In this example, the entire perimeter of a food flow lumen is comprised of the walls of expandable members.

FIGS. 1 through 4 show an example of this device wherein the proximal opening of a food flow lumen is configured to receive food flowing into the stomach from the gastroesophageal junction. Also, in this example, the distal opening of the food flow lumen is configured to send food flowing into the duodenum through the pylorus. In this example, the food flow lumen is held within 3" of the gastroesophageal junction and the distal end of the food flow lumen is held within 3" of the pylorus by pressure from a plurality of expandable members. In this example, the proximal opening of a food flow lumen is coaxial with the gastroesophageal junction and the distal opening of the food flow lumen is coaxial with the pylorus.

FIGS. 1 through 4 show an example of this device wherein a plurality of expandable members and one or more food flow lumens collectively occupy at least half of the volume of the stomach. Also, in this example, a plurality of expandable members and one or more food flow lumens collectively occupy at least 75% of the volume of the stomach. Also, in this example, a plurality of expandable members and one or more food flow lumens collectively occupy at least 95% of the volume of the stomach. FIGS. 1 through 4 also show an example wherein a plurality of expandable members and one or more food flow lumens collectively span at least half of the maximum cross-sectional area of the stomach. Also, in this example, a plurality of expandable members and one or more food flow lumens collectively span at least 75% of the maximum cross-sectional area of the stomach. Also, in this example, a plurality of expandable members and one or more food flow lumens collectively span at least 95% of the maximum cross-sectional area of the stomach.

FIGS. 1 through 4 show an example of this device wherein a plurality of expandable members and one or more food flow lumens collectively span at least half of the cross-sectional area of the stomach at the mid-point between the gastroesophageal junction and the pylorus. In this example, a plurality of expandable members and one or more food flow lumens collectively span at least 75% of the cross-sectional area of the stomach at the mid-point between the gastroesophageal junction and the pylorus. Also, in this example, a plurality of expandable members and one or more food flow lumens collectively span at least 95% of the cross-sectional area of the stomach at the mid-point between the gastroesophageal junction and the pylorus.

FIGS. 1 through 4 show an example of this device wherein a food flow lumen is configured to span at least 50% of the distance between the esophageal junction and the pylorus. In this example, a food flow lumen is configured to span at least 75% of the distance between the esophageal junction and the pylorus. Also, in this example, a food flow lumen is configured to span at least 95% of the distance between the esophageal junction and the pylorus. FIGS. 1 through 4 show an example of this device wherein a food flow lumen is configured so that its proximal opening is no more than 3" away from the esophageal junction and its distal opening is no more than 3" away from the pylorus.

FIGS. 1 through 4 show an example of this device wherein a plurality of expandable members and one or more food flow lumens collectively direct at least half of the food flowing through a stomach through the one or more food flow lumens. In this example, a plurality of expandable members and one or more food flow lumens collectively direct at least 75% of the food flowing through a stomach through the one or more food flow lumens. In an example, a plurality of expandable members and one or more food flow lumens collectively direct at least 95% of the food flowing through a stomach through the one or more food flow lumens.

In an example, the device shown in FIGS. 1 through 4 can further comprise one or more additional components selected from the group consisting of: a pumping mechanism, one or more sensors, a data processor, a data transmitter, a data receiver, and a power source. In an example, the device in FIGS. 1 through 4 can also be part of a system that further comprises an external remote control unit and/or wearable accessory with which it is in wireless communication.

FIGS. 1 through 4 show an example of an expandable intragastric food flow lumen device comprising: (a) at least three expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

FIGS. 1 through 4 show an example of an expandable intragastric food flow lumen device comprising: (a) an expandable multi-chambered member with at least three expandable chambers which is configured to be inserted into and expanded within a person's stomach; wherein these expandable chambers are expanded by being filled with one or more flowable substances selected from the group consisting of a gas, a liquid, a gel, and a foam; wherein each expandable chamber has a proximal surface which is configured to be closer to the gastroesophageal junction and a distal surface which is configured to be closer to the pylorus; wherein each expandable chamber has a central axis which spans from its proximal surface to its distal surface; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable chambers; wherein the points where the central axes of the expandable chambers intersect this plane can be geometrically connected to form a polygon; and wherein the point where the central axis of the food flow lumen intersects this plane is located inside this polygon.

FIGS. 1 through 4 show an example of an expandable intragastric food flow lumen device comprising: (a) at least three expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the expandable members collectively encircle, encompass, enclose, contain, and/or surround at least 50% of the perimeter of the artificial food flow lumen.

FIGS. 1 through 4 show an example of an expandable intragastric food flow lumen device comprising: (a) an expandable multi-chambered member with at least three expandable chambers which is configured to be inserted into and expanded within a person's stomach; wherein these expandable chambers are expanded by being filled with one or more flowable substances selected from the group consisting of a gas, a liquid, a gel, and a foam; wherein each expandable chamber has a proximal surface which is configured to be closer to the gastroesophageal junction and a distal surface which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the expandable chambers collectively encircle, encompass, enclose, contain, and/or surround at least 50% of the perimeter of the artificial food flow lumen.

FIGS. 1 through 4 show an example of a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; wherein each longitudinal expandable member has a central longitudinal axis which spans from its proximal end to its distal end; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central longitudinal axis which spans from its proximal opening to its distal opening; wherein there is at least one cross-sectional plane of this device which is intersected by the central longitudinal axis of the food flow lumen and the central longitudinal axes of the longitudinal expandable members; wherein the points where the central longitudinal axes of the longitudinal expandable members intersect this cross-sectional plane can be geometrically connected to form a polygon; and wherein the point where the central longitudinal axis of the food flow lumen intersects this cross-sectional plane is located inside this polygon.

FIGS. 1 through 4 show an example of a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; wherein each longitudinal expandable chamber has a central longitudinal axis which spans from its proximal end to its distal end; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening;

wherein this food flow lumen has a central longitudinal axis which spans from its proximal opening to its distal opening; wherein there is at least one cross-sectional plane of this device which is intersected by the central longitudinal axis of the food flow lumen and the central longitudinal axes of the longitudinal expandable chambers; wherein the points where the central longitudinal axes of the longitudinal expandable chambers intersect this cross-sectional plane can be geometrically connected to form a polygon; and wherein the point where the central longitudinal axis of the food flow lumen intersects this cross-sectional plane is located inside this polygon.

FIGS. 1 through 4 show an example of a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable members collectively encircle, encompass, enclose, contain, and/or surround at least 50% of the perimeter of the artificial food flow lumen.

FIGS. 1 through 4 show an example of a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable chambers collectively encircle, encompass, enclose, contain, and/or surround at least 50% of the perimeter of the artificial food flow lumen.

FIGS. 1 through 4 show an example of a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable members collectively comprise a ring of columns and/or an arcuate colonnade which encircles, encompasses, encloses, contains, and/or surrounds at least 50% of the perimeter of the artificial food flow lumen.

FIGS. 1 through 4 show an example of a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable chambers collectively comprise a ring of columns and/or an arcuate colonnade which encircles, encompasses, encloses, contains, and/or surrounds at least 50% of the perimeter of the artificial food flow lumen.

FIGS. 1 through 4 show an example of a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable members are radially distributed around at least 50% of the perimeter of the artificial food flow lumen.

FIGS. 1 through 4 show an example of a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; and (b) an artificial food flow lumen; wherein this food flow lumen has a proximal opening which is configured to be closer to the gastroesophageal junction and a distal opening which is configured to be closer to the pylorus; wherein food flows into the proximal opening and out of the distal opening; and wherein the longitudinal expandable chambers are radially distributed around at least 50% of the perimeter of the artificial food flow lumen.

FIGS. 1 through 4 show an example of a multi-columnar expandable intragastric food flow lumen device comprising: (a) at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; wherein each longitudinal expandable member has a central longitudinal axis which spans from its proximal end to its distal end; and (b) an artificial food flow lumen; wherein this food flow lumen has a proximal opening which is configured to be closer to the gastroesophageal junction and a distal opening which is configured to be closer to the pylorus; wherein this food flow lumen has a central longitudinal axis which spans from its proximal opening to its distal opening; wherein food flows into the proximal opening and out of the distal opening; and wherein the central longitudinal axis of the food flow lumen is straight parallel or arcuately parallel to the central longitudinal axes of the longitudinal expandable members.

FIGS. 1 through 4 show an example of a multi-columnar expandable intragastric food flow lumen device comprising: (a) an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; wherein each longitudinal expandable chamber has a central longitudinal axis which spans from its proximal end to its distal end; and (b) an artificial food flow lumen; wherein this food flow lumen has a proximal opening which is configured to be closer to the gastroesophageal junction and a distal opening which is configured to be closer to the pylorus; wherein this food flow lumen has a central longitudinal axis which spans from its proximal opening to its distal opening; wherein food flows into the proximal opening and out of the distal opening; and wherein the central longitudinal axis of the food flow lumen is straight parallel or arcuately parallel to the central longitudinal axes of the longitudinal expandable chambers.

FIGS. 1 through 4 show an example of a multi-columnar expandable intragastric food flow lumen device comprising: at least three longitudinal expandable members; wherein these longitudinal expandable members are configured to be inserted into and expanded within a person's stomach; wherein these longitudinal expandable members are expanded by being filled with one or more flowable substances selected from the group consisting of a gas, a liquid, a gel, and a foam; wherein each longitudinal expandable member has a proximal end which is configured to be closer to the gastroesophageal junction and a distal end which is configured to be closer to the pylorus; and wherein the walls of these longitudinal expandable members collectively form an artificial food flow lumen with a proximal opening which is configured to be closer to the gastroesophageal junction and a distal opening which is configured to be closer to the pylorus.

FIGS. 1 through 4 show an example of a multi-columnar expandable intragastric food flow lumen device comprising: an expandable multi-chambered member with at least three longitudinal expandable chambers which is configured to be inserted into and expanded within a person's stomach; wherein these longitudinal expandable chambers are expanded by being filled with one or more flowable substances selected from the group consisting of a gas, a liquid, a gel, and a foam; wherein each longitudinal expandable chamber has a proximal end which is configured to be closer to the gastroesophageal junction and a distal end which is configured to be closer to the pylorus; and wherein the walls of the expandable multi-chambered member form an artificial food flow lumen with a proximal opening which is configured to be closer to the gastroesophageal junction and a distal opening which is configured to be closer to the pylorus.

FIGS. 5 through 8 show another example of how this invention can be embodied in an expandable intragastric food flow lumen device comprising: (a) a plurality of expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) a food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

The example shown in FIGS. 5 through 8 is like the one shown in FIGS. 1 through 4, except that expandable members (505, 506, 507, 508, 509, and 510) in FIGS. 5 through 8 have cross-sections which are shaped like rounded trapezoids, keystones, or (using your imagination a bit) guitar picks. Having expandable members with cross-sectional shapes like rounded trapezoids, keystones, or guitar picks can be a result of the outward-facing portions of the expandable member walls having greater elasticity and/or being thinner than the inward-facing portions of these walls. Having rounded trapezoid, keystone, or guitar pick shaped cross sections can help to make the central food lumen stronger and less susceptible to collapse.

FIG. 5 shows a side view of this device after it has already been inserted into the stomach and expanded within the stomach. FIG. 5 also shows a cross-sectional side view of the gastroesophageal junction 101, stomach 102, pylorus 103, and duodenum 104. FIG. 6 shows a circular cross-sectional view of this same device near the gastroesophageal junction. FIG. 7 shows a circular cross-sectional view of this same device near the middle of the stomach between the gastroesophageal junction and the pylorus. FIG. 8 shows a circular cross-sectional view of this same device near the pylorus. FIGS. 5 through 8 show six longitudinal expandable members (505, 506, 507, 508, 509, and 510) which encircle, encompass, form, contain, and surround central food lumen 601. Relevant examples and variations which are discussed elsewhere in this detailed description of the figures can also be applied to this example and are not all repeated here.

FIGS. 9 through 12 show another example of how this invention can be embodied in an expandable intragastric food flow lumen device comprising: (a) a plurality of expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) a food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

The example shown in FIGS. 9 through 12 is like the one shown in FIGS. 5 through 8 except that expandable members (905, 906, 907, 908, 909, and 910) are connected by a sinusoidal ring 911. In this example, this sinusoidal ring is a wire or spring. In this example, this sinusoidal ring is part of the wall of a central food flow lumen. FIG. 9 shows a side view of this device after it has been expanded within a stomach. FIG. 9 shows a cross-sectional side view of gastroesophageal junction 101, stomach 102, pylorus 103, and duodenum 104. FIG. 10 shows a circular cross-sectional view of this same device near the gastroesophageal junction. FIG. 11 shows a circular cross-sectional view of this same device near the middle of the stomach. FIG. 12 shows a circular cross-sectional view of this same device near the pylorus. FIGS. 9 through 12 show six longitudinal expandable members (905, 906, 907, 908, 909, and 910) which encircle, encompass, form, contain, and surround a central food lumen. FIGS. 9 through 12 also show sinusoidal ring 911 around the central food lumen. Relevant examples and variations which are discussed elsewhere in this description of the figures can also be applied to this example and are not all repeated here.

FIGS. 13 through 16 show another example of how this invention can be embodied in an expandable intragastric food flow lumen device comprising: (a) a plurality of expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) a food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

The example shown in FIGS. 13 through 16 is like the example in FIGS. 1 through 4 except that expandable members (1305, 1306, 1307, 1308, 1309, and 1310) are centrally connected by ring 1401. FIG. 13 shows a side view of this device within a stomach. FIG. 13 also shows a cross-sectional side view of gastroesophageal junction 101, stomach 102, pylorus 103, and duodenum 104. FIG. 14 shows a circular cross-sectional view of this same device near the gastroesophageal junction. FIG. 15 shows a circular cross-sectional view of this same device near the middle of the stomach. FIG. 16 shows a circular cross-sectional view of this same device near the pylorus. FIGS. 13 through 16 show six longitudinal expandable members (1305, 1306, 1307, 1308, 1309, and 1310) which encircle, encompass, form, contain, and surround a central food lumen. Relevant examples and variations which are discussed elsewhere in this description of the figures can also be applied to this example and are not all repeated here.

FIGS. 17 through 20 show another example of how this invention can be embodied in an expandable intragastric food flow lumen device comprising: (a) a plurality of expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) a food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

The example shown in FIGS. 17 through 20 is like the example shown in FIGS. 1 through 4 except that there are now two rings of expandable members—an inner ring and an outer ring. In this example, there is an inner set or inner ring of expandable members (1705, 1706, 1707, 1708, 1709, and 1710) which are closer to food flow lumen 1801 and an outer set or outer ring of expandable members (1802) which are further from food flow lumen 1801. FIG. 17 shows a side view of this device within a stomach. FIG. 17 also shows a cross-sectional side view of gastroesophageal junction 101, stomach 102, pylorus 103, and duodenum 104. FIG. 18 shows a circular cross-sectional view of this same device near the gastroesophageal junction. FIG. 19 shows a circular cross-sectional view of this same device near the middle of the stomach. FIG. 20 shows a circular cross-sectional view of this same device near the pylorus.

FIGS. 17 through 20 show an inner ring of six longitudinal expandable members (1705, 1706, 1707, 1708, 1709, and 1710) which encircle, encompass, form, contain, and surround central food flow lumen 1801 and a single outer toriodal expandable member (1802) which surrounds the inner ring. Relevant examples and variations which are discussed elsewhere in this description of the figures can also be applied to this example and are not all repeated here.

FIGS. 17 through 20 show an inner set or inner ring of expandable members which are closer to a food flow lumen and an outer set or outer ring of expandable members which are further away from the food flow lumen. In this example, these two sets or two rings are both nested and concentric. In this example, the inner set or inner ring comprises multiple expandable members. In this example, the outer set or outer ring comprises a single expandable member. In this example, the inner set or inner ring comprises multiple longitudinal expandable members. In this example, the outer set or outer ring comprises a single toroidal expandable member. In this example, the inner set or inner ring comprises an arcuate colonnade of expandable members and the outer set or outer ring comprises a single toriodal member. In this example, expandable members or chambers in an inner set or inner ring have circular cross-sectional shapes. In this example, the expandable member in the outer set or outer ring has a toroidal cross-sectional shape. In this example, the first set of expandable members forms a circular colonnade around the central food flow lumen.

FIGS. 17 through 20 show an example wherein an outer set or outer ring is wider than an inner set or inner ring. This can help the device to better conform to the arcuate walls of the stomach in order to better restrict food flow through the stomach. In this example, an inner set or inner ring of expandable members has different (e.g. smaller) cross-sectional sizes than an outer set or inner ring of expandable members. In an example, an outer set or ring can expand more than an inner set or inner ring. In an example, an outer ring can be more elastic or have more folds (prior to expansion) than an inner ring. In an example, an inner set or inner ring of expandable members can have different (e.g. less elastic or more elastic) walls than an outer set or inner ring of expandable members. In an example, an inner set or inner ring of expandable members can have different (e.g. thicker or thinner) walls than an outer set or inner ring of expandable members. In an example, an inner set or inner ring of expandable members can be filled with a different (e.g. more or less dense) flowable substance than an outer set or inner ring of expandable members. In an example, an inner set or inner ring of expandable members can be filled to a different (e.g. higher or lower) pressure level than an outer set or inner ring of expandable members. In an example, a first set of expandable members can be expanded before the second set of expandable members is expanded.

FIGS. 17 through 20 show a first set of expandable members in a first ring (or ring segment) around a food flow lumen and a second set of expandable members in a second ring (or ring segment), wherein members in these two sets differ in one or more aspects selected from the group consisting of: cross-sectional shape, cross-sectional size, diameter, internal pressure, length, longitudinal curvature, longitudinal shape, number of members per set or ring, type of internal flowable substance, wall elasticity, wall material, wall thickness, and wall uniformity. FIGS. 17 through 20 show an expandable intragastric food flow lumen device which includes one or more toroidal expandable members, wherein these one or more toroidal expandable members are configured to be inserted into and expanded within a person's stomach, and wherein these one or more toroidal expandable members are expanded by being filled with a flowable substance.

FIGS. 21 through 24 show another example of how this invention can be embodied in an expandable intragastric food flow lumen device comprising: (a) a plurality of expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) a food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

The example in FIGS. 21 through 24 is like the one in FIGS. 17 through 20, except that expandable members (2105, 2106, 2107, 2108, 2109, and 2110) in the first (inner) set or ring have keystone-shaped cross sections. Looking at this ring from another perspective, the expandable members in the inner ring are configured like a "wagon wheel" around the central hub which forms the perimeter of the food flow lumen. These expandable members can also be interpreted as expandable chambers of a multi-chamber ring. As in the example shown in FIGS. 17 through 20, the second (outer) set or ring of this example is a single toroidal expandable member 2201.

FIG. 21 shows a side view of this device within a stomach and also includes cross-sectional side views of the gastroesophageal junction 101, stomach 102, pylorus 103, and duodenum 104. FIG. 22 shows a circular cross-sectional view of this same device near the gastroesophageal junction.

FIG. 23 shows a circular cross-sectional view of this same device near the middle of the stomach. FIG. 24 shows a circular cross-sectional view of this same device near the pylorus. FIGS. 21 through 24 show six longitudinal expandable members (2105, 2106, 2107, 2108, 2109, and 2110) which encircle, encompass, form, contain, and surround a central food lumen. In this example, these expandable members are configured like a wagon wheel with inflatable members (or chambers) between flexible spokes and a food flow lumen in the central hub position. Relevant examples and variations which are discussed elsewhere in this description of the figures can also be applied to this example and are not all repeated here.

FIGS. 21 through 24 show an example of a expandable intragastric food flow lumen device comprising: one or more toroidal expandable members; wherein these one or more toroidal expandable members are configured to be inserted into and expanded within a person's stomach; and wherein these one or more toroidal expandable members are expanded by being filled with one or more flowable substances selected from the group consisting of a gas, a liquid, a gel, and a foam. In this and other examples, expandable members can also be viewed as expandable chambers in a multi-chamber member. Accordingly, FIGS. 21 through 24 can also be viewed as showing an expandable intragastric food flow lumen device comprising: an expandable multi-chambered member with one or more expandable toroidal expandable chambers which is configured to be inserted into and expanded within a person's stomach; and wherein these one or more toroidal expandable chambers are expanded by being filled with one or more flowable substances selected from the group consisting of a gas, a liquid, a gel, and a foam.

FIGS. 25 through 28 show another example of how this invention can be embodied in an expandable intragastric food flow lumen device comprising: (a) a plurality of expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) a food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

The example shown in FIGS. 25 through 28 is like the example shown in FIGS. 21 through 24, except that the inner ring includes longitudinal expandable members or chambers (2505, 2506, 2507, 2508, 2509, and 2510) with circular cross-sections inside the expandable members or chambers with keystone-shaped cross sections. This compound structure may provide greater strength for the walls of the central food lumen.

FIG. 25 shows a side view of this device within a stomach as well as cross-sectional side views of gastroesophageal junction 101, stomach 102, pylorus 103, and duodenum 104. FIG. 26 shows a cross-sectional view of this same device near the gastroesophageal junction. FIG. 27 shows a cross-sectional view of this same device near the middle of the stomach. FIG. 28 shows a cross-sectional view of this same device near the pylorus. FIGS. 25 through 28 show: an inner ring of longitudinal expandable members (2505, 2506, 2507, 2508, 2509, and 2510) which encircle, encompass, form, contain, and surround a central food lumen; and an outer ring comprising a single expandable toroidal member 2601. Relevant examples and variations which are discussed elsewhere in this description of the figures can also be applied to this example and are not all repeated here.

FIGS. 29 through 32 show another example of how this invention can be embodied in an expandable intragastric food flow lumen device comprising: (a) a plurality of expandable members; wherein these expandable members are configured to be inserted into and expanded within a person's stomach; wherein these expandable members are expanded by being filled with one or more flowable substances selected from the group consisting of a gas, a liquid, a gel, and a foam; wherein each expandable member has a proximal surface which is configured to be closer to the gastroesophageal junction and a distal surface which is configured to be closer to the pylorus; wherein each expandable member has a central axis which spans from its proximal surface to its distal surface; and (b) a food flow lumen; wherein this food flow lumen has a proximal opening which is configured to be closer to the gastroesophageal junction and a distal opening which is configured to be closer to the pylorus; wherein food flows into the proximal opening and out of the distal opening; wherein this food flow lumen has a central axis which spans from its proximal opening to its distal opening; wherein there is at least one plane of this device which is intersected by the central axis of the food flow lumen and the central axes of the expandable members; wherein the points where the central axes of the expandable members intersect this plane can be geometrically connected to form a polygon; and wherein the point where the central axis of the food flow lumen intersects this plane is located inside this polygon.

The example shown in FIGS. 29 through 32 is like the example shown in FIGS. 17 through 20, except that the outer ring of expandable members comprise a longitudinal coaxial stack of multiple toroidal expandable members (including 2901, 2902, and 2903) instead of a single toroidal expandable member. Having a longitudinal coaxial stack of toroidal expandable members for the outer ring of this device can enable the device to better conform to the curves of the stomach walls. This, in turn, can help to better restrict and control the flow of food through the stomach. In this example, expandable members (3005, 3006, 3007, 3008, 3009, and 3010) in the inner ring have circular cross-sections.

FIG. 29 shows a side view of this device within a stomach. FIG. 29 also shows a cross-sectional side view of gastroesophageal junction 101, stomach 102, pylorus 103, and duodenum 104. FIG. 30 shows a circular cross-sectional view of this same device near the gastroesophageal junction. FIG. 31 shows a circular cross-sectional view of this same device near the middle of the stomach. FIG. 32 shows a circular cross-sectional view of this same device near the pylorus. FIGS. 29 through 32 show: an inner ring with longitudinal expandable members (3005, 3006, 3007, 3008, 3009, and 3010) which encircle, encompass, form, contain, and surround a central food lumen; and an outer ring with a longitudinal stack of toroidal expandable members (including 2901, 2902, and 2903). Relevant examples and variations which are discussed elsewhere in this description of the figures can also be applied to this example and are not all repeated here.

In the example shown in FIGS. 29 through 32, there are multiple expandable members (2901, 2902, and 2903) which are toroidal in shape. In this example, these expandable members are shaped like doughnuts. In a bit of geometric irony, having a bunch of doughnut-shaped members in your stomach can help you to avoid consuming a bunch of real doughnuts. In this example, the outer ring of this device is a longitudinal stack of coaxial toroidal expandable members. In this example, the inner ring is comprised of an arcuate colonnade of longitudinal expandable members and the outer ring is a longitudinal stack of coaxial toroidal expandable members. In an example, a longitudinal stack of toroidal expandable members can be configured to span from the esophageal junction to the pylorus. In an example, the middle portions of a longitudinal stack of toroidal expandable members can be expanded to occupy more than 75% of the central cross-sectional area of the stomach. In an example, the middle portions of a longitudinal stack of toroidal expandable members can be expanded to occupy the entire central cross-sectional area of the stomach.

Figure 36:
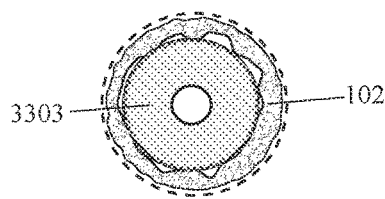
FIG. 36 shows a cross-sectional view of the device in FIG. 33 near the pylorus.
Figure 34:
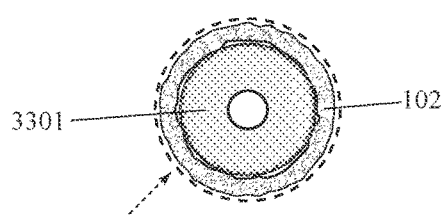
FIG. 34 shows a cross-sectional view of the device in FIG. 33 near the gastroesophageal junction.
Figure 33:
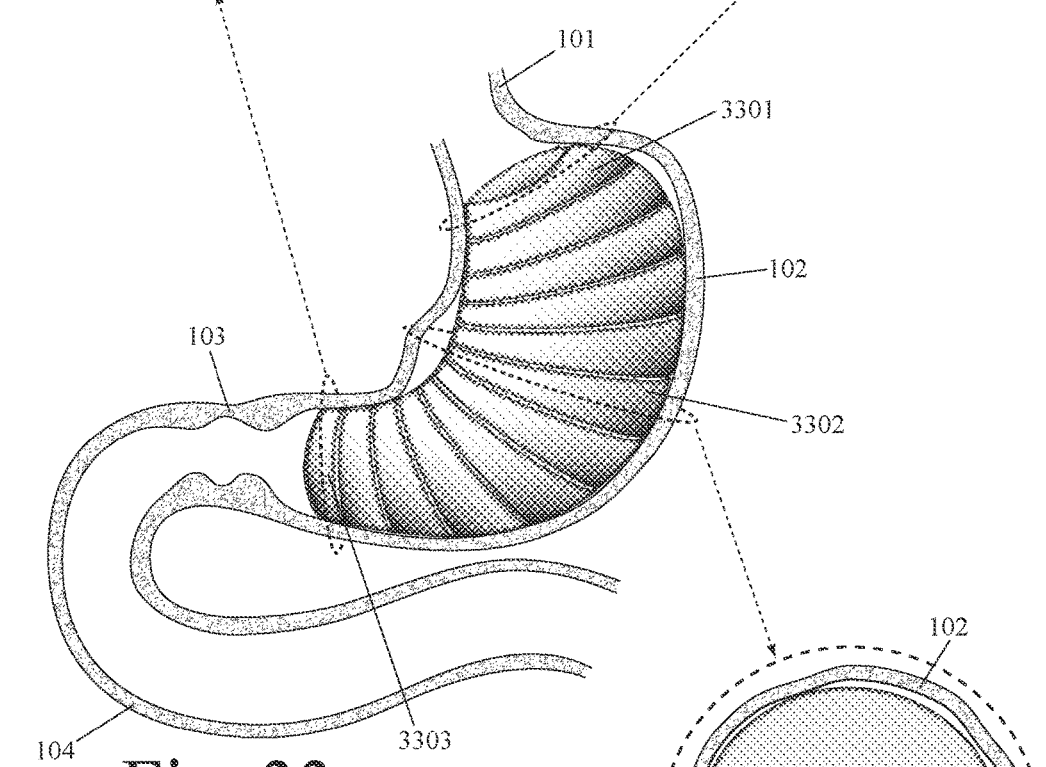
FIG. 33 shows a side view of an intragastric device comprising a longitudinal stack of toroidal expandable members in a single ring.
Figure 35:
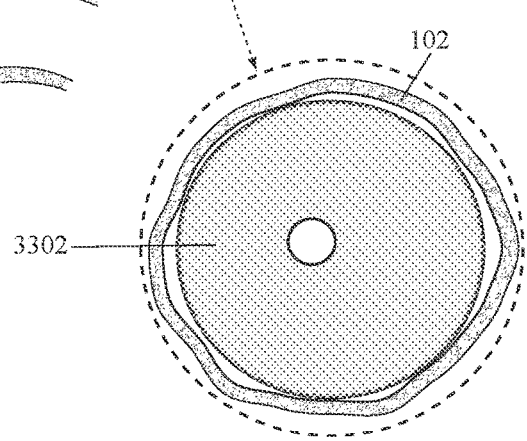
FIG. 35 shows a cross-sectional view of the device in FIG. 33 near the middle of the stomach.

The example shown in FIGS. 33 through 36 is like the example shown in FIGS. 29 through 32, except that there is only one ring, not an inner ring and an outer ring. In this example, there is only one ring and this one ring is comprised of a longitudinal coaxial stack of multiple toroidal expandable members (including 3301, 3302, and 3303). In an example, this one ring is "preeeeciouuuus". FIG. 33 shows a side view of this device within a stomach. FIG. 33 also shows a cross-sectional side view of gastroesophageal junction 101, stomach 102, pylorus 103, and duodenum 104. FIG. 34 shows a circular cross-sectional view of this same device near the gastroesophageal junction. FIG. 35 shows a circular cross-sectional view of this same device near the middle of the stomach. FIG. 36 shows a circular cross-sectional view of this same device near the pylorus. FIGS. 33 through 36 show a longitudinal coaxial stack of toroidal expandable members (including 3301, 3302, and 3303) which encircle, encompass, form, and surround a central food flow lumen. Relevant examples and variations which are discussed elsewhere in this description of the figures can also be applied to this example and are not all repeated here.

In the example shown in FIGS. 33 through 36, there are multiple expandable members (3341, 3342, and 3343) which are toroidal in shape. In this example, this device comprises a longitudinal coaxial stack of toroidal expandable members. In an example, this longitudinal coaxial stack of toroidal expandable members can be configured to span from the esophageal junction to the pylorus. In an example, the middle portions of this longitudinal stack are expanded to occupy more than 75% of the central cross-sectional area of the stomach. In an example, the middle portions of this longitudinal stack are expanded to occupy the entire central cross-sectional area of the stomach.

Figure 40:
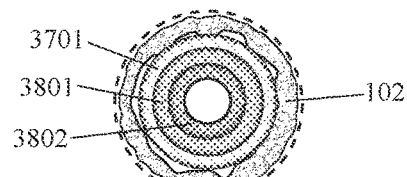
FIG. 40 shows a cross-sectional view of the device in FIG. 37 near the pylorus.
Figure 38:
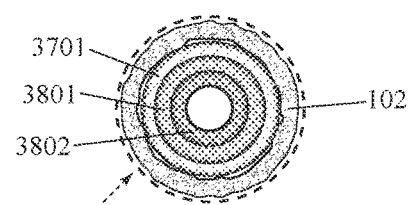
FIG. 38 shows a cross-sectional view of the device in FIG. 37 near the gastroesophageal junction.
Figure 37:
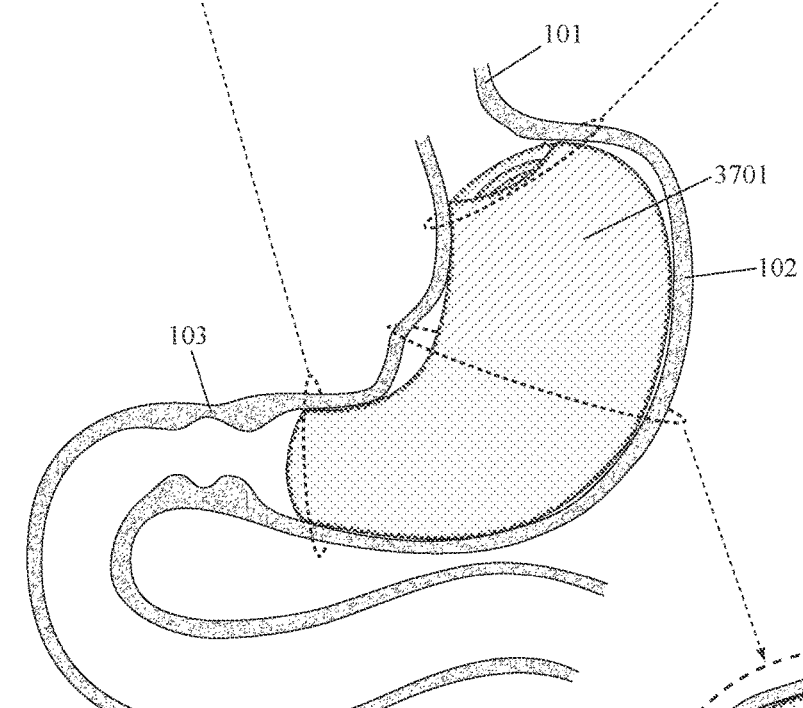
FIG. 37 shows a side view of an intragastric device comprising multiple concentric expandable members which form a food lumen.
Figure 39:
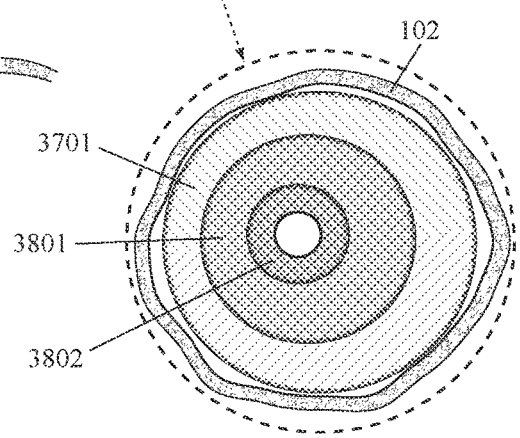
FIG. 39 shows a cross-sectional view of the device in FIG. 37 near the middle of the stomach.

The example shown in FIGS. 37 through 40 has multiple concentric toroidal expandable members (3701, 3801, and 3802) which encircle a central food flow lumen. In this example, 3701 is an outer concentric toroidal expandable member, 3801 is a middle concentric toroidal expandable member, and 3802 is an inner concentric toroidal expandable member. In this example, the inner walls of toroidal expandable member 3802 form the walls of a central food flow lumen. FIG. 37 shows a side view of this device within a stomach. FIG. 37 also shows a cross-sectional side view of gastroesophageal junction 101, stomach 102, pylorus 103, and duodenum 104. FIG. 38 shows a circular cross-sectional view of this same device near the gastroesophageal junction. FIG. 39 shows a circular cross-sectional view of this same device near the middle of the stomach. FIG. 40 shows a circular cross-sectional view of this same device near the pylorus. Relevant examples and variations which are discussed elsewhere in this description of the figures can also be applied to this example and are not all repeated here.

FIGS. 37 through 40 show an example of how this invention can be embodied in a device wherein a plurality of toriodal expandable members are nested and concentric. In this example, a plurality of toroidal expandable members comprise a plurality of rings around a central food flow lumen. In an example, toroidal expandable members which are closer to the food flow lumen can have less wall elasticity, greater wall pressure, greater internal pressure, and/or be filled with a more dense flowable substance than toroidal expandable members which are further from the food flow lumen.

The example shown in FIGS. 41 through 44, like the example in previous figures, has multiple concentric toroidal expandable members (4101, 4201, and 4302) which encircle a central food flow lumen. However, the example shown in FIGS. 41 through 44 differs from all of the devices shown in previous figures because this example is explicitly adjustable. This device is post-operatively, non-invasively, and reversibly adjustable. This is possible because the example shown in FIGS. 41 through 44 further comprises one or more pumping mechanisms (4203 and 4204). These pumping mechanisms pump a flowable substance from the interior of one or more expandable members into the interior of one or more other expandable members. Pumping a flowable substance from one expandable member to another can change the cross-sectional size and/or shape of the central food flow lumen which, in turn, can change the flow of food through stomach 102. Relevant examples and variations which are discussed elsewhere in this description of the figures can also be applied to this example and are not all repeated here.

In an example, one or more pumping mechanisms (such as 4203 and 4204) can include one or more components selected from the group consisting of: the pump itself, a power source (to power the pump and other components), a power transducer (to harvest kinetic or other energy to recharge the power source), a data processor (to process data and control pump operation), a data transmitter (in wireless communication with a remote and/or external device), a data receiver (in wireless communication with a remote and/or external device), and one or more sensors (which detect food consumption and/or identify the types and amounts of food consumed).

In an example, the pump itself can be selected from the group consisting of: Archimedes pump, axial pump, balloon pump, centripetal/fugal pump, ciliary motion pump, compressive pump, continuous flow pump, diaphragm pump, elastomeric pump, electromagnetic field pump, electromechanical pump, electroosmotic pump, gear pump, hybrid pulsatile and continuous pump, hydrodynamically-levitated pump, hydroelastic pump, impedance pump, longitudinal-membrane-wave pump, magnetic flux pump, Micro Electro Mechanical System (MEMS) pump, peristaltic pump, piston pump, pump with a helical impeller, pump with a parallel-axis impeller, pump with a perpendicular-axis impeller, pump with a series of circumferentially-compressive members, pump with an expansion chamber and one-way valve, pump with an impeller with multiple vans, fins, and/or blades, pump with electromagnetically-driven magnetic impeller, rotary pump, and worm pump.

Figures 41, 42:
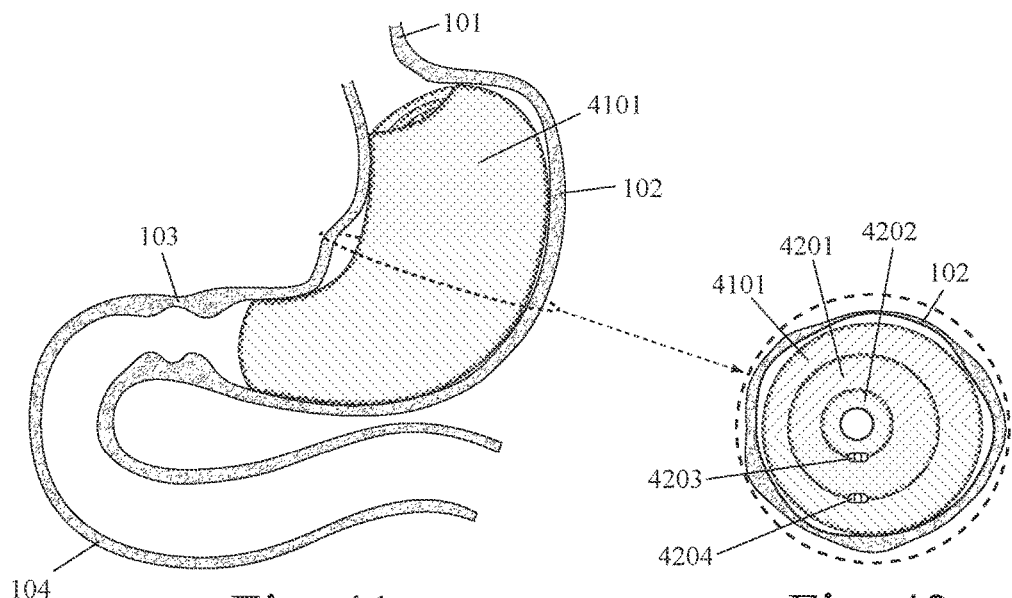
FIG. 41 shows a side view of an intragastric device before a flowable substance is pumped between expandable members.
FIG. 42 shows a cross-sectional view of the device and time shown in FIG. 41.
Figures 43, 44:
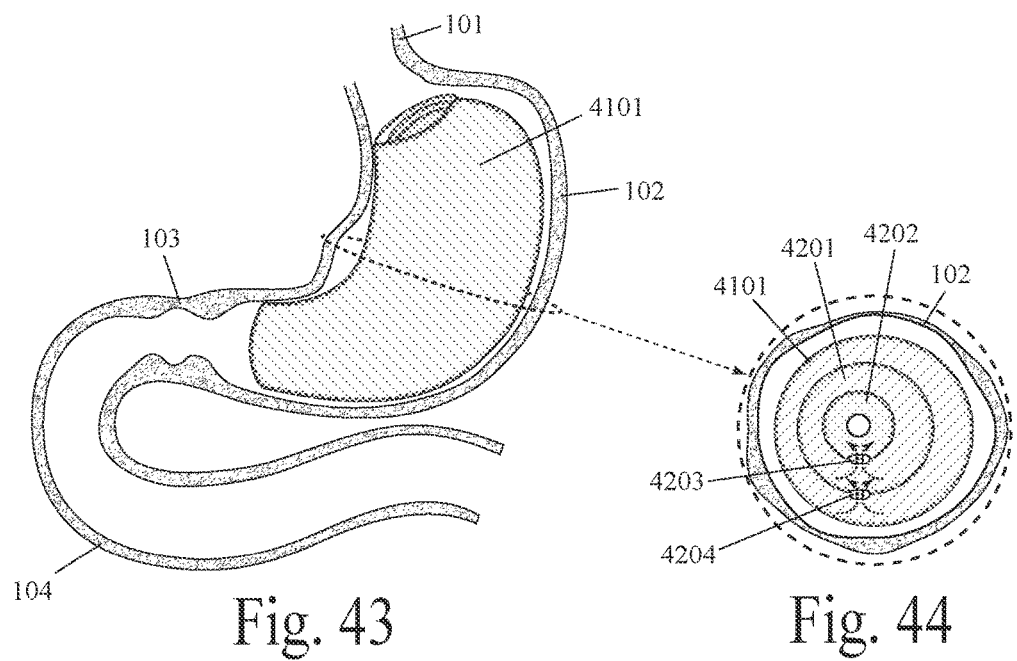
FIG. 43 shows a side view of an intragastric device as a flowable substance is being pumped between expandable members.
FIG. 44 shows a cross-sectional view of the device and time shown in FIG. 43.

FIG. 41 shows a side view of this device within a stomach at a first point in time when pumping mechanisms (4203 and 4204) are not pumping a flowable substance from one expandable member to another. FIG. 41 also shows a cross-sectional side view of gastroesophageal junction 101, stomach 102, pylorus 103, and duodenum 104. FIG. 42 shows a circular cross-sectional view of this same device near the middle of the stomach at this first point in time. FIG. 43 shows a side view of this device within a stomach at a second point in time when pumping mechanisms (4203 and 4204) are pumping a flowable substance from one expandable member to another. FIG. 44 shows a circular cross-sectional view of this same device near the middle of the stomach at this second point in time.

Two sets of arcuate dotted-line arrows in FIG. 44 show the flow of the flowable substance as pumping mechanism 4204 pumps this flowable substance from the interior of expandable member 4101 into the interior of expandable member 4201 and as pumping mechanism 4203 pumps this flowable substance from the interior of expandable member 4201 into the interior of expandable member 4202. As a result of this pumping action, the cross-sectional size of the central food flow lumen is reduced. This reduction in the cross-sectional size of the food flow lumen, in turn, reduces the flow of food through stomach 102. It can also reduce the amount of food which stomach 102 can hold. In this manner, activation of pumping mechanisms 4204 and 4203 adjusts the flow of food through stomach 102 and/or the amount of food which stomach 102 can hold. In an example, pumping mechanisms 4204 and 4203 can also pump the flowable substance in the other direction to increase the size of the food flow lumen. In an example, pumping a flowable substance from one concentric ring to another ring can change the overall volume of the array of concentric rings if the rings have different wall elasticities, wall thicknesses, wall shapes, and/or interior pressure levels.

In an example, this device can be part of a system that further comprises an external remote control unit with which the implantable portion within the stomach is in wireless communication. In an example, this device can be part of a system that further comprises a mobile phone application with which the implantable portion within the stomach is in wireless communication. In an example, this device can be part of a system that further comprises an external wearable accessory with which the implantable portion within the stomach is in wireless communication. In an example, this device can be part of a system that further comprises an external smart garment with which the implantable portion within the stomach is in wireless communication. In an example, this device can be part of a system with one or more external sensors which monitor food consumption and identify the types and/or amounts of food consumed. In an example, this device can be part of a system with one or more implanted sensors which monitor food consumption and identify the types and/or amounts of food consumed.

In an example, this device can be part of an energy balance system which includes software for tracking the types and/or amounts of food and/or nutrients consumed. In an example, this device can be part of a system which tracks the cumulative amounts of food and/or nutrients consumed. In an example, this device can be part of an energy balance system which tracks the consumption of food that is high in simple carbohydrates, food that is high in simple sugars, food that is high in saturated or trans fat, fried food, food that is high in Low Density Lipoprotein (LDL), and/or food that is high in sodium. In an example, this device can be part of an energy balance system which tracks the consumption of one or more nutrients selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, the operation of one or more pumping mechanisms can be controlled by an external remote control unit, an external wearable accessory, an external smart garment, one or more external sensors, and/or one or more implanted sensors. In an example, one or more pumping mechanisms can automatically reduce the size of a food flow lumen when data from one or more sensors indicate that a person is consuming food. In an example, one or more pumping mechanisms can automatically reduce the size of a food flow lumen when data from one or more sensors indicate that a person is consuming an unhealthy type and/or amount of food.

In an example, the flow of food through a food flow lumen can be adjusted. In an example, the flow of food through the food flow lumen can be non-invasively and reversibly adjusted. In an example, the flow of food through the food flow lumen can be adjusted by pumping a flowable substance from the interior of a first set of one or more expandable members into the interior of second set of one or more expandable members. In an example, pumping a flowable substance from the interior of a first set of expandable members into the interior of a second set of expandable members can be used to adjust the flow of food through the food flow lumen by adjusting the size and/or shape of the food flow lumen. In an example, pumping a flowable substance from the interior of a first set of expandable members into the interior of a second set of expandable members can be used to adjust the cross-sectional size of the food flow lumen.

In an example, the flow of food through a food flow lumen can be non-invasively and reversibly adjusted by an internal pumping mechanism which is in wireless communication with an external remote control unit. In an example, the flow of food through the food flow lumen can be non-invasively and reversibly adjusted by an internal pumping mechanism which is in wireless communication with an external wearable accessory. In an example, the flow of food through the food flow lumen can be non-invasively and reversibly adjusted by an internal pumping mechanism based on data from one or more internal sensors. In an example, a pumping mechanism can automatically change the cross-sectional size of a food flow lumen based on food consumption data from one or more sensors. In an example, a pumping mechanism can automatically change the cross-sectional size of a food flow lumen when a person consumes an unhealthy type and/or quantity of food based on data from one or more sensors.

In an example, this device can further comprise a wireless data receiver and transmitter which is in wireless communication with an external remote control unit. In an example, the cross-sectional size and/or shape of a food flow lumen can be reversibly and post-operatively adjusted by a remote control unit which activates a pumping mechanism to pump a flowable substance from one expandable member to another. In an example, the cross-sectional size and/or shape of a food flow lumen can be post-operatively, non-invasively, and reversibly adjusted by wireless communication from an external remote control unit which triggers a pumping mechanism to pump a flowable substance from one expandable member to another.

In an example, this device can be part of a system which further comprises a wearable accessory. In an example, a wearable accessory can be selected from the group consisting of: a wrist band, a watch, an arm band, electronically-functional eyewear, smart clothing, electronically-functional earware, a necklace or pendant, electronically-functional tattoo and/or patch, and oral appliance or dental implant. In an example, this wearable accessory can be in wireless communication with a pumping mechanism which pumps a flowable substance from one expandable member to another. In an example, the cross-sectional size and/or shape of the food flow lumen can be remotely adjustable via wireless communication between an external wearable accessory and an internal pumping mechanism which pumps a flowable substance from one expandable member to another. In an example, a pumping mechanism can be triggered manually. In an example, a pumping mechanism can be triggered automatically based on food consumption detected by the wearable accessory. In an example, the cross-sectional size and/or shape of the food flow lumen can be reduced when a person eats an unhealthy type and/or amount of food.

In an example, this device can further comprise one or more implanted sensors. In an example, one or more sensors can be in wireless communication with a pumping mechanism which pumps a flowable substance from one expandable member to another. In an example, the cross-sectional size and/or shape of the food flow lumen can be automatically adjusted based on data received from one or more sensors. In an example, the pumping mechanism can be triggered automatically based on data from one or more sensors. In an example, the cross-sectional size and/or shape of the food flow lumen can be reduced when one or more sensors indicate that a person is eating an unhealthy type and/or amount of food.

In an example, data from one or more sensors can identify food as unhealthy by identifying food that is high in simple carbohydrates, food that is high in simple sugars, food that is high in saturated or trans fat, fried food, food that is high in Low Density Lipoprotein (LDL), and/or food that is high in sodium. In an example, data from one or more sensors can be used to identify one or more nutrients selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, data from one or more sensors can be used to identify one or more nutrients selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a selected type of carbohydrate, class of carbohydrates, or all carbohydrates; a selected type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a selected type of fat, class of fats, or all fats; fatty acids, monounsaturated fat, polyunsaturated fat, saturated fat, trans fat, and unsaturated fat; a selected type of cholesterol, a class of cholesterols, or all cholesterols; Low Density Lipoprotein (LDL), High Density Lipoprotein (HDL), Very Low Density Lipoprotein (VLDL), and triglycerides; a selected type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a selected type of fiber, a class of fiber, or all fiber; dietary fiber, insoluble fiber, soluble fiber, and cellulose; a specific sodium compound, a class of sodium compounds, and all sodium compounds; salt; a selected type of meat, a class of meats, and all meats; a selected type of vegetable, a class of vegetables, and all vegetables; a selected type of fruit, a class of fruits, and all fruits; a selected type of grain, a class of grains, and all grains; high-carbohydrate food, high-sugar food, high-fat food, fried food, high-cholesterol food, high-protein food, high-fiber food, and high-sodium food.

In an example, a sensor can be a chemical sensor for detecting food consumption and/or identifying food type. In an example, a chemical sensor can be in fluid communication with the food flow lumen and/or the interior of the person's stomach. In an example, a sensor can be a light energy sensor for detecting food consumption and/or identifying food type. In an example, a chemical sensor can be in optical communication with the food flow lumen and/or the interior of the person's stomach. In an example, this light energy sensor can be a spectroscopic sensor. In an example, a sensor can be a motion sensor for detecting food consumption. In an example, a sensor can be a sonic energy sensor for identifying food consumption. In an example, a sensor can be an electromagnetic energy sensor for detecting food consumption and/or identifying food type.

In an example, this device and system can further comprise one or more sensors selected from the group consisting of: motion sensor, inertial sensor, single axis, biaxial, or multi-axial accelerometer, kinematic sensor, gyroscope, tilt sensor, inclinometer, vibration sensor, bend sensor, goniometer, strain gauge, stretch sensor, pressure sensor, force sensor, flow sensor, blood flow monitor, blood pressure monitor, microcantilever sensor, microfluidic sensor, and manometer.

In an example, this device and system can further comprise one or more sensors selected from the group consisting of: electromagnetic energy sensor, electromagnetic conductivity sensor, electromagnetic resistance sensor, variable resistance sensor, electromagnetic impedance sensor, variable impedance sensor, amp meter, voltmeter, magnetometer, magnetic field sensor, compass, radio frequency (RF) sensor, Hall-effect sensor, piezocapacitive sensor, piezoelectric sensor, electrogoniometer, electrochemical sensor, electromagnetic electrode, electroosmotic sensor, electrophoresis sensor, electroporation sensor, neural impulse monitor and/or sensor, neurosensor, action potential sensor, electrocardiography (ECG) or EKG sensor and/or monitor, electroencephalography (EEG) sensor and/or monitor, electromagnetic brain activity sensor and/or monitor, electrogastrography (EGG) sensor and/or monitor, electromyography (EMG) sensor and/or monitor, electromagnetic muscle activity sensor, electrooculography (EOG) sensor and/or monitor, hemoencephalography (HEG) monitor, micro electromechanical system (MEMS) sensor, cardiac function monitor, cardiotachometer, cardiovascular monitor, heart rate monitor, heart sensor, pulse monitor, pulmonary function and/or respiratory function monitor, respiration rate monitor, tidal volume sensor, spirometry monitor, pneumography sensor, and breathing monitor.

In an example, this device and system can further comprise one or more sensors selected from the group consisting of: light energy sensor, electro-optical sensor, infrared sensor, laser sensor, light intensity sensor, optical sensor, optoelectronic sensor, photochemical sensor, photoelectric sensor, photometer, ultraviolet light sensor, thermoluminescence sensor, variable-translucence sensor, photoplethysmography (PPG) sensor, chemiluminescence sensor, fluorescence sensor, camera, video recorder, spectroscopic sensor, light-spectrum-analyzing sensor, color sensor, spectral analysis sensor, spectrometry sensor, spectrophotometric sensor, spectroscopy sensor, near-infrared, infrared, ultraviolet, or white light spectroscopy sensor, mass spectrometry sensor, Raman spectroscopy sensor, ion mobility spectroscopic sensor, backscattering spectrometry sensor, chromatography sensor, optical glucose sensor, gas chromatography sensor, and analytical chromatography sensor.

In an example, this device and system can further comprise one or more sensors selected from the group consisting of: sound sensor, sonic energy sensor, microphone, chewing and/or swallowing monitor, ambient sound sensor or monitor, ultrasound sensor, Doppler ultrasound sensor, audiometer, temperature and/or thermal energy sensor, thermistor, thermometer, thermopile, body temperature sensor, ambient temperature sensor, biochemical sensor, amino acid sensor, artificial olfactory sensor, blood glucose monitor, blood oximeter, body fat sensor, caloric expenditure monitor, caloric intake monitor, capnography sensor, carbon dioxide sensor, carbon monoxide sensor, cerebral oximetry monitor, chemical sensor, chemiresistor sensor, chemoreceptor sensor, cholesterol sensor, cutaneous oxygen monitor, ear oximeter, food composition analyzer, food identification sensor, food consumption monitor, caloric intake monitor, gas composition sensor, glucometer, glucose monitor, humidity sensor, hydration sensor, laboratory-on-a-chip, microbial sensor, moisture sensor, osmolality sensor, oximeter, oximetry sensor, oxygen consumption monitor, oxygen level monitor or sensor, oxygen saturation monitor, pH level sensor, porosity sensor, pulse oximeter, skin moisture sensor, sodium sensor, tissue oximetry sensor, and tissue saturation oximeter.

In an example, this device can further comprise a data processor which receives data from the one or more sensors. In an example, this data processor can analyze this data to detect food consumption and identify the types and/or amounts of food consumed. In an example, this device can further comprise a data transmitter and receiver. In an example, a data transmitter can transmit data from one or more sensors to an external and/or remote data processor which analyzes this data to detect food consumption and identify the types and/or amounts of food consumed. In an example, a data receiver can receive data from a remote control unit to trigger activation of the pumping mechanism to change the cross-sectional size and/or shape of the food flow lumen. In an example, this device can further comprise a power source (such as a battery). In an example, this device can further comprise a power transducer which generates electricity from the kinetic energy or body motion. In an example, energy harvested from kinetic energy can be used to recharge a power source (such as a battery).

In an example, this device can further comprise at least one pumping mechanism which pumps a flowable substance from the interior of one expandable member into the interior of another expandable member. In an example, this device can further comprise at least one pumping mechanism which pumps a flowable substance from the interior of one or more expandable members in an inner set or inner ring of such members into the interior of one or more expandable members in an outer set or outer ring of such members. In an example, such pumping can change the cross-sectional size and/or shape of a central food flow lumen. In an example, this pumping can be triggered manually through the use of an external remote control unit. In an example, this pumping can be triggered automatically based on data from one or more implanted sensors. In an example, this pumping can be triggered automatically when this data indicates that the person is consuming an unhealthy type and/or amount of food.

Figure 45:
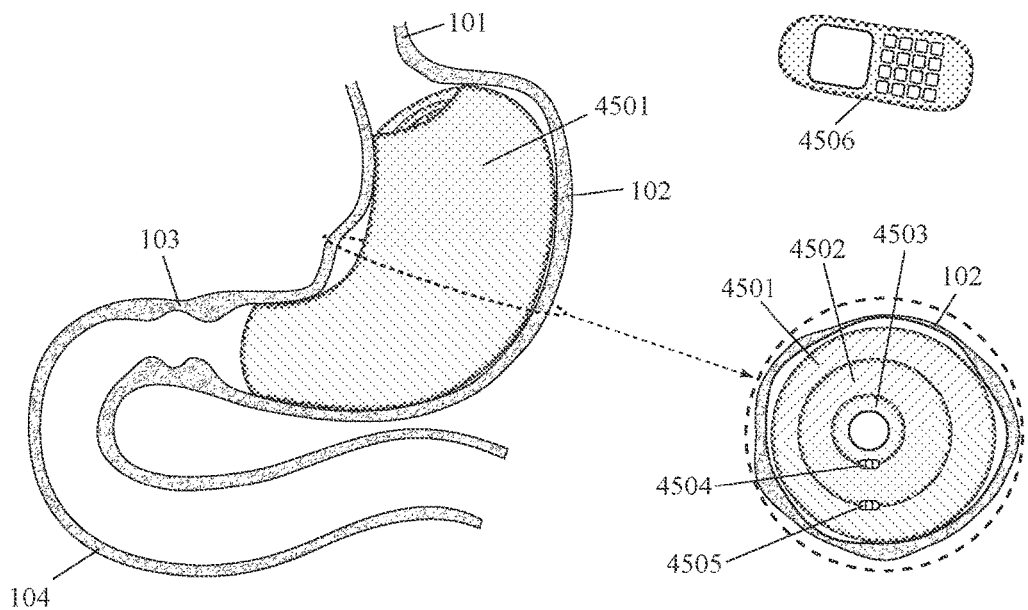
FIG. 45 shows side and cross-sectional views of an intragastric device or system with an external remote control unit before a flowable substance is pumped between expandable members.
Figure 46:
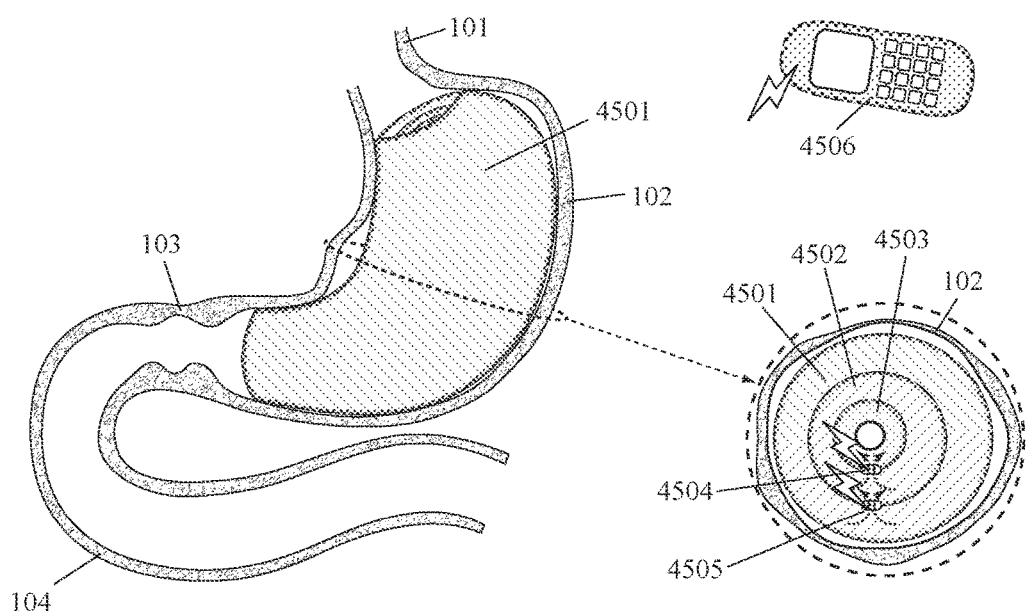
FIG. 46 shows side and cross-sectional views of an intragastric device or system with an external remote control unit being used to activate pumping of a flowable substance between expandable members.

The device shown in FIGS. 45 and 46, like the device shown in the previous set of figures, has three rings of concentric toroidal expandable members (4501, 4502, and 4503) which encircle a central food flow lumen. Like the device shown in the previous set of figures, the device in FIGS. 45 and 46 also has pumping mechanisms (4504 and 4505) which pump a flowable substance from the interior of one expandable member into the interior of another expandable member. This pumping can change the cross-sectional size and/or shape of the central food flow lumen. In this manner, the cross-sectional size and/or shape of the central food flow lumen can be post-operatively and non-invasively adjusted. In an example, one or both pumping mechanisms 4504 and 4505 can further comprise one or more components selected from the group consisting of: the pump itself, a power source, a power transducer, a data processor, a data transmitter, a data receiver, and a sensor. Relevant examples and variations which are discussed elsewhere in this description of the figures can also be applied to this example and are not all repeated here.

The example shown in FIGS. 45 and 46 differs from examples shown in earlier figures because it explicitly shows an external remote control unit (4506) which controls pumping mechanisms 4504 and 4505 through wireless communication. In an example, an external remote control unit can be a single-function piece of hardware. In an example, an external remote control unit can be a mobile device with multiple functions. In an example, an external remote control unit can be a software application which is part of a multi-function mobile phone. In an example, this device can be part of an energy balance system which tracks the types and/or amounts of nutrients consumed as well as energy expended. In this example, the portion of this invention which is implanted within the stomach 102 is in wireless communication with an external remote control unit. In these figures, this wireless communication is symbolically represented by lightning bolt symbols. In an example, the external components of this system and the implantable components of this system are wirelessly integrated to create an overall system for energy balance management and nutritional improvement.

In this example, the flow of food through a food flow lumen can be remotely, post-operatively, reversibly, and non-invasively adjusted. In this example, the flow of food through a food flow lumen can be remotely, post-operatively, reversibly, and non-invasively adjusted by changing the size and/or shape of the food flow lumen. In this example, an external remote control unit (4506) is used to activate one or more pumping mechanisms (4504 and 4505) which pump a flowable substance into an inner toroidal expandable member 4503, which—in turn—reduces the cross-sectional size of the food flow lumen, which—in turn—reduces the flow of food through stomach 102. This can also work in the reverse direction. An external remote control unit (4506) can be used to activate one or more pumping mechanisms (4504 and 4505) which pump a flowable substance out of an inner toroidal expandable member 4503, which—in turn—increases the cross-sectional size of the food flow lumen, which—in turn—increases the flow of food through stomach 102.

FIG. 45 shows this device and system at a first point in time wherein external remote control unit 4506 has not activated pumping mechanisms 4504 and 4505. FIG. 46 shows this device and system at a second point in time wherein external remote control unit 4506 has, via wireless communication, activated pumping mechanisms 4504 and 4505 to pump flowable substance from expandable member 4501 into expandable member 4502 and from expandable member 4502 into expandable member 4503. Increased flowable substance pressure and/or volume inside expandable member 4503 has, in turn, decreases the cross-sectional size of the central food flow lumen. This, in turn, reduces the flow of food through stomach 102 and/or the amount of food which can be held by stomach 102.

In an example, the pumps within pumping mechanisms 4504 and 4505 can be selected from the group consisting of: Archimedes pump, axial pump, balloon pump, centripetal/fugal pump, ciliary motion pump, compressive pump, continuous flow pump, diaphragm pump, elastomeric pump, electromagnetic field pump, electromechanical pump, electroosmotic pump, gear pump, hybrid pulsatile and continuous pump, hydrodynamically-levitated pump, hydroelastic pump, impedance pump, longitudinal-membrane-wave pump, magnetic flux pump, Micro Electro Mechanical System (MEMS) pump, peristaltic pump, piston pump, pump with a helical impeller, pump with a parallel-axis impeller, pump with a perpendicular-axis impeller, pump with a series of circumferentially-compressive members, pump with an expansion chamber and one-way valve, pump with an impeller with multiple vans, fins, and/or blades, pump with electromagnetically-driven magnetic impeller, rotary pump, and worm pump.

In an example, the flow of food through the food flow lumen can be adjusted by pumping a flowable substance from the interior of a first set of one or more expandable members into the interior of second set of one or more expandable members. In an example, pumping a flowable substance from the interior of a first set of expandable members into the interior of a second set of expandable members can be used to adjust the flow of food through the food flow lumen by adjusting the size and/or shape of the food flow lumen. In an example, pumping a flowable substance from the interior of a first set of expandable members into the interior of a second set of expandable members can be used to adjust the cross-sectional size of the food flow lumen.

In this example, this device and system further comprises a wireless data receiver and a data transmitter which are in wireless communication with an external remote control unit. In this example, the cross-sectional size and/or shape of a food flow lumen is post-operatively, reversibly, and non-invasively adjusted by a remote control unit which activates one or more pumping mechanisms to pump a flowable substance from the interiors of a first set of one or more expandable members to the interiors of a second set of one or more expandable members. In this example, the cross-sectional size and/or shape of a food flow lumen is post-operatively, non-invasively, and reversibly adjusted by wireless communication from an external remote control unit which triggers a pumping mechanism to pump a flowable substance from one expandable member to another. In an example, there can be multiple food flow lumens and the cross-sectional sizes and/shapes of these multiple food flow lumens can be individually adjusted by multiple pumping mechanisms.

Figure 47:
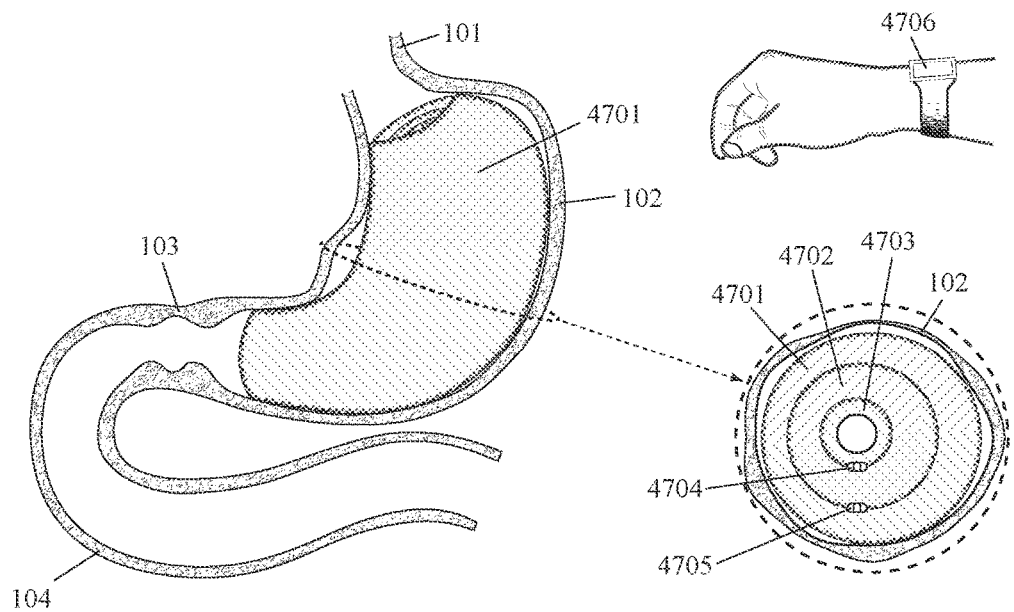
FIG. 47 shows side and cross-sectional views of an intragastric device or system with a wearable food consumption sensor before a flowable substance is pumped between expandable members.
Figure 48:
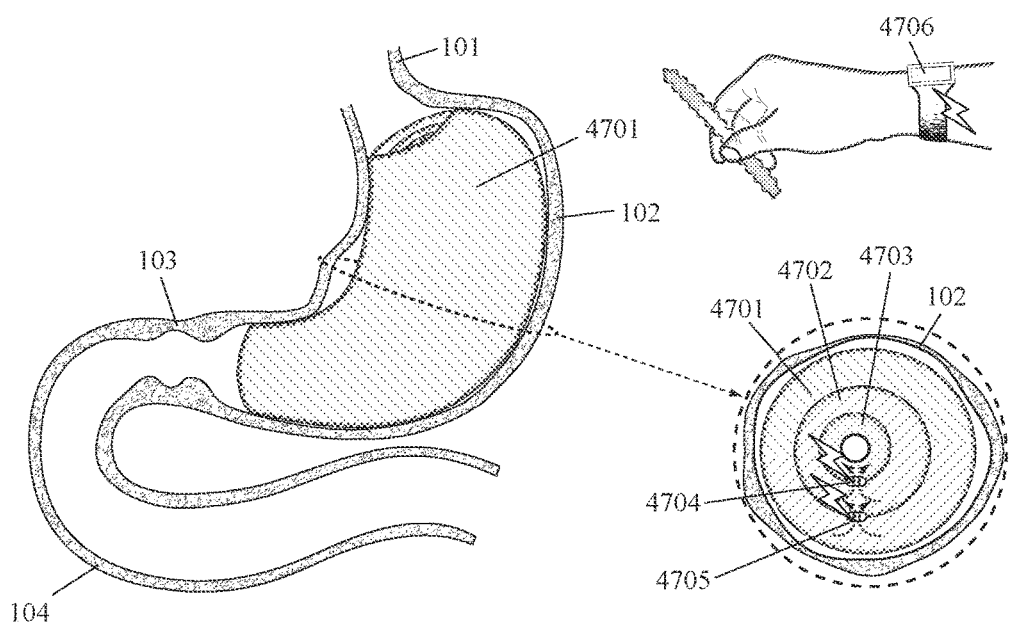
FIG. 48 shows side and cross-sectional views of an intragastric device or system with a wearable food consumption sensor being used to activate pumping of a flowable substance between expandable members.

The device and system shown in FIGS. 47 and 48, like the one shown in the previous set of figures, has three rings of concentric toroidal expandable members (4701, 4702, and 4703) which encircle a central food flow lumen and also has pumping mechanisms (4704 and 4705) which pump a flowable substance from the interior of one expandable member into the interior of another expandable member. As was the case with the previous one, this device and system allows remote adjustment of the cross-sectional size and/or shape of the central food flow lumen. As with the previous device and system, pumping mechanisms 4704 and 4705 can further comprise one or more components selected from the group consisting of: the pump itself, a power source, a power transducer, a data processor, a data transmitter, a data receiver, and a sensor. Relevant examples and variations which are discussed elsewhere in this description of the figures can also be applied to this example and are not all repeated here.

The device and system shown in FIGS. 47 and 48 differs from the previous one in that pumping mechanisms 4704 and 4706 are in wireless communication with an external wearable accessory 4706. In this example, external wearable accessory 4706 is a smart watch or wrist band. In various examples, an external wearable accessory can be selected from the group consisting of: wrist band, wrist watch, smart watch, bracelet, bangle, strap, other wrist-worn band, eyewear, eyeglasses, contact lens, virtual reality glasses or visor, augmented reality glasses or visor, monocle, goggles, sunglasses, eye mask, visor, electronically-functional eyewear, necklace, neck chain, neck band, collar, dog tags, pendant, beads, medallion, brooch, pin, button, cuff link, tie clasp, finger ring, artificial finger nail, finger nail attachment, finger tube, head band, hair band, wig, headphones, helmet, ear ring, ear plug, ear bud, hearing aid, ear muff, other ear attachment, respiratory mask, face mask, nasal mask, nose ring, nasal pillow, arm bracelet, bangle, amulet, strap, or band, ankle bracelet, bangle, amulet, strap, or band, artificial tooth, dental implant, dental appliance, dentures, dental bridge, braces, upper palate attachment or insert, tongue ring, band, chain, electronic tattoo, adhesive patch, bandage, belt, waist band, suspenders, chest band, abdominal brace, elbow brace, knee brace, shoulder brace, shoulder pad, ankle brace, pocketbook, purse, key chain, and wallet.

In an example, external wearable accessory 4706 can gather and store information on the types and/or amount of food which a person consumes because the person wearing the accessory enters food consumption information into the device via a human-to-computer interface. In an example, this human-to-computer interface can be a touch-based or voice-based interface. In an example, this human-to-computer interface can be part of food tracking software with a menu which makes it easier for the person to enter information concerning food that they eat. In an example, food tracking software can track the cumulative amount of food and/or nutrients that a person consumes during a selected period of time and can remotely adjust the cross-sectional size and/or shape of the food flow lumen based on what a person has eaten.

In an example, external wearable accessory 4706 can gather and store information on the types and/or amount of food which a person consumes by receiving data from one or more sensors which monitor food consumption and/or identify the types of food consumed. In an example, these one or more sensors can be part of the external wearable accessory. In an example, these one or more sensors can be optical sensors, electromagnetic energy sensors, motion sensors, or sonic energy sensors. In an example, an external wearable accessory can include and/or receive data from one or more sensors selected from the group consisting of: motion sensor, inertial sensor, single axis, biaxial, or multi-axial accelerometer, kinematic sensor, gyroscope, tilt sensor, inclinometer, vibration sensor, bend sensor, goniometer, strain gauge, stretch sensor, pressure sensor, force sensor, flow sensor, blood flow monitor, blood pressure monitor, microcantilever sensor, microfluidic sensor, and manometer.

In an example, an external wearable accessory can include and/or receive data from one or more sensors selected from the group consisting of: electromagnetic energy sensor, electromagnetic conductivity sensor, electromagnetic resistance sensor, variable resistance sensor, electromagnetic impedance sensor, variable impedance sensor, amp meter, voltmeter, magnetometer, magnetic field sensor, compass, radio frequency (RF) sensor, Hall-effect sensor, piezocapacitive sensor, piezoelectric sensor, electrogoniometer, electrochemical sensor, electromagnetic electrode, electroosmotic sensor, electrophoresis sensor, electroporation sensor, neural impulse monitor and/or sensor, neurosensor, action potential sensor, electrocardiography (ECG) or EKG sensor and/or monitor, electroencephalography (EEG) sensor and/or monitor, electromagnetic brain activity sensor and/or monitor, electrogastrography (EGG) sensor and/or monitor, electromyography (EMG) sensor and/or monitor, electromagnetic muscle activity sensor, electrooculography (EOG) sensor and/or monitor, hemoencephalography (HEG) monitor, micro electromechanical system (MEMS) sensor, cardiac function monitor, cardiotachometer, cardiovascular monitor, heart rate monitor, heart sensor, pulse monitor, pulmonary function and/or respiratory function monitor, respiration rate monitor, tidal volume sensor, spirometry monitor, pneumography sensor, and breathing monitor.

In an example, an external wearable accessory can include and/or receive data from one or more sensors selected from the group consisting of: light energy sensor, electro-optical sensor, infrared sensor, laser sensor, light intensity sensor, optical sensor, optoelectronic sensor, photochemical sensor, photoelectric sensor, photometer, ultraviolet light sensor, thermoluminescence sensor, variable-translucence sensor, photoplethysmography (PPG) sensor, chemiluminescence sensor, fluorescence sensor, camera, video recorder, spectroscopic sensor, light-spectrum-analyzing sensor, color sensor, spectral analysis sensor, spectrometry sensor, spectrophotometric sensor, spectroscopy sensor, near-infrared, infrared, ultraviolet, or white light spectroscopy sensor, mass spectrometry sensor, Raman spectroscopy sensor, ion mobility spectroscopic sensor, backscattering spectrometry sensor, chromatography sensor, optical glucose sensor, gas chromatography sensor, and analytical chromatography sensor.

In an example, an external wearable accessory can include and/or receive data from one or more sensors selected from the group consisting of: sound sensor, sonic energy sensor, microphone, chewing and/or swallowing monitor, ambient sound sensor or monitor, ultrasound sensor, Doppler ultrasound sensor, audiometer, temperature and/or thermal energy sensor, thermistor, thermometer, thermopile, body temperature sensor, ambient temperature sensor, biochemical sensor, amino acid sensor, artificial olfactory sensor, blood glucose monitor, blood oximeter, body fat sensor, caloric expenditure monitor, caloric intake monitor, capnography sensor, carbon dioxide sensor, carbon monoxide sensor, cerebral oximetry monitor, chemical sensor, chemiresistor sensor, chemoreceptor sensor, cholesterol sensor, cutaneous oxygen monitor, ear oximeter, food composition analyzer, food identification sensor, food consumption monitor, caloric intake monitor, gas composition sensor, glucometer, glucose monitor, humidity sensor, hydration sensor, laboratory-on-a-chip, microbial sensor, moisture sensor, osmolality sensor, oximeter, oximetry sensor, oxygen consumption monitor, oxygen level monitor or sensor, oxygen saturation monitor, pH level sensor, porosity sensor, pulse oximeter, skin moisture sensor, sodium sensor, tissue oximetry sensor, and tissue saturation oximeter.

FIG. 47 shows this device and system at a first point in time when wearable accessory 4706 has not activated pumping mechanisms 4704 and 4705. FIG. 48 shows this device and system at a second point in time when wearable accessory 4706 has, via wireless communication, activated pumping mechanisms 4704 and 4705 to pump flowable substance from expandable member 4701 into expandable member 4702 and from expandable member 4702 into expandable member 4703. Increased flowable substance pressure and/or volume inside expandable member 4703 decreases the cross-sectional size of the central food flow lumen. This, in turn, reduces the flow of food through stomach 102 and/or the amount of food which can be held by stomach 102.

In this example, the flow of food through a food flow lumen can be remotely, post-operatively, reversibly, and non-invasively adjusted. In this example, the flow of food through a food flow lumen can be remotely, post-operatively, reversibly, and non-invasively adjusted by changing the size and/or shape of a food flow lumen. In this example, an external wearable accecssory (4706) is used to activate one or more pumping mechanisms (4704 and 4705) which pump a flowable substance into an inner toroidal expandable member 4703, which—in turn—reduces the cross-sectional size of the food flow lumen, which—in turn—reduces the flow of food through stomach 102. This can also work in the reverse direction. An external wearable accessory (4706) can be used to activate one or more pumping mechanisms (4704 and 4705) which pump a flowable substance out of an inner toroidal expandable member 4703, which—in turn—increases the cross-sectional size of the food flow lumen, which—in turn—increases the flow of food through stomach 102.

Figure 49:
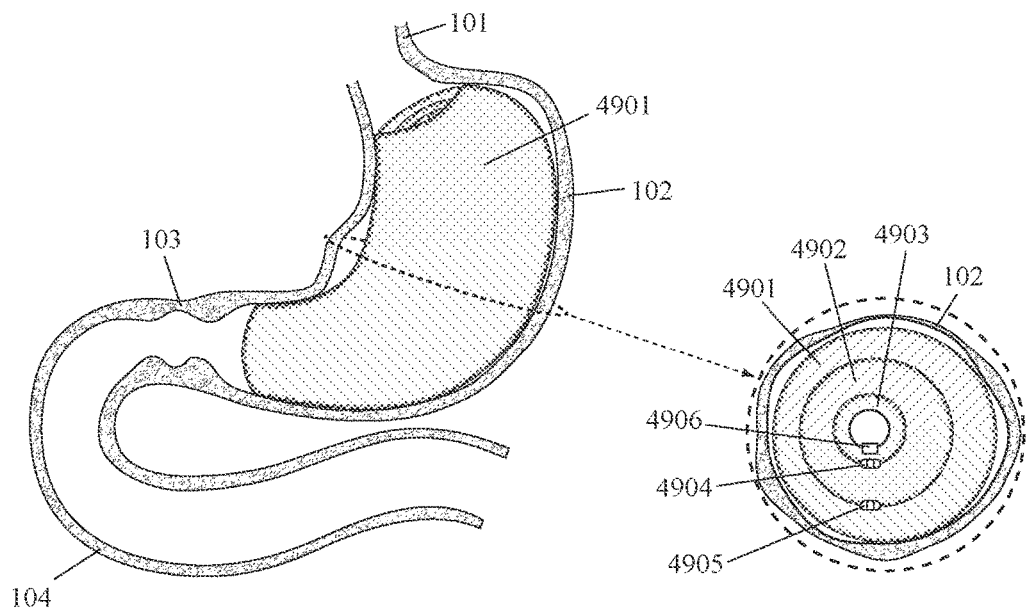
FIG. 49 shows side and cross-sectional views of an intragastric device or system with an implanted food consumption sensor before a flowable substance is pumped between expandable members.
Figure 50:
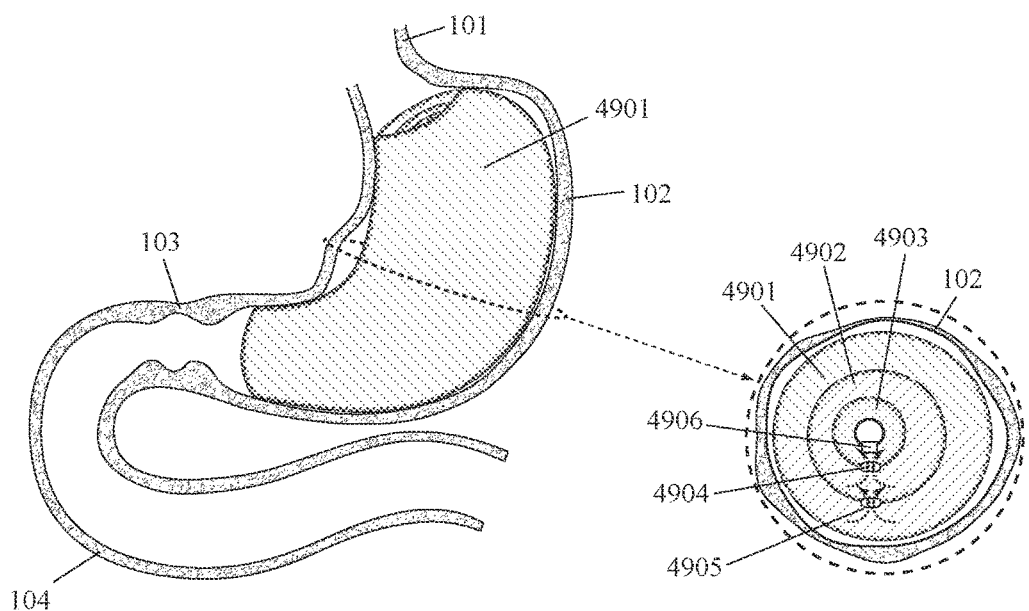
FIG. 50 shows side and cross-sectional views of an intragastric device or system with an implanted food consumption sensor being used to activate pumping of a flowable substance between expandable members.

The device and system shown in FIGS. 49 and 50, like the one shown in FIGS. 41 through 44, has three rings of concentric toroidal expandable members (4901, 4902, and 4903) which encircle a central food flow lumen and also has pumping mechanisms (4904 and 4905) which pump a flowable substance from the interior of one expandable member into the interior of another expandable member. Also, pumping mechanisms 4904 and 4905 can further comprise one or more components selected from the group consisting of: the pump itself, a power source, a power transducer, a data processor, a data transmitter, and a data receiver. This device and system is different in that it explicitly includes one or more implanted sensors (4906) and data from these one or more sensors is analyzed to automatically control the operation of pumping mechanisms 4904 and 4905. Relevant examples and variations which are discussed elsewhere in this description of the figures can also be applied to this example and are not all repeated here.

FIG. 49 shows this device and system at a first point in time wherein pumping mechanisms 4904 and 4905 are not pumping based on analysis of data from one or more sensors 4906. FIG. 50 shows this device at a second point in time wherein pumping mechanisms 4904 and 4905 are pumping based on analysis of data from one or more sensors 4906. In FIG. 50, pumping mechanisms 4904 and 4905 are pumping a flowable substance from expandable member 4901 into expandable member 4902 and from expandable member 4902 into expandable member 4903. Increased flowable substance pressure and/or volume inside expandable member 4903 decreases the cross-sectional size of the central food flow lumen. This, in turn, reduces the flow of food through stomach 102 and/or the amount of food which can be held by stomach 102.

In an example, data from one or more sensors can be analyzed by a local data processor which is part of a pumping mechanism. In an example, data from one or more sensors can be wirelessly transmitted to a remote external data processor where it is analyzed. In an example, data from one or more sensors can be analyzed to identify when a person is eating. In an example, data from one or more sensors can be analyzed to identify the types and/or amounts of food or nutrients that a person is eating. In an example, data from one or more sensors can be analyzed to track the cumulative amount of selected foods or nutrients that a person has eaten during a selected period of time. In an example, the cumulative amount of selected food or nutrients that a person eats during a selected period of time can be compared to the cumulative amount of energy expenditure by that person during this period of time to calculate an overall energy balance surplus or deficit. In an example, pumping mechanisms 4904 and 4905 can be automatically controlled based on the results of such types of data analysis.

In an example, this device can further comprise a data processor which receives data from one or more sensors. In an example, this data processor can analyze this data to detect food consumption and identify the types and/or amounts of food consumed. In an example, this device can further comprise a data transmitter and receiver. In an example, a data transmitter can transmit data from one or more sensors to an external and/or remote data processor which analyzes this data to detect food consumption and identify the types and/or amounts of food consumed. In an example, a data receiver can receive data from a remote control unit to trigger activation of the pumping mechanism to change the cross-sectional size and/or shape of the food flow lumen. In an example, this device can further comprise a power source (such as a battery). In an example, this device can further comprise a power transducer which generates electricity from the kinetic energy or body motion. In an example, energy harvested from kinetic energy can be used to recharge a power source (such as a battery).

In an example, one or more implanted sensors (such as 4906) can be in fluid communication with food in the food flow lumen. In an example, one or more sensors can be in fluid communication with other locations along the person's gastrointestinal tract. In an example, one or more sensors can be intra-oral sensors that are implanted within the person's mouth. In an example, one or more implanted sensors (such as 4906) can be in electromagnetic communication with food in the food flow lumen. In an example, one or more sensors can be in electromagnetic communication with other locations along the person's gastrointestinal tract.

In an example, one or more implanted sensors (such as 4906) can be in optical communication with food in the food flow lumen. In an example, one or more sensors can be in optical communication with other locations along the person's gastrointestinal tract.

In an example, one or more implanted sensors can be in wireless communication with a pumping mechanism which pumps a flowable substance from one expandable member to another. In an example, the cross-sectional size and/or shape of a food flow lumen can be automatically adjusted based on data received from one or more implanted sensors. In an example, a pumping mechanism can be automatically triggered automatically based on data from one or more implanted sensors. In an example, the cross-sectional size and/or shape of a food flow lumen can be reduced when one or more implanted sensors indicate that a person is eating an unhealthy type and/or amount of food.

In an example, data from one or more implanted sensors can identify food as unhealthy by identifying food that is high in simple carbohydrates, food that is high in simple sugars, food that is high in saturated or trans fat, fried food, food that is high in Low Density Lipoprotein (LDL), and/or food that is high in sodium. In an example, data from one or more implanted sensors can be used to identify one or more nutrients selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, data from one or more implanted sensors can be used to identify one or more nutrients selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a selected type of carbohydrate, class of carbohydrates, or all carbohydrates; a selected type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a selected type of fat, class of fats, or all fats; fatty acids, monounsaturated fat, polyunsaturated fat, saturated fat, trans fat, and unsaturated fat; a selected type of cholesterol, a class of cholesterols, or all cholesterols; Low Density Lipoprotein (LDL), High Density Lipoprotein (HDL), Very Low Density Lipoprotein (VLDL), and triglycerides; a selected type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a selected type of fiber, a class of fiber, or all fiber; dietary fiber, insoluble fiber, soluble fiber, and cellulose; a specific sodium compound, a class of sodium compounds, and all sodium compounds; salt; a selected type of meat, a class of meats, and all meats; a selected type of vegetable, a class of vegetables, and all vegetables; a selected type of fruit, a class of fruits, and all fruits; a selected type of grain, a class of grains, and all grains; high-carbohydrate food, high-sugar food, high-fat food, fried food, high-cholesterol food, high-protein food, high-fiber food, and high-sodium food.

In an example, an implanted sensor can be a chemical sensor for detecting food consumption and/or identifying food type. In an example, a chemical sensor can be in fluid communication with the food flow lumen and/or the interior of the person's stomach. In an example, a sensor can be a light energy sensor for detecting food consumption and/or identifying food type. In an example, a chemical sensor can be in optical communication with the food flow lumen and/or the interior of the person's stomach. In an example, this light energy sensor can be a spectroscopic sensor. In an example, a sensor can be a motion sensor for detecting food consumption. In an example, a sensor can be a sonic energy sensor for identifying food consumption. In an example, a sensor can be an electromagnetic energy sensor for detecting food consumption and/or identifying food type.

In an example, this device and system can further comprise one or more sensors selected from the group consisting of: motion sensor, inertial sensor, single axis, biaxial, or multi-axial accelerometer, kinematic sensor, gyroscope, tilt sensor, inclinometer, vibration sensor, bend sensor, goniometer, strain gauge, stretch sensor, pressure sensor, force sensor, flow sensor, blood flow monitor, blood pressure monitor, microcantilever sensor, microfluidic sensor, and manometer.

In an example, this device and system can further comprise one or more sensors selected from the group consisting of: electromagnetic energy sensor, electromagnetic conductivity sensor, electromagnetic resistance sensor, variable resistance sensor, electromagnetic impedance sensor, variable impedance sensor, amp meter, voltmeter, magnetometer, magnetic field sensor, compass, radio frequency (RF) sensor, Hall-effect sensor, piezocapacitive sensor, piezoelectric sensor, electrogoniometer, electrochemical sensor, electromagnetic electrode, electroosmotic sensor, electrophoresis sensor, electroporation sensor, neural impulse monitor and/or sensor, neurosensor, action potential sensor, electrocardiography (ECG) or EKG sensor and/or monitor, electroencephalography (EEG) sensor and/or monitor, electromagnetic brain activity sensor and/or monitor, electrogastrography (EGG) sensor and/or monitor, electromyography (EMG) sensor and/or monitor, electromagnetic muscle activity sensor, electrooculography (EOG) sensor and/or monitor, hemoencephalography (HEG) monitor, micro electromechanical system (MEMS) sensor, cardiac function monitor, cardiotachometer, cardiovascular monitor, heart rate monitor, heart sensor, pulse monitor, pulmonary function and/or respiratory function monitor, respiration rate monitor, tidal volume sensor, spirometry monitor, pneumography sensor, and breathing monitor.

In an example, this device and system can further comprise one or more sensors selected from the group consisting of: light energy sensor, electro-optical sensor, infrared sensor, laser sensor, light intensity sensor, optical sensor, optoelectronic sensor, photochemical sensor, photoelectric sensor, photometer, ultraviolet light sensor, thermoluminescence sensor, variable-translucence sensor, photoplethysmography (PPG) sensor, chemiluminescence sensor, fluorescence sensor, camera, video recorder, spectroscopic sensor, light-spectrum-analyzing sensor, color sensor, spectral analysis sensor, spectrometry sensor, spectrophotometric sensor, spectroscopy sensor, near-infrared, infrared, ultraviolet, or white light spectroscopy sensor, mass spectrometry sensor, Raman spectroscopy sensor, ion mobility spectroscopic sensor, backscattering spectrometry sensor, chromatography sensor, optical glucose sensor, gas chromatography sensor, and analytical chromatography sensor.

In an example, this device and system can further comprise one or more sensors selected from the group consisting of: sound sensor, sonic energy sensor, microphone, chewing and/or swallowing monitor, ambient sound sensor or monitor, ultrasound sensor, Doppler ultrasound sensor, audiometer, temperature and/or thermal energy sensor, thermistor, thermometer, thermopile, body temperature sensor, ambient temperature sensor, biochemical sensor, amino acid sensor, artificial olfactory sensor, blood glucose monitor, blood oximeter, body fat sensor, caloric expenditure monitor, caloric intake monitor, capnography sensor, carbon dioxide sensor, carbon monoxide sensor, cerebral oximetry monitor, chemical sensor, chemiresistor sensor, chemoreceptor sensor, cholesterol sensor, cutaneous oxygen monitor, ear oximeter, food composition analyzer, food identification sensor, food consumption monitor, caloric intake monitor, gas composition sensor, glucometer, glucose monitor, humidity sensor, hydration sensor, laboratory-on-a-chip, microbial sensor, moisture sensor, osmolality sensor, oximeter, oximetry sensor, oxygen consumption monitor, oxygen level monitor or sensor, oxygen saturation monitor, pH level sensor, porosity sensor, pulse oximeter, skin moisture sensor, sodium sensor, tissue oximetry sensor, and tissue saturation oximeter.

FIGS. 51 through 54 show an expandable intragastric device for reducing food consumption and/or absorption comprising: an upper intragastric ring which is configured to be attached to a stomach within the stomach within 6" of the gastroesophageal junction; a lower intragastric ring which is configured to be attached to a stomach within the stomach within 6" of the pylorus; and a plurality of longitudinal expandable members, wherein each longitudinal expandable member has an upper end which is attached to the upper intragastric ring and a lower end which is attached to the lower intragastric ring, and wherein each longitudinal expandable member is expanded within the stomach by being filled with one or more flowable substances selected from the group consisting of a gas, a liquid, a gel, and a foam.

FIG. 51 shows a side view of this device having been attached and expanded within a stomach. FIG. 52 shows a lateral cross-sectional view of this same device which includes the upper intragastric ring at an upper portion of the device near the gastroesophageal junction. FIG. 53 shows a lateral cross-sectional view of this same device at a middle portion of the device in approximately the longitudinal middle of the stomach. FIG. 54 shows a lateral cross-sectional view of this same device which includes the lower intragastric ring at a lower portion of the device near the pylorus.

Specifically, FIGS. 51 through 54 show: esophagus wall 5101; stomach wall 5102; pylorus wall 5103; duodenum wall 5104; a plurality of longitudinal expandable members including longitudinal expandable members 5105, 5106, 5107, 5108, 5109, and 5110; upper intragastric ring 5111; upper gastric wall attachment mechanisms 5112 and 5113; lower intragastric ring 5114; and lower gastric wall attachment mechanisms 5115 and 5116. Relevant examples and variations discussed elsewhere in this disclosure can also be applied to this example, but are not all repeated here.

In an example, an upper intragastric ring and/or a lower intragastric ring can be configured to encircle the inner perimeter of a lateral cross-section of a stomach. In an example, an upper intragastric ring and/or a lower intragastric ring can be toroidal or cylindrical in shape. In an example, the center of a central opening or lumen of an upper intragastric ring can be aligned with the center of the opening of a gastroesophageal junction. In an example, the center of a central opening or lumen of a lower intragastric ring can be aligned with the center of the opening of a pylorus. In an example, the thickness or width of an upper intragastric ring and/or a lower intragastric ring can be uniform and symmetric around a central opening or lumen. In an example, the thickness or width of an upper intragastric ring and/or a lower intragastric ring can be non-uniform and asymmetric around a central opening or lumen.

In an example an upper intragastric ring and/or a lower intragastric ring can be configured to be attached and/or anchored to the inner walls of a stomach. In an example an upper intragastric ring can each be attached and/or anchored to stomach walls using one or more intragastric attachment mechanisms. In an example a lower intragastric ring can each be attached and/or anchored to stomach walls and/or a pylorus using one or more intragastric attachment mechanisms. In an example an upper intragastric ring and/or a lower intragastric ring can be configured to be removably attached and/or anchored to the inner walls of a stomach.

In an example, an intragastric attachment mechanism can be selected from the group consisting of: staples, suture, wire, adhesive, hook, pin, clamp, clip, snap, and rivet. In this example, an upper intragastric ring and a lower intragastric ring are each attached to the inner walls of a stomach by two intragastric attachment mechanisms. In an example, an upper intragastric ring and a lower intragastric ring can each be attached to the inner walls of a stomach by three or more intragastric attachment mechanisms. In an example, an upper intragastric ring and a lower intragastric ring can removably attached to the inner walls of a stomach by three or more removable and/or detachable intragastric attachment mechanisms so that the device can be explanted and/or removed.

In an example, an upper intragastric ring can be configured to be attached to a gastroesophageal junction and/or to stomach walls within 4" of a gastroesophageal junction. In an example, an upper intragastric ring can be contiguous to a gastroesophageal junction. In an example, a lower intragastric ring can be configured to be attached to a pylorus and/or to stomach walls within 4" of a pylorus. In an example, a lower intragastric ring can be contiguous to a pylorus. In an example a lower intragastric ring can be connected to a gastric sleeve which extends into a duodenum.

In an example, an upper intragastric ring and/or a lower intragastric ring can be made from a flexibly resilient material which is sufficiently flexible to be deformed during insertion through an esophagus, but sufficiently resilient to self-expand into a ring shape after insertion into the stomach. In an example, an upper intragastric and/or lower intragastric ring can be inserted through an esophagus inside a catheter and can then self-expand when the catheter is removed within the stomach. In an example, an upper intragastric ring and/or a lower intragastric ring can be expanded within a stomach by being filled with one or more flowable substances selected from the group consisting of a gas, a liquid, a gel, and a foam.

In an example, a plurality of longitudinal expandable members can decrease, restrict, and/or slow the flow of food through a stomach. In an example, a plurality of longitudinal expandable members can form a food lumen which channels food through a stomach. In an example, a plurality of longitudinal expandable members can reduce the amount of food which a stomach can contain. In an example, a plurality of longitudinal expandable members can reduce the amount of food which is absorbed by the body. In an example, a plurality of longitudinal expandable members can simulate some effects of gastric sleeve surgery, while also offering reversibility.

In an example, a self-expanding longitudinal expandable member can be inserted through an esophagus into a stomach in a first (compressed) configuration and then expanded into a second (uncompressed) configuration within the stomach. In an example, a self-expanding longitudinal expandable member can be inserted inside a catheter through an esophagus into a stomach in a first (compressed) configuration and then (when the catheter is removed) allowed to expand into a second (uncompressed) configuration within the stomach. In an example, a self-expanding longitudinal expandable member can be made from a flexibly resilient material which self-expands when the member is removed from the constraints of a catheter. In an example, a longitudinal expandable member can be made from a hydrogel material which self-expands when the member is removed from the constraints of a catheter.

In an example, an inflatable longitudinal expandable member can be inserted through an esophagus into a stomach in a first (unexpanded) configuration and then expanded into a second (expanded) configuration within the stomach. In an example, an inflatable longitudinal expandable member can be inserted inside a catheter through an esophagus into a stomach in a first (compressed) configuration and then (when the catheter is removed) expanded into a second (uncompressed) configuration within the stomach. In an example, an inflatable longitudinal expandable member can be a balloon. In an example, a longitudinal expandable member can be expanded within a stomach by being filled with a gas, liquid, gel, or foam. In an example, a longitudinal expandable member can be folded, wrinkled, or creased for insertion into a stomach and then unfolded, unwrinkled, or otherwise expanded by being filled with a gas, liquid, gel, or foam within the stomach. In an example, a longitudinal expandable member can be filled with water or saline solution.

In an example, a plurality of longitudinal expandable members can be attached to each other as well as being attached to an upper intragastric ring and a lower intragastric ring. In an example, a plurality of longitudinal expandable members can be laterally attached to each other. In an example, a plurality of longitudinal expandable members can be laterally attached to each other along their entire lengths. In an example, a plurality of longitudinal expandable members can be laterally attached to each other such that their points of attachment form a polygon when viewed in a lateral cross-section. In an example, a plurality of longitudinal expandable members can be attached to each other such that they create an interior lumen between them through which food can pass. In an example, food passing through the upper and lower intragastric rings also passes through this interior lumen. In an alternative example, a plurality of longitudinal expandable members can be separate from each other, except through mutual attachment to upper and lower intragastric rings.

In an example, a plurality of longitudinal expandable members can comprise three longitudinal expandable members. In an example, a plurality of longitudinal expandable members can comprise four longitudinal expandable members. In an example, a plurality of longitudinal expandable members can comprise five longitudinal expandable members. In an example, a plurality of longitudinal expandable members can comprise six or more longitudinal expandable members.

In an example, a virtual lateral cross-section of a plurality of longitudinal expandable members can be made in a plane which is perpendicular to the longitudinal axes of the longitudinal expandable members. In an example, in such a virtual lateral cross-section, connecting the lateral cross-sectional centers of these longitudinal expandable members can form a triangle, square, pentagon, hexagon, octagon, or decagon. In an example, such a triangle, square, pentagon, hexagon, octagon, or decagon can be equilateral.

In an example, a plurality of longitudinal expandable members can be separate from each other. In an example, a plurality of longitudinal expandable members can be connected to each other. In an example, a plurality of longitudinal expandable members can be pair-wise connected and their central axes can be arranged in a circular or polygonal formation. In an example, there can be between 3 and 12 longitudinal expandable members. In an example, the walls of a plurality of longitudinal expandable members can form an inner food flow lumen. In an example, the walls of a plurality of longitudinal expandable members which are connected and their central axes can be arranged in a circular or polygonal formation can form a central food flow lumen. In an example, longitudinal expandable members can be arranged in a circle and the center-facing portions of the walls of the longitudinal expandable members can collectively form an inner food flow lumen. In an example, an inner food flow lumen can have walls which are encircled by, but not formed by, longitudinal expandable members.

In an example, longitudinal expandable members can be distributed around at least 50% of the perimeter of an inner food flow lumen. In an example, longitudinal expandable members can be distributed around at least 75% of the perimeter of an inner food flow lumen. In an example, longitudinal expandable members can be distributed around the entire perimeter of an inner food flow lumen. In an example, longitudinal expandable members can form a circle, oval, egg shape, or polygon around an inner food flow lumen. In an example, longitudinal expandable members can collectively comprise a ring of arcuate columns (or colonnade) around an inner food flow lumen. In an example, longitudinal expandable members can collectively comprise a ring of arcuate columns (or colonnade) with an inner food flow lumen in their middle.

In an example, longitudinal expandable members comprising a plurality of longitudinal expandable members can be equal (plus or minus 15%) in size and shape. In an example, the longitudinal expandable members comprising a plurality of longitudinal expandable members can be expanded to equal (plus or minus 15%) sizes and shapes. In an example, one or more longitudinal expandable members facing a more-distended (or greater curve) portion of the perimeter of a stomach can be larger than one or more longitudinal expandable members facing a less-distended (or lesser curve) portion of the stomach. In an example, one or more longitudinal expandable members facing a more-distended (or greater curve) portion of the perimeter of a stomach can be expanded to larger sizes than one or more longitudinal expandable members facing a less-distended (or lesser curve) portion of the stomach. In an example, one or more longitudinal expandable members facing a more-distended (or greater curve) portion of a stomach can have larger cross-sectional areas than one or more longitudinal expandable members facing a less-distended (or lesser curve) portion of a stomach.

In an example, longitudinal expandable members can have cross-sectional shapes selected from the group consisting of: a circle, an oval, an ellipse, an egg shape, a trapezoid, a keystone shape, a triangle, a rounded triangle, a convex lens shape, and a hexagon. In an example, longitudinal expandable members can have uniform size cross-sections. In an example, longitudinal expandable members can have smaller cross sections at their end portions and larger cross sections in their middle portions. In an example, longitudinal expandable members can collectively comprise an asymmetric ring of arcuate columns. In an example, longitudinal expandable members in selected radial locations can have larger cross sections than those of other longitudinal expandable members. In an example, longitudinal expandable members near the greater curve (or more-distended portion) of the stomach can have larger cross sections and columns near the lesser curve (or less-distended portion) of the stomach can have smaller cross sections. In an example, a plurality of longitudinal expandable members can be configured like a wagon wheel with inflatable members or chambers between flexible spokes, with an inner food flow lumen in the central hub position.

In an example, longitudinal expandable members can have arcuate longitudinal axes. In an example, the curvatures of longitudinal axes of longitudinal expandable members can correspond to the curvatures of stomach walls. In an example, the longitudinal axes of longitudinal expandable members can be parallel to each other prior to expansion. In an example, the longitudinal axes of longitudinal expandable members can also be parallel to the longitudinal axis of an inner food flow lumen. In example, longitudinal axes of expandable members can be more than 6" in length. In example, longitudinal axes of expandable members can be more than one foot in length.

In an example, a plurality of longitudinal expandable members can be directly attached to upper and lower intragastric rings before they are inserted into a person's body. In an example, a plurality of longitudinal expandable members can be directly attached to upper and lower intragastric rings as they are inserted into a stomach. In an example, a plurality of longitudinal expandable members can be attached to upper and lower intragastric rings by guidewires (or guide threads) before they are inserted into a person's body. In an example, a plurality of longitudinal expandable members can be attached to upper and lower intragastric rings (after the rings are attached within the stomach) using these guidewires (or guide threads). In an example, these guidewires (or guide threads) can be removed after longitudinal expandable members are attached to the rings within a stomach.

In an example, a plurality of longitudinal expandable members can be attached to upper and lower intragastric rings after they are inserted into a stomach. In an example, longitudinal expandable members can be attached to rings after the rings have been attached within a stomach with the help of imaging. In an example, a small camera can enable the longitudinal expandable members to be guided by an operator to attachment locations on the rings. In an example, longitudinal expandable members can be attached to upper and lower intragastric rings with the assistance of magnets. In an example, longitudinal expandable members can be attached to upper and lower intragastric rings via magnetic attraction between electromagnetic components on rings and electromagnetic components on longitudinal expandable members.

In an example, this device can be deployed by: inserting upper and lower intragastric rings into a stomach; attaching the rings to the inner walls of the stomach; inserting a plurality of longitudinal expandable members into the stomach; attaching the plurality of longitudinal expandable members to the upper and lower intragastric rings; and then expanding the longitudinal expandable members by filling them with a gas, liquid, gel, or foam. In an example, this device can be explanted and/or removed by reversing these steps.

In an example, an amount of gas, liquid, gel, or foam in a plurality of longitudinal expandable members can be post-operatively adjusted by subsequently inserting a tube or catheter into the stomach, connecting the tube or catheter to one or more of the longitudinal expandable members, inserting or withdrawing gas, liquid, gel, or foam, and then withdrawing the tube or catheter. In an example, longitudinal expandable members can be separately or individually expanded by being filled with a flowable substance after insertion into a stomach. In an example, longitudinal expandable members can be jointly or simultaneously expanded by being filled with a flowable substance after insertion into a stomach.

In an example, a flowable substance can be pumped (by an implanted pump) from longitudinal expandable member to another. In an example, this device can further comprise a plurality of implanted pumps which connect (member pairs within) the plurality of longitudinal expandable members. In an example, a flowable substance can be pumped from one longitudinal expandable member to another via an implanted pump which is controlled by wireless communication with an external remote control device.

In an example, the overall configuration of a plurality of longitudinal expandable members can be adjusted by an external remote control device by pumping a flowable substance between one or more longitudinal expandable members. In an example, pumping a flowable substance between one or more longitudinal expandable members can change the flow of food through a stomach. In an example, pumping a flowable substance between one or more longitudinal expandable members can change the amount of food which a stomach can contain. In an example, pumping a flowable substance between one or more longitudinal expandable members can change the amount of food which is absorbed by the body.

In an example, different longitudinal expandable members can be filled with different flowable substances. In an example, different longitudinal expandable members can be filled to different pressure levels. In an example, longitudinal expandable members which are closer to an inner food flow lumen can be filled in a liquid and longitudinal expandable members which are further from the flood flow lumen can be filled with a gas. In an example, longitudinal expandable members that are closer to an inner food flow lumen can be filled with a more dense flowable substance or filled to a higher pressure level than longitudinal expandable members that are further from an inner food flow lumen.

In an example, this device can further comprise an internal power source, an internal pump, and a wireless data transmitter. In example, the amount of gas, liquid, gel, or foam in one or more longitudinal expandable members can be wirelessly adjusted by remote communication with the wireless data transmitter which controls the operation of the internal pump which is in fluid communication with the interior of one or more longitudinal expandable members. In an example, the amount and/or pressure of gas, liquid, gel, or foam in each of a plurality of longitudinal expandable members can be remotely, individually, and/or separately adjusted.

In an example, the walls of longitudinal expandable members can be impermeable to gas and/or fluid. In an example, the walls of longitudinal expandable members can have uniform thickness and elasticity. In an example, longitudinal expandable members can be configured in a circle wherein the center-facing portions of their walls are thicker or less elastic than the outward-facing portions of their walls.

In an example, longitudinal expandable members that are closer to an inner food flow lumen can have thicker walls than longitudinal expandable members that are further from an inner food flow lumen. In an example, longitudinal expandable members that are closer to an inner food flow lumen can have less elastic walls than longitudinal expandable members that are further from an inner food flow lumen. In an example, the portions of longitudinal expandable member walls that are closer to an inner food flow lumen can be thicker than the portions of longitudinal expandable member walls that are further from an inner food flow lumen. In an example, the portions of longitudinal expandable member walls that are closer to an inner food flow lumen can be less elastic than the portions of longitudinal expandable member walls that are further from an inner food flow lumen. In an example, the walls of longitudinal expandable members can be thicker at the ends of the longitudinal expandable members than in the middle portions of the longitudinal expandable members. In an example, the walls of longitudinal expandable members can be less elastic at the ends of the longitudinal expandable members than in the middle portions of the longitudinal expandable members.

FIGS. 55 through 58 show another example of an expandable intragastric device for reducing food consumption and/or absorption. This example is similar to the one shown in FIGS. 51 through 54 except that: there are only three longitudinal expandable members; and there is an additional (middle) intragastric ring. This device comprises: an upper intragastric ring which is configured to be attached to a stomach within the stomach within 6" of the gastroesophageal junction; a lower intragastric ring which is configured to be attached to a stomach within the stomach within 6" of the pylorus; a middle intragastric ring which is configured to be attached to a stomach with the stomach between the upper intragastric ring and the lower intragastric ring; and a plurality of longitudinal expandable members, wherein each longitudinal expandable member has an upper end which is attached to the upper intragastric ring and a lower end which is attached to the lower intragastric ring, and wherein each longitudinal expandable member is expanded within the stomach by being filled with one or more flowable substances selected from the group consisting of a gas, a liquid, a gel, and a foam.

FIG. 55 shows a side view of this device having been attached and expanded within a stomach. FIG. 56 shows a lateral cross-sectional view of this same device which includes the upper intragastric ring at an upper portion of the device near the gastroesophageal junction. FIG. 57 shows a lateral cross-sectional view of this same device which includes the middle intragastric ring at a middle portion of the device in approximately the longitudinal middle of the stomach. FIG. 58 shows a lateral cross-sectional view of this same device which includes the lower intragastric ring at a lower portion of the device near the pylorus.

Specifically, FIGS. 55 through 58 show: esophagus wall 5501; stomach wall 5502; pylorus wall 5503; duodenum wall 5504; a plurality of longitudinal expandable members including longitudinal expandable members 5505, 5506, and 5510; upper intragastric ring 5511; upper gastric wall attachment mechanisms 5512 and 5513; middle intragastric ring 5514; middle gastric wall attachment mechanisms 5515 and 5516; lower intragastric ring 5517; and lower gastric wall attachment mechanisms 5518 and 5519. Relevant examples and variations discussed elsewhere in this disclosure can also be applied to this example, but are not all repeated here.

FIGS. 59 through 62 show another example of an expandable intragastric device for reducing food consumption and/or absorption. This example is similar to the one shown in FIGS. 51 through 54 except that there is only one longitudinal expandable member and this expandable member is attached directly attached to the stomach wall. This device comprises: an upper intragastric ring which is configured to be attached to a stomach within the stomach within 6" of the gastroesophageal junction; a lower intragastric ring which is configured to be attached to a stomach within the stomach within 6" of the pylorus; and a longitudinal expandable member with an upper end which is attached to the upper intragastric ring, a lower end which is attached to the lower intragastric ring, and a middle portion which is attached to the stomach wall, and wherein the longitudinal expandable member is expanded within the stomach by being filled with one or more flowable substances selected from the group consisting of a gas, a liquid, a gel, and a foam.

FIG. 59 shows a side view of this device having been attached and expanded within a stomach. FIG. 60 shows a lateral cross-sectional view of this same device which includes the upper intragastric ring at an upper portion of the device near the gastroesophageal junction. FIG. 61 shows a lateral cross-sectional view of this same device at a middle portion of the device in approximately the longitudinal middle of the stomach. FIG. 62 shows a lateral cross-sectional view of this same device which includes the lower intragastric ring at a lower portion of the device near the pylorus.

Specifically, FIGS. 59 through 62 show: esophagus wall 5901; stomach wall 5902; pylorus wall 5903; duodenum wall 5904; longitudinal expandable member 5905; upper intragastric ring 5911; upper gastric wall attachment mechanisms 5912 and 5913; middle intragastric attachment mechanism 5916; lower intragastric ring 5917; and lower gastric wall attachment mechanisms 5918 and 5919. Relevant examples and variations discussed elsewhere in this disclosure can also be applied to this example, but are not all repeated here.

FIGS. 63 through 66 show another example of an expandable intragastric device for reducing food consumption and/or absorption. This device comprises an longitudinal expandable member which is configured to be inserted into a stomach, wherein this longitudinal expandable member further comprises an upper end which is attached to the stomach wall within 6" of the gastroesophageal junction, wherein this longitudinal member further comprises a lower end which is attached to the stomach wall within 6" of the pylorus, wherein this longitudinal expandable member is also attached to the greater curve of the stomach wall at a location between its upper end and its lower end, and wherein this longitudinal expandable member is expanded within the stomach by being filled with one or more flowable substances selected from the group consisting of a gas, a liquid, a gel, and a foam.

FIG. 63 shows a side view of this device having been attached and expanded within a stomach. FIG. 64 shows a lateral cross-sectional view of this same device at an upper portion of the device near the gastroesophageal junction. FIG. 65 shows a lateral cross-sectional view of this same device at a middle portion of the device in approximately the longitudinal middle of the stomach. FIG. 66 shows a lateral cross-sectional view of this same device at a lower portion of the device near the pylorus.

Specifically, FIGS. 63 through 66 show: esophagus wall 6301; stomach wall 6302; pylorus wall 6303; duodenum wall 6304; a longitudinal expandable member 6305; an upper gastric wall attachment mechanism 6313; a middle gastric wall attachment mechanism 6316; and a lower gastric wall attachment mechanism 6319. In an example, an intragastric attachment mechanism can be selected from the group consisting of: staples, suture, wire, adhesive, hook, pin, clamp, clip, snap, and rivet. Relevant examples and variations discussed elsewhere in this disclosure can also be applied to this example, but are not all repeated here.

In an example, a longitudinal expandable member can decrease, restrict, and/or slow the flow of food through a stomach. In an example, a longitudinal expandable member can reduce the amount of food which a stomach can contain. In an example, a longitudinal expandable member can reduce the amount of food which is absorbed by the body. In an example, a longitudinal expandable member can simulate some effects of gastric sleeve surgery, while also offering reversibility.

In an example, a self-expanding longitudinal expandable member can be inserted through an esophagus into a stomach in a first (compressed) configuration and then expanded into a second (uncompressed) configuration within the stomach. In an example, a self-expanding longitudinal expandable member can be inserted inside a catheter through an esophagus into a stomach in a first (compressed) configuration and then (when the catheter is removed) allowed to expand into a second (uncompressed) configuration within the stomach. In an example, a self-expanding longitudinal expandable member can be made from a flexibly resilient material which self-expands when the member is removed from the constraints of a catheter. In an example, a longitudinal expandable member can be made from hydrogel material which self-expands when the member is removed from the constraints of a catheter.

In an example, an inflatable longitudinal expandable member can be inserted through an esophagus into a stomach in a first (unexpanded) configuration and then expanded into a second (expanded) configuration within the stomach. In an example, an inflatable longitudinal expandable member can be inserted inside a catheter through an esophagus into a stomach in a first (compressed) configuration and then (when the catheter is removed) expanded into a second (uncompressed) configuration within the stomach. In an example, an inflatable longitudinal expandable member can be a balloon. In an example, a longitudinal expandable member can be expanded within a stomach by being filled with a gas, liquid, gel, or foam. In an example, a longitudinal expandable member can be folded, wrinkled, or creased for insertion into a stomach and then unfolded, unwrinkled, or otherwise expanded by being filled with a gas, liquid, gel, or foam within the stomach. In an example, a longitudinal expandable member can be filled with water or saline solution.

In an example, a longitudinal expandable member can have smaller lateral cross sections at its upper and lower portions and larger lateral cross sections in its middle portions. In an example, a longitudinal expandable member can have an arcuate longitudinal axis. In an example, the curvature of its longitudinal axis can correspond to the curvature of a stomach wall. In example, a longitudinal expandable member can be more than 6" in length. In example, a longitudinal expandable member can be more than one foot in length.

FIGS. 67 through 70 show another expandable intragastric device for reducing food consumption and/or absorption. This device comprises a longitudinal (upper to lower, or vice versa) series of connected expandable members which is implanted and then expanded within a stomach. This longitudinal series of expandable members simulates some of the beneficial effects of gastric sleeve surgery, but offers the option of reversibility which surgery does not. In some respects, the appearance of this longitudinal series of connected expandable members is somewhat like that of a series of spinal vertebrae, but connected members in this device form a lumen for food to pass through instead of forming a lumen for the spinal cord to pass through.

The expandable intragastric device for reducing food consumption and/or absorption which is shown in FIGS. 67 through 70 comprises: a longitudinal series of three or more expandable members which are configured to collectively span from a location within the stomach within 6" of the gastroesophageal junction to a location within the stomach within 6" of the pylorus; wherein an expandable member is expanded by being filled with a flowable substance selected from the group consisting of a gas, a liquid, a gel, and a foam; wherein an expandable member further comprises a toriodal (or ring-shaped) portion which is configured to be closer to (or face) the lesser curve of the stomach wall; wherein an expandable member further comprises a bulging portion which is configured to be closer to (or face) the greater curve of the stomach wall; and wherein the expandable members are interconnected by two or more flexible longitudinal members which are attached to the stomach walls.

FIG. 67 shows a side view of this device having been inserted into, attached to, and then expanded within a stomach. FIG. 68 shows a lateral cross-sectional view of this same device at an upper portion of the device near the gastroesophageal junction. FIG. 69 shows a lateral cross-sectional view of this same device at a middle portion of the device in approximately the longitudinal middle of the stomach. FIG. 70 shows a lateral cross-sectional view of this same device at a lower portion of the device near the pylorus.

Specifically, FIGS. 67 through 70 show: esophagus wall 6701; stomach wall 6702; pylorus wall 6703; duodenum wall 6704; a longitudinal series of expandable members including expandable members 6705, 6706, 6707, 6708, 6709, 6710, and 6711; two flexible longitudinal members 6712 and 6713 which connect the expandable members; and gastric wall attachment mechanisms 6714, 6715, 6716, and 6717. Relevant examples and variations discussed elsewhere in this disclosure can also be applied to this example, but are not all repeated here.

In this example, a longitudinal series of expandable members comprises seven expandable members. In other examples, a longitudinal series of expandable members can include between three and seven expandable members. In another example, a longitudinal series of expandable members can include more than seven expandable members. In an example, expandable members in a longitudinal series can each have the same size and shape before they are expanded with a flowable substance, but they can be expanded to different sizes and/or shapes in order to better conform to (the greater curve) of the stomach wall. In an example, expandable members in a longitudinal series can have different sizes and shapes even before they are expanded. Different size and/or shape expandable members can be selected and longitudinally ordered so as to better conform to (the greater curve) of the stomach walls. In an example, larger expandable members can be selected and placed so that they occupy the longitudinal middle portion of the stomach.

In an example, each longitudinal expandable member can have a toroidal (or ring-like) portion which is closer to (and/or faces) the lesser curve of the stomach wall. In an example, the central openings of the toroidal (or ring-like) portions of a series of expandable members can create collectively form a food lumen through which food can flow. In an example, this food lumen can function like the portion of a person's stomach which remains after gastric sleeve surgery. In an example, each longitudinal expandable member can have a bulging portion which is closer to (and/or faces) the greater curve of the stomach wall. In an example, the bulging portions of the expandable members can collectively restrict food passage through the stomach outside the food lumen. In an example, this can function like the removal of the greater curve portion of a person's stomach which occurs during gastric sleeve surgery.

In an example, both the toriodal portions and the bulging portions of expandable members can be expanded by being filled with a flowable substance. In an example, the toriodal (or ring-like) portion of the expandable member can be made from a flexibly resilient material which is compressed in shape for insertion through the esophagus, but which expands into the toroidal (or ring-like) shape in the stomach. In an example, the bulging portion can be expanded by being filled with a flowable substance but the toriodal (or ring-like) portion self-expands in the stomach.

In an example, the toriodal (or ring-like) portion of an expandable member can comprise less than one-third of the area of a virtual lateral cross-section of an expandable member. In an example, the toriodal (or ring-like) portion of an expandable member can comprise less than one-third of the volume of an expandable member. In an example, the toriodal (or ring-like) portion of an expandable member can comprise less than one-half of the area of a virtual lateral cross-section of an expandable member. In an example, the toriodal (or ring-like) portion of an expandable member can comprise less than one-half of the volume of an expandable member.

In an example, the bulging portions of expandable members in the middle portion of the stomach can be larger (after expansion) than the bulging portions of expandable member in the upper and lower portions of the stomach. In an example, the percentages of virtual lateral cross-sections of expandable members in middle portions of the stomach can be larger (after expansion) than the percentage of such cross-sections of expandable members in the upper and lower portions of the stomach. In an example, the walls of the bulging portions of expandable members can be more elastic than the walls of the toroidal (or ring-like) portions of expandable members. In an example, the bulging portion of the expandable members can be thicker than the toroidal (or ring-like) portions of the expandable members.

In an example, this device can further comprise one or more implanted pumps which are in fluid communication with the interiors of two or more expandable members. In an example, an implanted pump can pump a flowable substance from the interior of a first expandable member into the interior of a second expandable member. In an example, an implanted pump can be in wireless communication with a remote control unit which enables remote control of pumping a flowable substance from the interior of a first expandable member to the interior of a second expandable member. In an example, pumping a flowable substance from the interior of one or more expandable members to the interior of one or more other expandable members can change the size and/or shape of the food lumen.

In an example, this device can further comprise a food consumption sensor which detects when the person in whom this device has been implanted is eating food. In an example, this food consumption sensor can be selected from the group consisting of: a motion sensor, an electromagnetic energy sensor, a light energy sensor and/or spectroscopic sensor, a sound energy sensor, and a biochemical sensor. In an example, this sensor can be implanted within the person's body. In an example, this sensor can be worn outside the person's body.

In an example, one or more implanted pumps can be activated and/or controlled by data from a food consumption sensor. In an example, when data from a food consumption sensor indicates that a person is eating food, then one or more implanted pumps can be activated to change the size, shape, and/or configuration of the device in order to change the flow or absorption of food within a person's body. In an example, when data from a food consumption sensor indicates that a person is eating a particular type or amount of food, then one or more implanted pumps can be activated to change the size, shape, and/or configuration of the device in order to change the flow or absorption of food within a person's body. In an example, the device may only simulate some of the effects of gastric sleeve surgery when a person is eating selected types and/or amounts of food.

In an example, flexible longitudinal members which connect three or more expandable members can be selected from the group consisting of: a wire; a cable; a spring; a cord; a string; a thread; a suture; a fiber; a tube; a chain; and a rod. In an example, an expandable member can further comprise two or more holes, loops, rings, hooks, or channels through which flexible longitudinal members pass. In an example, such holes, loops, rings, hooks, or channels can be diametrically opposite each other in a lateral cross-sectional view of an expandable member. In this example, the expandable members are connected to each other by two flexible longitudinal members. In an example, expandable members can be connected to each other by three, four, or more flexible longitudinal members. In an example, a flexible longitudinal member can have an arcuate longitudinal axis which substantially follows the curved shape of the stomach wall.

Figure 71:
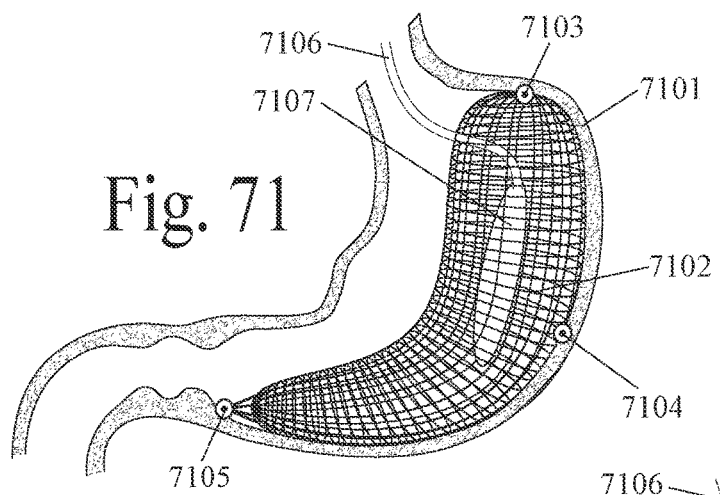
FIG. 71 shows a side view of an intragastric device comprising a mesh and an expandable member inside the mesh, before expansion of the expandable member.
Figure 72:
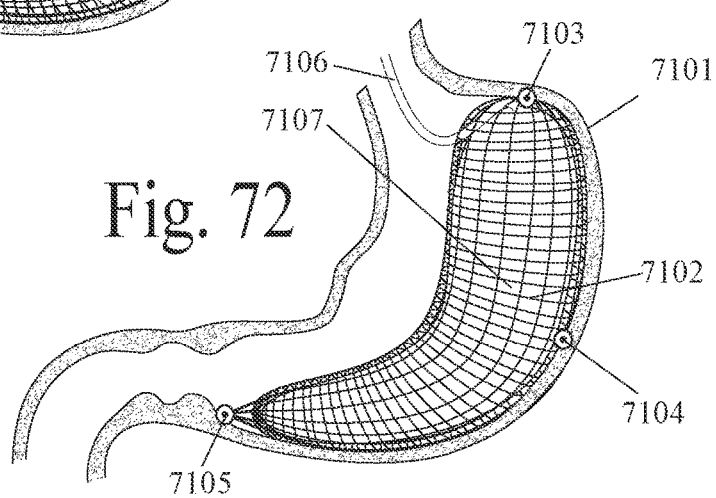
FIG. 72 shows a side view of the intragastric device in FIG. 71 after expansion of the expandable member but before removal of a catheter.
Figure 73:
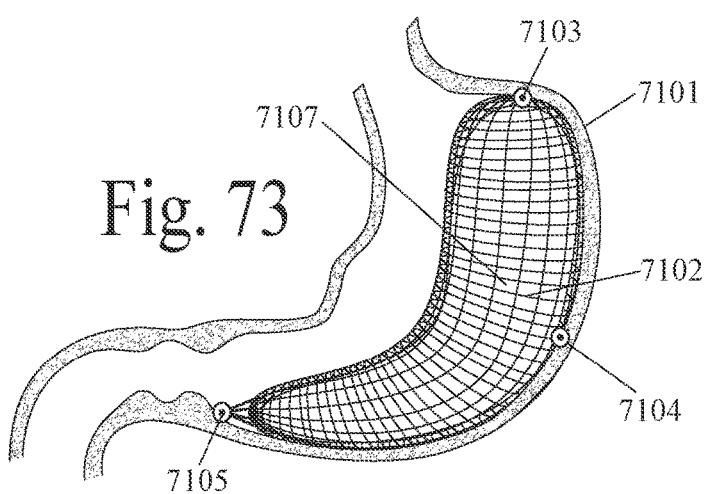
FIG. 73 shows a side view of the intragastric device in FIG. 71 after expansion of the expandable member and removal of the catheter.

FIGS. 71 through 73 show another expandable intragastric device for reducing food consumption and/or absorption. This device comprises a flexible mesh (or net) which is attached inside a stomach and a longitudinal expandable member which is expanded within the mesh (or net). This device simulates some of the beneficial effects of gastric sleeve surgery, but offers the option of reversibility which surgery does not. FIG. 71 shows a side view of a device comprising a flexible mesh (or net) containing a longitudinal expandable member, after the mesh (or net) has been inserted within and attached to a stomach, but before the longitudinal expandable member has been expanded within the flexible mesh (or net). FIG. 72 shows a side view of this device after the longitudinal expandable member has been expanded within the flexible mesh (or net), but before a catheter used to expand the expandable member has been removed. FIG. 73 shows a side view of this device after the longitudinal expandable member has been expanded within the flexible mesh (or net) and after the catheter has been removed.

The expandable intragastric device for reducing food consumption and/or absorption which is shown in FIGS. 71 through 73 comprises: a flexible mesh (or net) which is configured to be inserted into a stomach and attached to stomach walls, wherein this flexible mesh (or net) is attached to stomach walls by two or more intragastric attachment mechanisms, wherein this flexible mesh (or net) is configured to span from an upper location within 6" of the gastroesophageal junction to lower location within 6" of the pylorus; and a longitudinal expandable member which is expanded within the flexible mesh (or net) by being filled with a flowable substance selected from the group consisting of a gas, a liquid, a gel, and a foam. In an example, this device can further comprise a catheter through which a flowable substance is pumped into the longitudinal expandable member.

Specifically, FIGS. 71 through 73 show: stomach walls 7101; flexible mesh (or net) 7102; intragastric attachment mechanisms 7103, 7104, and 7105 which attach the flexible mesh (or net) to stomach walls; catheter 7106; and longitudinal expandable member 7107 within the flexible mesh (or net). Relevant examples and variations discussed elsewhere in this disclosure can also be applied to this example, but are not all repeated here. In an example, this device can provide some of the benefits of gastric sleeve surgery, but is reversible.

In an example, a flexible mesh (or net) can be made from a polymer. In an example, a flexible mesh (or net) can be made from fabric, fibers, threads, strings, cords, and/or yarns. In an example, a flexible mesh (or net) can be made from an elastic material. In an example, a flexible mesh (or net) can be made from nylon or polyethylene terephthalate. In an example, a flexible mesh (or net) can be a balloon with multiple holes in it. In an example, a flexible mesh (or net) can have quadrilateral, hexagonal, or circular openings. In an example, a flexible mesh (or net) can be made from a metal. In an example, an intragastric attachment mechanism, by which a flexible mesh (or net) is attached to stomach walls, can be selected from the group consisting of: staples, suture, wire, adhesive, hook, pin, clamp, clip, snap, and rivet.

In an example, a longitudinal expandable member can be a balloon. In an example, a longitudinal expandable member can be filled with a liquid such as saline solution. In an example, a longitudinal expandable member can be filled with a gas such as air. In an example, this device can comprise multiple expandable members which are expanded within the mesh (or net). In an example, a longitudinal expandable member can be filled with a flowable substance which is delivered through a catheter. In an example, this catheter can be subsequently detached from the expandable member and removed from the body.

Figure 74:
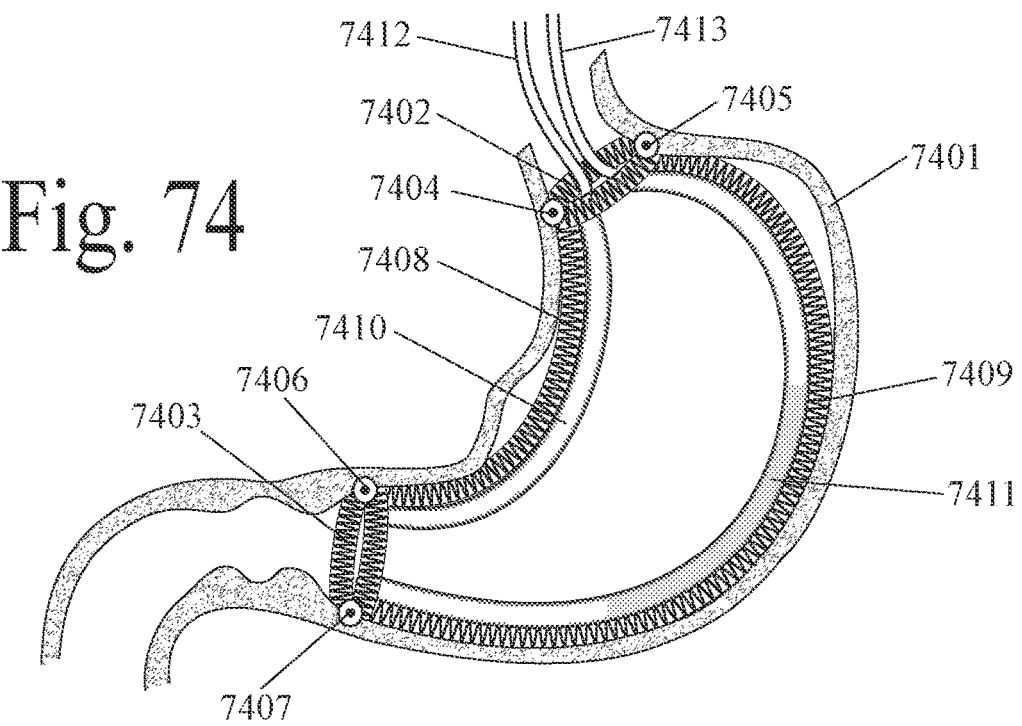
FIG. 74 shows a side view of an intragastric device with tensile rings, longitudinal tensile members, and longitudinal expandable members.
Figure 75:
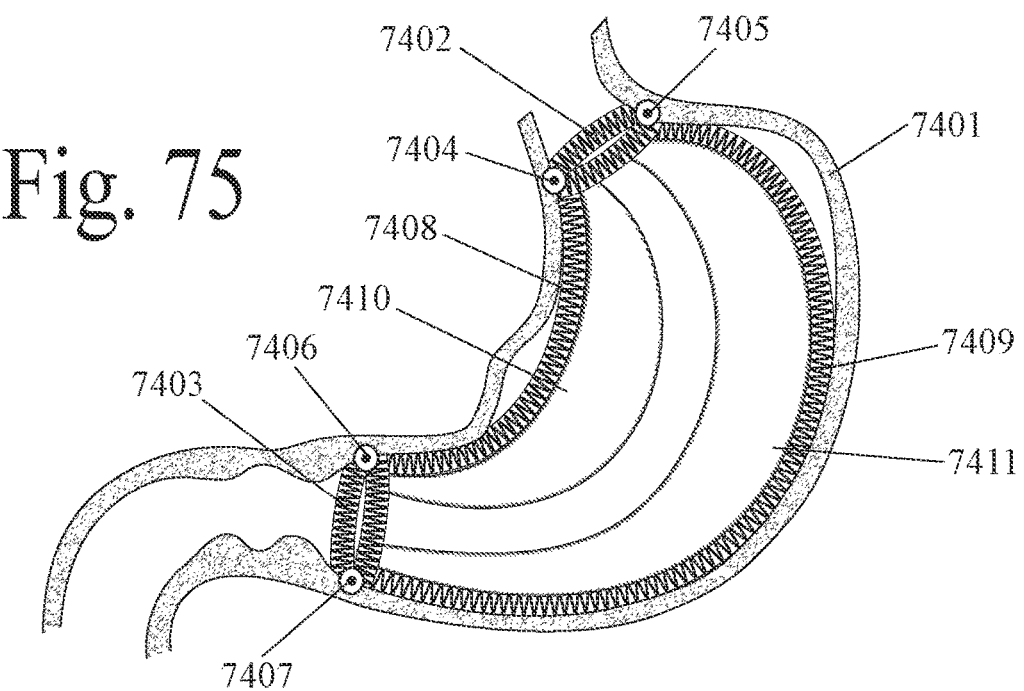
FIG. 75 shows the device in FIG. 74 after the longitudinal expandable members have been expanded.

FIGS. 74 and 75 show another expandable intragastric device for reducing food consumption and/or absorption. This device comprises: (a) an upper tensile ring which is configured to be attached to the inner walls of a stomach within 6" of the gastroesophageal junction; (b) a lower tensile ring which is configured to be attached to the inner walls of a stomach within 6" of the pylorus; (c) a first longitudinal tensile member which is connected to the upper tensile ring and to the lower tensile ring; (d) a first longitudinal expandable member which is connected to the first longitudinal tensile member, wherein this first longitudinal expandable member is expanded within the stomach by being filled with a flowable substance selected from the group consisting of a gas, a liquid, a gel, and a foam; (e) a second longitudinal tensile member which is connected to the upper tensile ring and to the lower tensile ring; and (f) a second longitudinal expandable member which is connected to the second longitudinal tensile member, wherein this second longitudinal expandable member is expanded within the stomach by being filled with a flowable substance selected from the group consisting of a gas, a liquid, a gel, and a foam.

FIG. 74 shows a side view of this device after it has been inserted into a stomach and after the upper and lower tensile rings have been attached to the inner walls of the stomach, but before the first and second expandable members have been expanded. FIG. 75 shows a side view of this same device after it has been inserted into a stomach, after the upper and lower tensile rings have been attached to the inner walls of the stomach, and after the first and second expandable members have been expanded. With respect to specific components, FIGS. 74 and 75 show: stomach wall 7401; upper and lower tensile rings 7402 and 7403; intragastric attachment mechanisms 7404, 7405, 7406, and 7407; first and second longitudinal tensile members 7408 and 7409; first and second longitudinal expandable members 7410 and 7411; and removable flow catheters 7412 and 7413.

In an example, a tensile ring can comprise a sinusoidal wire or filament, a coiled wire or filament, a helical wire or filament, an expandable stent, and/or a spring. In an example, a tensile ring can flexibly resist compression. In an example, a tensile ring can comprise a compression or expansion spring. In an example, the compression-resisting nature of a tensile ring can hold the ring against the inner walls of the stomach. In an example, the compression-resisting nature of a tensile ring can keep the ring open in order to serve as the upper entrance to a food flow lumen formed by the device. In an example, a tensile ring can comprise an inner sinusoidal wire or filament, coiled wire or filament, helical wire or filament, expandable stent, and/or spring which is covered by a fluid-impermeable membrane and/or layer in order to isolate the inner wire, filament, stent, and/or spring from the contents of the stomach. In an example, a device can comprise only an upper tensile ring and a lower tensile ring. In an example, a device can further comprise one or more middle tensile rings between the upper and lower tensile rings.

In an example, an upper or lower tensile ring can be attached to the inner walls of a stomach by one or more intragastric attachment mechanisms. In an example, an intragastric attachment mechanism can be selected from the group consisting of: staple, suture, wire, adhesive, tape, hook, pin, clamp, clip, clasp, prong, screw, bolt, snap, and rivet. In an example, an upper or lower tensile ring can be attached to the inner walls of a stomach by two intragastric attachment mechanisms which look like eyes—but any pastafarianism imagery is strictly unintentional. In an example, an upper or lower tensile ring can be attached to the inner walls of a stomach by three intragastric attachment mechanisms. In an example, an upper or lower tensile ring can be attached to the inner walls of a stomach by four or more intragastric attachment mechanisms.

In an example, a longitudinal tensile member can comprise a sinusoidal wire or filament, a coiled wire or filament, a helical wire or filament, expandable stent, and/or a spring. In an example, a longitudinal tensile member can flexibly resist compression or expansion. In an example, a longitudinal tensile member can comprise a compression or expansion spring. In an example, the compression-resisting nature of a longitudinal tensile member can hold such a member against the inner walls of the stomach. In an example, the compression-resisting nature of a longitudinal tensile member can help to keep an attached longitudinal expandable member against the wall of the stomach and keep a central food lumen open. In an example, a longitudinal tensile member can comprise an inner wire, filament, stent, and/or spring covered by a fluid-impermeable membrane and/or layer to isolate it from the contents of the stomach.

In an example, there can be two longitudinal tensile members. In an example, there can be three longitudinal tensile members. In an example, there can be four longitudinal tensile members. In an example, there can be six or more longitudinal tensile members. In an example, each longitudinal tensile member can be separately connected to an upper tensile ring and to a lower tensile ring. In an example, an upper end of a longitudinal tensile member can be connected to an upper tensile ring and a lower end of a longitudinal tensile member can be connected to a lower tensile ring.

In an example, a first longitudinal tensile member can be configured to face (and/or be closer to) the lesser curve of the stomach. In an example, a first longitudinal tensile member can be configured to generally conform to the wall of the lesser curve of the stomach. In an example, a second longitudinal tensile member can be configured to face (and/or be closer to) the greater curve of the stomach. In an example, a first longitudinal tensile member can be configured to generally conform to the wall of the greater curve of the stomach.

In an example, a longitudinal expandable member can be a balloon. In an example, a longitudinal expandable member can be filled with a liquid, such as saline solution. In an example, a longitudinal expandable member can be filled with a gas, such as air. In an example, a longitudinal expandable member can be attached to a longitudinal tensile member along its entire length. In an example, a longitudinal expandable member can be attached to a longitudinal tensile member along at least half of its length. In an example, a longitudinal expandable member can further comprise a longitudinal lumen or compartment through which a longitudinal tensile member passes. In an example, a longitudinal tensile member can be inside a longitudinal expandable member. In an example, a longitudinal tensile member can be viewed as "being attached to" a longitudinal expandable member because it passes through the expandable member.

In an example, a first longitudinal expandable member can be configured to face (and/or be closer to) the lesser curve of the stomach. In an example, a second longitudinal expandable member can be configured to face (and/or be closer to) the greater curve of the stomach. In an example, first and second longitudinal members can be expanded to substantially the same size cross-sectional areas. In an example, a first longitudinal expandable member can have a first cross-sectional area (when expanded), a second longitudinal expandable member can have a second cross-sectional area (when expanded), and the second cross-sectional area can be greater than the first cross-sectional area. In an example, walls of first and second longitudinal expandable members can comprise (some of) the perimeter of a food flow lumen.

In an example, a first longitudinal expandable member can be expanded by being filled with a flowable substance which flows through a first (removable) catheter and a second longitudinal expandable member can be expanded by being filled with a flowable substance which flows through a second (removable) catheter. In an example, first and second longitudinal expandable members can both be filled with a flowable substance which flows through a single catheter. In an example, a catheter through which a flowable substance flows into a longitudinal expandable member can be removed from the body after the member is expanded.

In an example, a removable catheter through which a flowable substance flows can be re-inserted into the stomach at a later time and re-attached to a longitudinal expandable member in order to add or withdraw a flowable substance from the interior of the longitudinal expandable member. In an example, a catheter can be guided to a selected location on a longitudinal expandable member for re-attachment by electromagnetic attraction between the catheter and the longitudinal expandable member. In an example, a catheter can be guided to a selected location on a longitudinal expandable member for re-attachment by camera-based image guidance. Relevant examples and variations discussed elsewhere in this disclosure can also be applied to this example, but are not all repeated here.

Figure 76:
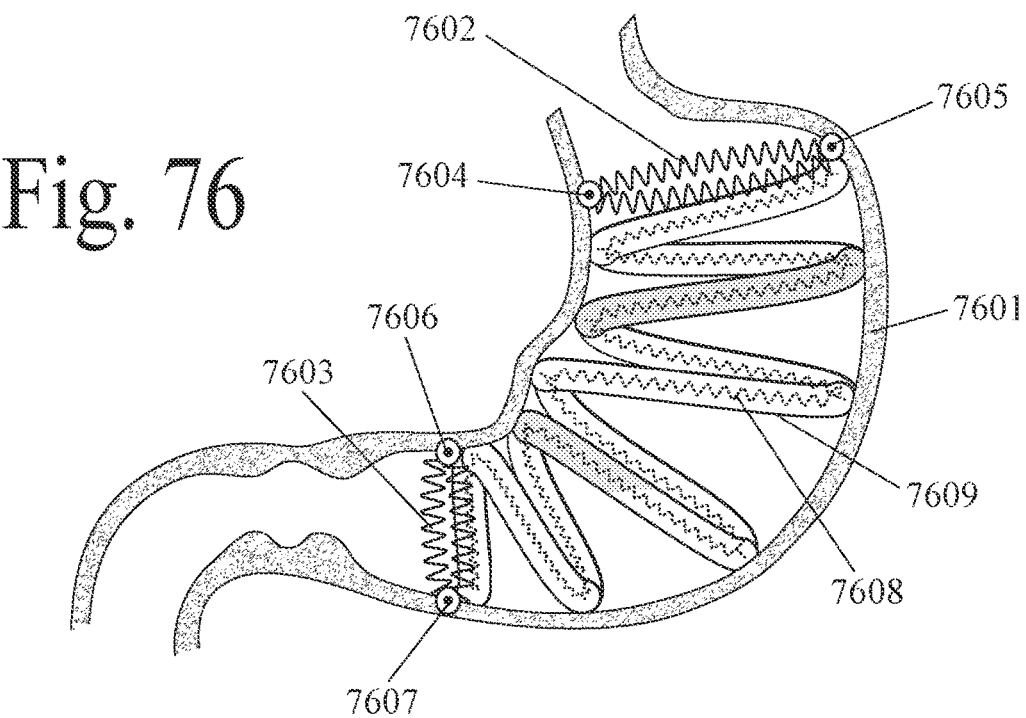
FIG. 76 shows a side view of an intragastric device with tensile rings, a spiral tensile member, and a spiral expandable member.

FIG. 76 shows another expandable intragastric device for reducing food consumption and/or absorption. This device comprises: (a) an upper tensile ring which is configured to be attached to the inner walls of a stomach within 6" of the gastroesophageal junction; (b) a lower tensile ring which is configured to be attached to the inner walls of a stomach within 6" of the pylorus; (c) a spiraling, coiling, and/or looping tensile member with an upper portion which is connected to the upper tensile ring and an lower portion which is connected to the lower tensile ring; and (d) a spiraling, coiling, and/or looping expandable member which is connected to the spiraling, coiling, and/or looping tensile member, wherein this spiraling, coiling, and/or looping expandable member is expanded within the stomach by being filled with a flowable substance selected from the group consisting of a gas, a liquid, a gel, and a foam.

Specifically, FIG. 76 shows: stomach wall 7601; upper and lower tensile rings 7602 and 7603; intragastric attachment mechanisms 7604, 7605, 7606, and 7607; spiraling, coiling, and/or looping tensile member 7608; and spiraling, coiling, and/or looping expandable member 7609. Relevant examples and variations discussed elsewhere in this disclosure can also be applied to this example, but are not all repeated here.

The device shown in FIG. 76 can also be described as comprising: (a) an upper tensile ring which is configured to be attached to the inner walls of a stomach within 6" of the gastroesophageal junction; (b) a lower tensile ring which is configured to be attached to the inner walls of a stomach within 6" of the pylorus; (c) a spiraling, coiling, and/or looping tensile member with an upper portion which is connected to the upper tensile ring and an lower portion which is connected to the lower tensile ring; and (d) a spiraling, coiling, and/or looping expandable member which is expanded within the stomach by being filled with a flowable substance selected from the group consisting of a gas, a liquid, a gel, and a foam, wherein the spiraling, coiling, and/or looping tensile member is inside the spiraling, coiling, and/or looping expandable member.

In an example, a tensile ring can comprise: a sinusoidal, coiled, or helical wire; a stent; and/or a spring. In an example, a tensile ring can flexibly resist compression. In an example, a tensile ring can comprise a compression or expansion spring. In an example, the compression-resisting nature of a tensile ring can hold it against the inner walls of a stomach and keep the ring open for the passage of food. In an example, a tensile ring can be covered by a fluid-impermeable layer to keep out the contents of the stomach. In an example, a tensile ring can be attached to a stomach wall by one or more intragastric attachment mechanisms selected from the group consisting of: staple, suture, wire, adhesive, tape, hook, pin, clamp, clip, clasp, prong, screw, bolt, snap, and rivet.

In an example, a spiraling, coiling, and/or looping tensile member can comprise: a sinusoidal, coiled, or helical wire; and/or a spring. In an example, a spiraling, coiling, and/or looping tensile member can flexibly resist compression and/or expansion. In an example, a spiraling, coiling, and/or looping tensile member can comprise a compression or expansion spring. In an example, the compression-resisting nature of a spiraling, coiling, and/or looping tensile member can hold such a member against the inner wall of a stomach. In an example, a spiraling, coiling, and/or looping tensile member can keep an attached spiraling, coiling, and/or looping expandable member near the wall of the stomach and keep a central lumen open for the passage of food. In an example, a spiraling, coiling, and/or looping tensile member can comprise an inner wire or spring covered by a fluid-impermeable layer.

In an example, a spiraling, coiling, and/or looping tensile member can comprise a longitudinal (e.g. upper to lower, esophageal to pyloric) series of two or more spirals, coils, and/or loops which encircle an arcuate central longitudinal axis of a stomach. In an example, a spiraling, coiling, and/or looping tensile member can comprise a longitudinal (e.g. upper to lower, esophageal to pyloric) series of four or more spirals, coils, and/or loops which encircle an arcuate central longitudinal axis of a stomach. In an example, the spirals, coils, and/or loops of such a tensile member do not overlap. In an example, the spirals, coils, and/or loops of such a tensile member do overlap.

In an example, a spiraling, coiling, and/or looping tensile member can have a central longitudinal axis. In an example, the spirals, coils, and/or loops of a spiraling, coiling, and/or looping tensile member can encircle its central longitudinal axis in a radially-symmetric manner. In an example, the spirals, coils, and/or loops of a spiraling, coiling, and/or looping tensile member can encircle its central longitudinal axis in an asymmetric manner. In an example, an arcuate central longitudinal axis of a spiraling, coiling, and/or looping tensile member can be aligned with the arcuate central longitudinal axis of a stomach. In an example, an arcuate central longitudinal axis of a spiraling, coiling, and/or looping tensile member can be parallel to the arcuate central longitudinal axis of a stomach.

In an example, a spiraling, coiling, and/or looping tensile member can have a first configuration as it is passed through an esophagus into a stomach. In an example, a spiraling, coiling, and/or looping tensile member can have (and/or be shaped into) a second configuration within a stomach. In an example, the first configuration is not a spiraling, coiling, and/or looping shape and the second configuration is a spiraling, coiling, and/or looping shape. In an example, a spiral, coil, and/or loop in a first configuration can have a first radius, a spiral, coil, and/or loop in the second configuration can have a second radius, and the second radius can be greater than the first radius.

In an example, a spiraling, coiling, and/or looping tensile member can be shaped into spirals, coils, or loops within a stomach by being rotated. In an example, a spiraling, coiling, and/or looping member can be shaped into spirals, coils, or loops within a person's stomach by fastening a lower portion of the member to a lower tensile ring and then rotating the rest of the member. In an example, an upper portion of a spiraling, coiling, and/or looping tensile member can be connected to an upper tensile ring after the member has been shaped into a series of spirals, coils, and/or loops.

In an example, a spiraling, coiling, and/or looping expandable member can be a balloon. In an example, a spiraling, coiling, and/or looping expandable member can be filled with a liquid, such as saline solution. In an example, a spiraling, coiling, and/or looping expandable member can be filled with a gas, such as air. In an example, a spiraling, coiling, and/or looping expandable member can be attached to a spiraling, coiling, and/or looping tensile member along its entire length. In an example, a spiraling, coiling, and/or looping expandable member can be attached to a spiraling, coiling, and/or looping tensile member along at least half of its length. In an example, a spiraling, coiling, and/or looping expandable member can further comprise a lumen through which a spiraling, coiling, and/or looping tensile member passes. In an example, a spiraling, coiling, and/or looping tensile member can be inside a spiraling, coiling, and/or looping expandable member.

In an example, a spiraling, coiling, and/or looping expandable member can be expanded by infilling with a flowable substance until the walls of sequential spirals, coils, and/or loops converge in order to create a central food flow lumen. In an example, converging expanded spirals, coils, and/or loops can form a central torus or column within a stomach in order to create a central food flow lumen. In an example, the created central food flow lumen which is created can be aligned with the arcuate central longitudinal axis of the stomach. In an example, the creation of this food flow lumen can simulate some of the effects of gastric sleeve surgery, but can be adjustable and reversible.

In an example, instead of having a single spiraling, coiling, and/or looping expandable member which is connected to a spiraling, coiling, and/or looping tensile member, a variation on this device can comprise a spiraling "string of pearls" design wherein there is a spiraling series of (spherical) expandable members located along the length of a spiraling, coiling, and/or looping tensile member. In an example, a plurality of (spherical) expandable members can be evenly spaced along the length of a spiraling, coiling, and/or looping tensile member. In an example, a series of (spherical) expandable members within a stomach connected by a spiraling, coiling, and/or looping tensile member can comprise at least four (spherical) expandable members. In an example, multiple (spherical) expandable members can be inter-connected by a catheter so that they are concurrently filled by a flowable substance. In an example, these multiple (spherical) expandable members can be separate and separately expanded.

Figure 77:
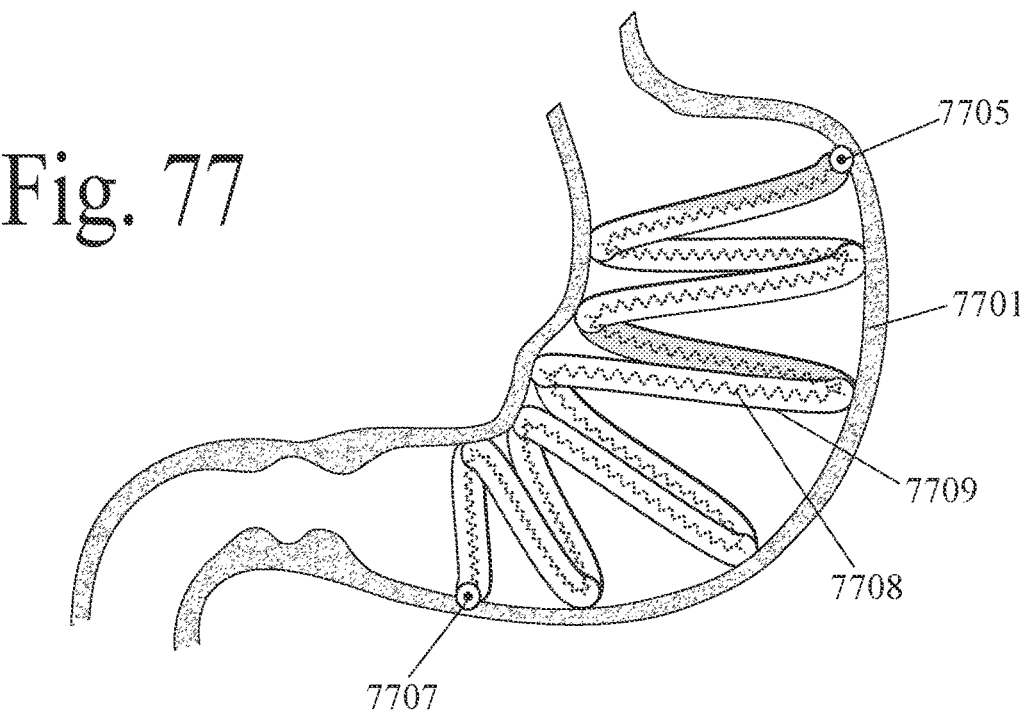
FIG. 77 shows a side view of an intragastric device with a spiral tensile member and a spiral expandable member, but no tensile rings.

FIG. 77 shows an expandable intragastric device for reducing food consumption and/or absorption which is like the one shown in FIG. 76 except that it does not include upper or lower tensile rings. In an example, a spiraling, coiling, and/or looping tensile member can be directly attached to stomach walls. In an example, a spiraling, coiling, and/or looping expandable member can be directly attached to stomach walls. This device comprises: a spiraling, coiling, and/or looping tensile member which is configured to be attached to inner stomach walls; and a spiraling, coiling, and/or looping expandable member which is connected to the spiraling, coiling, and/or looping tensile member, wherein this spiraling, coiling, and/or looping expandable member is expanded within the stomach by being filled with a flowable substance selected from the group consisting of a gas, a liquid, a gel, and a foam. In an example, the spiraling, coiling, and/or looping tensile member can be inside the spiraling, coiling, and/or looping expandable member. Specifically, FIG. 77 shows: stomach wall 7701; intragastric attachment mechanisms 7705 and 7707; spiraling, coiling, and/or looping tensile member 7708; and spiraling, coiling, and/or looping expandable member 7709. Relevant examples and variations discussed elsewhere in this disclosure can also be applied to this example, but are not all repeated here.

Figure 78:
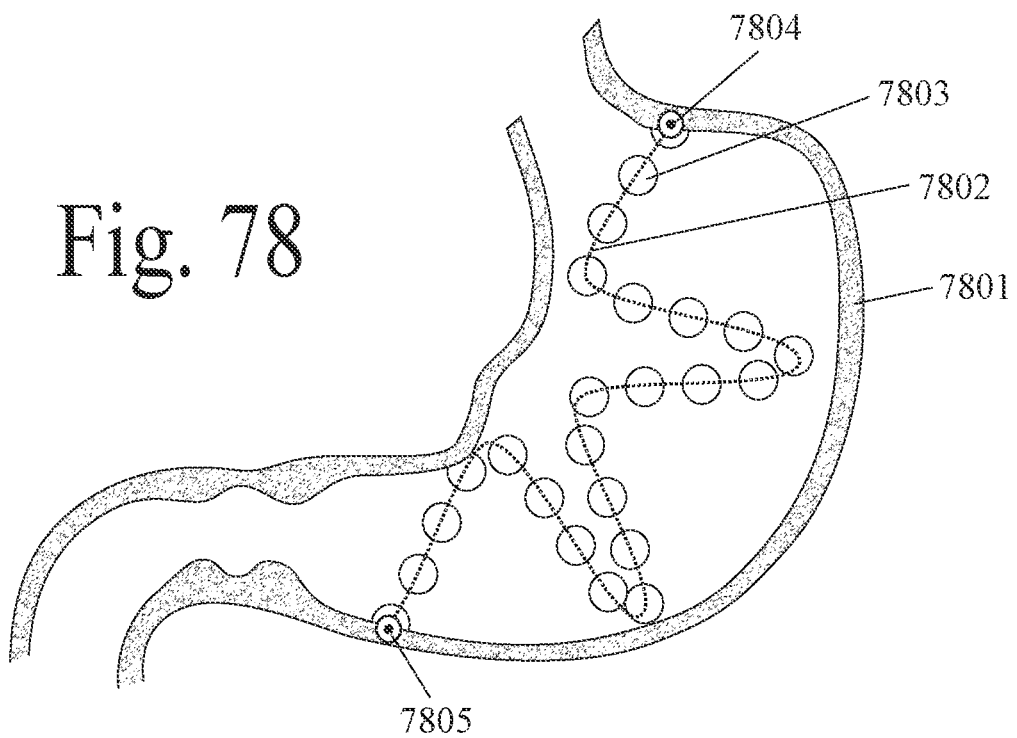
FIG. 78 shows a side view of an intragastric device with a spiral "string of pearls" design comprising a spiral tensile member and a plurality of expandable members.
Figure 79:
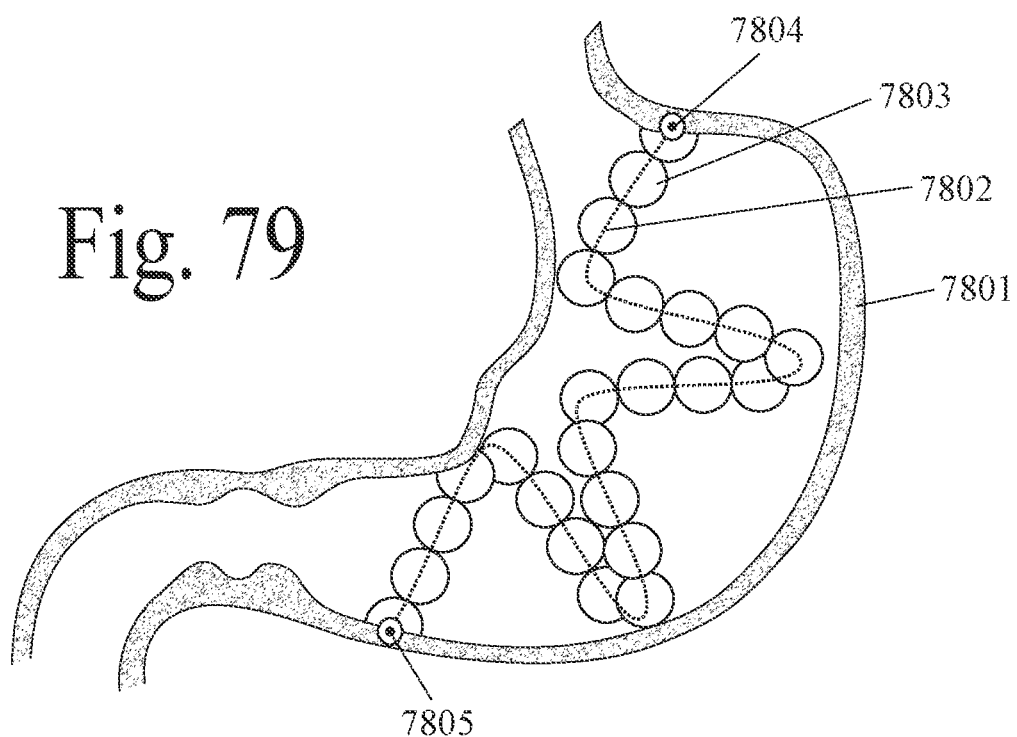
FIG. 79 shows the device in FIG. 78 after the expandable members have been expanded.

FIGS. 78 and 79 show another expandable intragastric device for reducing food consumption and/or absorption. This device has a spiral "string of pearls" design comprising: (a) a spiraling, coiling, and/or looping tensile member which is configured to be attached to the inner wall of a stomach by two or more intragastric attachment mechanisms; and (b) a plurality of four or more (spherical) expandable members which are connected to the spiraling, coiling, and/or looping tensile member, wherein these (spherical) expandable members are expanded within the stomach by being filled with a flowable substance selected from the group consisting of a gas, a liquid, a gel, and a foam.

Specifically, FIGS. 78 and 79 show: stomach wall 7801; spiraling, coiling, and/or looping tensile member 7802; a plurality of four or more (spherical) expandable members, including 7803; and intragastric attachment mechanisms 7804 and 7805. FIG. 78 shows this device before the (spherical) expandable members are expanded within the stomach. FIG. 79 shows this device after the (spherical) expandable members have been expanded within the stomach. In an example, a spiraling, coiling, and/or looping tensile member can be attached to a tensile ring which is, in turn, attached to the stomach wall.

In an example, a spiraling, coiling, and/or looping tensile member can comprise a sinusoidal, coiled, or helical wire, filament, catheter, or tube. In an example, a spiraling, coiling, and/or looping tensile member can comprise a compression or expansion spring. In an example, a spiraling, coiling, and/or looping tensile member can flexibly resist compression and/or expansion. In an example, the compression-resisting nature of a spiraling, coiling, and/or looping tensile member can hold such a member against the inner walls of a stomach. In an example, a spiraling, coiling, and/or looping tensile member can keep attached expandable members near the walls of the stomach and keep a central lumen open for the passage of food. In an example, an intragastric attachment mechanism can be selected from the group consisting of: staple, suture, wire, adhesive, tape, hook, pin, clamp, clip, clasp, prong, screw, bolt, snap, and rivet.

In an example, a spiraling, coiling, and/or looping tensile member can comprise a longitudinal (e.g. upper to lower, esophageal to pyloric) series of two or more spirals, coils, and/or loops which encircle an arcuate central longitudinal axis of a stomach. In an example, a spiraling, coiling, and/or looping tensile member can comprise a longitudinal (e.g. upper to lower, esophageal to pyloric) series of four or more spirals, coils, and/or loops which encircle an arcuate central longitudinal axis of a stomach. In an example, the spirals, coils, and/or loops of such a tensile member do not overlap. In an example, the spirals, coils, and/or loops of such a tensile member do overlap.

In an example, a spiraling, coiling, and/or looping tensile member can have a central longitudinal axis. In an example, the spirals, coils, and/or loops of a spiraling, coiling, and/or looping tensile member can encircle its central longitudinal axis in a radially-symmetric manner. In an example, the spirals, coils, and/or loops of a spiraling, coiling, and/or looping tensile member can encircle its central longitudinal axis in an asymmetric manner. In an example, an arcuate central longitudinal axis of a spiraling, coiling, and/or looping tensile member can be aligned with the arcuate central longitudinal axis of a stomach. In an example, an arcuate central longitudinal axis of a spiraling, coiling, and/or looping tensile member can be parallel to the arcuate central longitudinal axis of a stomach.

In an example, a spiraling, coiling, and/or looping tensile member can have a first configuration as it is passed through an esophagus into a stomach. In an example, a spiraling, coiling, and/or looping tensile member can have (and/or be shaped into) a second configuration within a stomach. In an example, the first configuration is not a spiraling, coiling, and/or looping shape and the second configuration is a spiraling, coiling, and/or looping shape. In an example, a spiral, coil, and/or loop in a first configuration can have a first radius, a spiral, coil, and/or loop in the second configuration can have a second radius, and the second radius can be greater than the first radius.

In an example, a spiraling, coiling, and/or looping tensile member can be shaped into spirals, coils, or loops within a stomach by being rotated. In an example, a spiraling, coiling, and/or looping member can be shaped into spirals, coils, or loops within a person's stomach by fastening a lower portion of the member to a stomach wall and then rotating the rest of the member. In an example, an upper portion of a spiraling, coiling, and/or looping tensile member can be connected to a stomach wall after the member has been shaped into a series of spirals, coils, and/or loops.

In an example, an expandable member can be a balloon. In an example, an expandable member can further comprise a lumen through which a spiraling, coiling, and/or looping tensile member passes. In an example, a spiraling, coiling, and/or looping tensile member can be inside a spiraling, coiling, and/or looping expandable member. In an example, a plurality of expandable members can be expanded by infilling with a flowable substance until their walls converge in order to create a central food flow lumen. In an example, the creation of a food flow lumen can simulate some of the effects of gastric sleeve surgery, but can be adjustable and reversible.

In an example, there can be a series of (spherical) expandable members located along the length of a spiraling, coiling, and/or looping tensile member. In an example, a plurality of (spherical) expandable members can be evenly spaced along the length of a spiraling, coiling, and/or looping tensile member. In an example, individual expandable members can be spherical. In an example, individual expandable members can be oval, elliptical, oblong, egg-shaped, conical, toroidal, or columnar. In an example, expandable members can be inter-connected by a common catheter or tube so that they can be concurrently filled by a flowable substance. In an example, expandable members can be separately expanded by individual catheters or tubes. In an example, there can be one or more micro-pumps which pump a flowable substance between the interiors of one or more of the expandable members in order to change the configuration of the device and/or the size of a central food lumen. Relevant examples and variations discussed elsewhere in this disclosure can also be applied to this example, but are not all repeated here.

Figure 80:
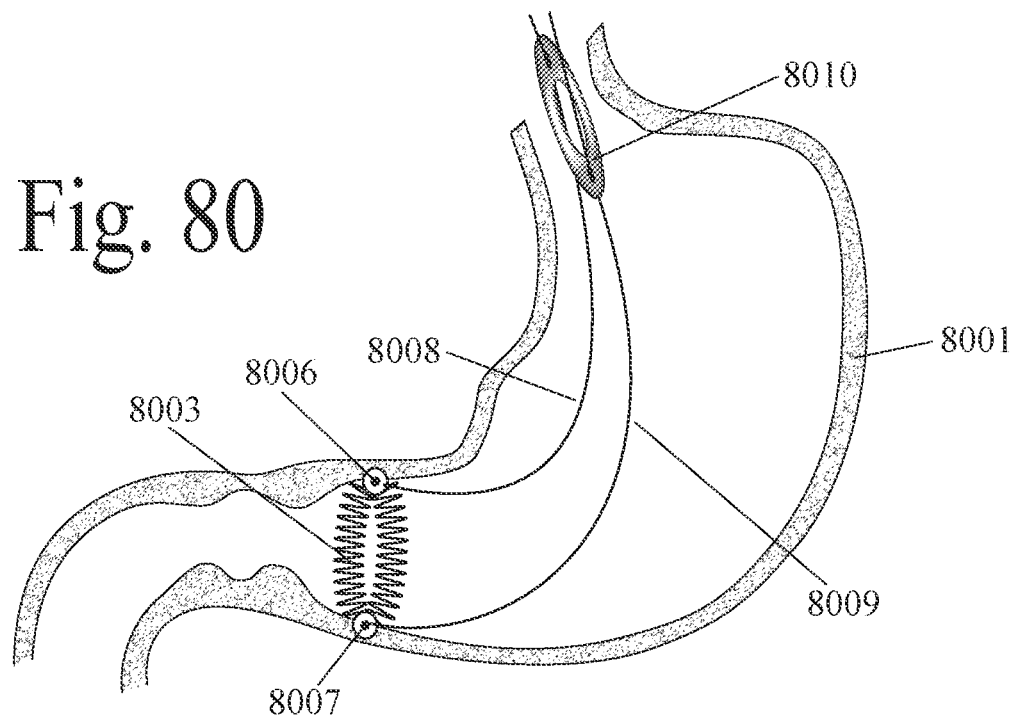
FIG. 80 shows a side view of an intragastric device with a longitudinal sequence of expandable rings connected by longitudinal flexible members.
Figure 81:
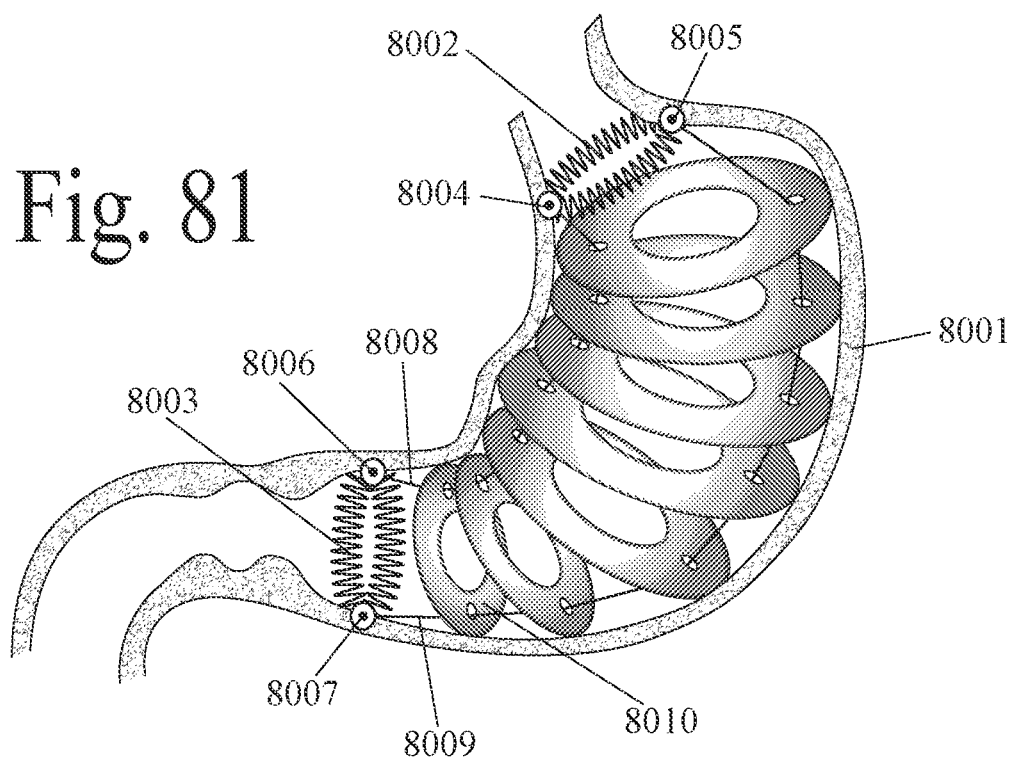
FIG. 81 shows the device in FIG. 80 after the expandable rings have been expanded.

FIGS. 80 and 81 show two sequential views of another expandable intragastric device for reducing food consumption and/or absorption. This device forms a longitudinal sequence of expandable rings (or tori). In an example, these expandable rings can be torus (or doughnut) shaped balloons. These expandable rings are slideably connected to two or more longitudinal flexible members along which the rings are slid into the stomach. The rings (or tori) are stacked and expanded within the stomach so as to create a central food lumen which simulates some of the effects of gastric sleeve surgery. The two or more longitudinal flexible members keep the expandable rings (or tori) in place so that their central food lumen is aligned with the esophageal junction and the pylorus. FIG. 80 shows this device as expandable members are being inserted into the stomach. FIG. 81 shows this device after the expandable rings (or tori) have been inserted into, and expanded within, the stomach.

This device comprises: (a) a lower attachment ring which is configured to be attached to inner stomach walls within 6" of the pylorus; (b) an upper attachment ring which is configured to be attached to inner stomach walls within 6" of the esophageal junction; (c) a first flexible longitudinal member which is configured to be attached to the lower attachment ring and to the upper attachment ring; (d) a second flexible longitudinal member which is configured to be attached to the lower attachment ring and to the upper attachment ring; (e) a first expandable ring (or torus) which is connected to the first and second flexible longitudinal members, wherein this first expandable ring can slide longitudinally along the first and second flexible longitudinal members, and wherein this first expandable ring (or torus) is expanded by being filled with a flowable substance; and (f) a second expandable ring to which is connected to the first and second flexible longitudinal members, wherein this first expandable ring can slide longitudinally along the first and second flexible longitudinal members, and wherein this first expandable ring is expanded by being filled with a flowable substance.

Specifically, FIGS. 80 and 81 show: stomach wall 8001; upper attachment ring 8002; lower attachment ring 8003; intragastric attachment mechanisms 8004, 8005, 8006, and 8007; first and second flexible longitudinal members 8008 and 8009; and a plurality of expandable rings (or tori), including 8010.

In an example, an upper or lower attachment ring can comprise an arcuate, circular, oval, sinusoidal, coiled, helical, and/or toroidal wire or stent. In an example, an upper or lower attachment ring can comprise an arcuate, circular, oval, sinusoidal, coiled, helical, and/or toroidal polymer member. In an example, an upper or lower attachment ring can comprise an arcuate, circular, oval, sinusoidal, coiled, helical, and/or toroidal spring. In an example, an upper or lower attachment ring can resist compression. In an example, an upper or lower attachment ring can be attached to an inner stomach wall by one or more intragastric attachment mechanisms which are selected from the group consisting of: staple, suture, wire, adhesive, tape, hook, pin, clamp, clip, clasp, prong, screw, bolt, snap, and rivet.

In an example, a first or second flexible longitudinal member can be a wire, cord, string, filament, rod, chain, tube, catheter, or spring. In an example, a first longitudinal member can be configured to be a first distance from the greater curve of the stomach, a second flexible longitudinal member can be configured to be second distance from the greater curve of the stomach, and the second distance can be less than the first distance. In an example, a lower end of a flexible longitudinal member can be attached to a lower attachment ring and an upper end of a flexible longitudinal member can be attached to an upper attachment ring. In an example, a device can have two flexible longitudinal members. In an example, a device can have three or more flexible longitudinal members. In an example, a longitudinal member can serve as a conduit for the transmission of a flowable substance into a plurality of expandable rings (or tori) in addition to serving a structural function.

In an example, an expandable ring can be a balloon. In an example, an expandable ring can be torus (or doughnut) shaped with a central lumen through which food can pass. In an example, an expandable ring can have non-central lumens or loops through which flexible longitudinal members pass. In an example, an expandable ring can be filled with a flowable substance selected from the group consisting of: gas, liquid, gel, and foam. In an example, an expandable ring can be made from hydrogel material. In an example, an expandable ring can be made from shape memory material. In an example, a plurality of expandable rings (or tori) can be filled with a flowable substance or otherwise expanded until their walls converge and their central lumens (or holes) combine to form a central food lumen through the stomach. In an example, this central food lumen can simulate some of the effects of gastric sleeve surgery, but be adjustable and reversible.

In an example, expandable rings (or tori) can be interconnected by a common catheter or tube so that they can be concurrently filled by a flowable substance. In an example, expandable rings (or tori) can be separately expanded by individual catheters or tubes. In an example, there can be one or more micro-pumps which pump a flowable substance between the interiors of one or more of the expandable rings (or tori) in order to change the configuration of the device and/or the size of a central food lumen. Relevant examples and variations discussed elsewhere in this disclosure can also be applied to this example, but are not all repeated here.

Figure 82:
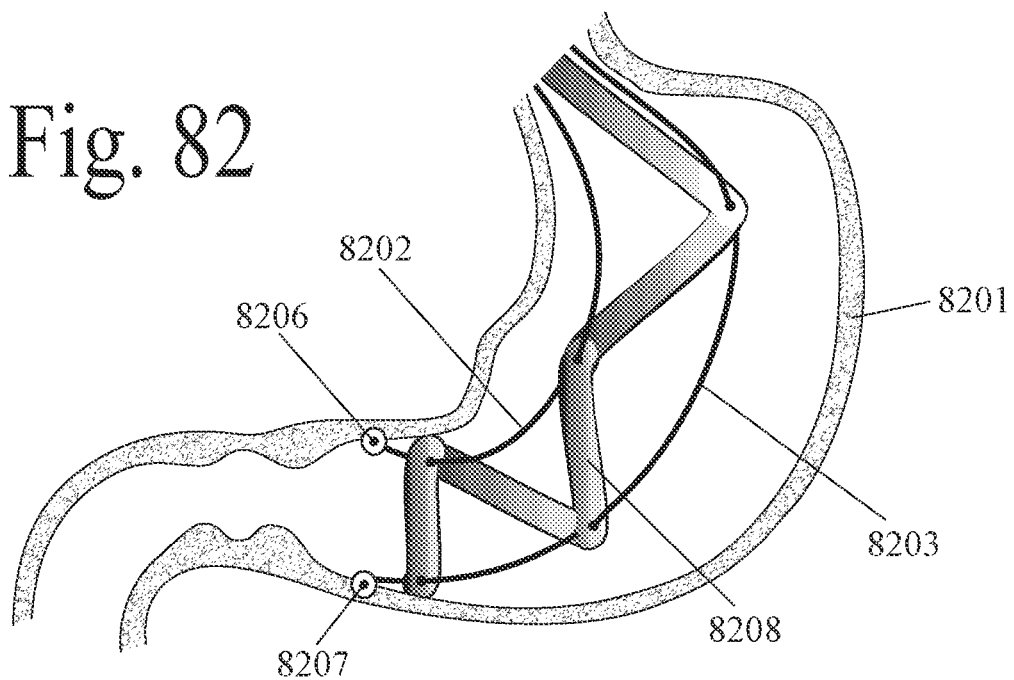
FIG. 82 shows a side view of an intragastric device with an expandable longitudinal spiral connected to longitudinal flexible members.

FIGS. 82 and 83 show two sequential views of another expandable intragastric device for reducing food consumption and/or absorption. This device forms an expandable longitudinal spiral or helix within a stomach. This spiral or helix is held in place by two or more flexible longitudinal members. When expanded, this longitudinal spiral or helix forms a central food lumen which is aligned with the esophageal junction and the pylorus. This central food lumen simulates some of the effects of gastric sleeve surgery, but is adjustable and reversible. FIG. 82 shows this device as the spiral or helix is starting to be inserted into a stomach by sliding down along two longitudinal flexible members whose lower ends are attached to the inner stomach walls. FIG. 83 shows this device after the spiral or helix has been inserted the stomach and the upper ends of the two longitudinal flexible members have also been attached to the inner stomach walls.

This device comprises: (a) a first flexible longitudinal member, wherein this first flexible longitudinal member has an upper portion which is configured to be attached to inner stomach walls within 6" of the esophageal junction and wherein this first flexible longitudinal member has a lower portion which is configured to be attached to inner stomach walls within 6" of the pylorus; (b) a second flexible longitudinal member, wherein this second flexible longitudinal member has an upper portion which is configured to be attached to inner stomach walls within 6" of the esophageal junction and wherein this second flexible longitudinal member has a lower portion which is configured to be attached to inner stomach walls within 6" of the pylorus; and (c) an expandable longitudinal spiral and/or helical member which is inserted into and expanded within the stomach, wherein this expandable longitudinal spiral and/or helical member is connected to the first and second flexible longitudinal members. Specifically, FIGS. 82 and 83 show: stomach wall 8201; flexible longitudinal members 8202 and 8203; intragastric attachment mechanisms 8204, 8205, 8206, and 8207; and expandable longitudinal spiral and/or helical member 8208.

In an example, a flexible longitudinal member can be a wire, cord, string, filament, rod, chain, tube, catheter, or spring. In an example, a first longitudinal member is configured to be a first distance from the greater curve of the stomach, a second flexible longitudinal member is configured to be second distance from the greater curve of the stomach, and the second distance is less than the first distance. In an example, a device can have two flexible longitudinal members. In an example, a device can have three or more flexible longitudinal members. In an example, a longitudinal member can also serve as a conduit for the transmission of a flowable substance. In an example, an intragastric attachment mechanism can be selected from the group consisting of: staple, suture, wire, adhesive, tape, hook, pin, clamp, clip, clasp, prong, screw, bolt, snap, and rivet.

In an example, an expandable longitudinal helical or spiral member can be a balloon. In an example, an expandable longitudinal helical or spiral member can have holes or loops through which flexible longitudinal members pass. In an example, an expandable longitudinal helical or spiral member can be filled with a flowable substance selected from the group consisting of: gas, liquid, gel, and foam. In an example, an expandable longitudinal helical or spiral member can be made from hydrogel material. In an example, an expandable longitudinal helical or spiral member can be made from shape memory material. In an example, an expandable longitudinal helical or spiral member can be filled with a flowable substance or otherwise expanded until its walls converge to form a central food lumen through the stomach. Relevant examples and variations discussed elsewhere in this disclosure can also be applied to this example, but are not all repeated here.

In an example, an implantable expandable intragastric device for reducing food consumption and/or absorption can comprise: (a) a plurality of expandable members, wherein these expandable members are configured to be inserted into and expanded within a person's stomach, wherein these expandable members are expanded by being filled with one or more flowable substances selected from the group consisting of a gas, a liquid, a gel, and a foam, wherein each expandable member has a proximal surface which is configured to be closer to the gastroesophageal junction, wherein each expandable member has a distal surface which is configured to be closer to the pylorus, and wherein each expandable member has a central axis which spans from its proximal surface to its distal surface; and (b) a food flow lumen, wherein this food flow lumen has a proximal opening which is configured to be closer to the gastroesophageal junction, wherein this food flow lumen has a distal opening which is configured to be closer to the pylorus, wherein food flows into the proximal opening and out of the distal opening, wherein this food flow lumen has a central axis which spans from its proximal opening to its distal opening, wherein there is at least one plane of this device which is intersected by the central axis of the food flow lumen and the central axes of the expandable members, wherein the points where the central axes of the expandable members intersect this plane can be geometrically connected to form a polygon, and wherein the point where the central axis of the food flow lumen intersects this plane is located inside this polygon.

In an example, a plurality of expandable members further can comprise at least three and no more than twelve expandable members. In an example, a plurality of expandable members can be separate from each other. In an example, a plurality of expandable members can be interconnected. In an example, a plurality of expandable members can be arranged in a circle. In an example, circle-center-facing portions of walls of the expandable members can collectively form a food flow lumen. In an example, a plurality of expandable members can be distributed around at least 50% of the perimeter of a food flow lumen. In an example, a plurality of expandable members can be distributed around at least 75% of the perimeter of a food flow lumen. In an example, a plurality of expandable members can be distributed around the entire perimeter of a food flow lumen. In an example, a plurality of expandable members can collectively comprise a ring of arcuate columns around a food flow lumen.

An implantable expandable intragastric device for reducing food consumption and/or absorption can comprise: (a) an upper intragastric ring which is configured to be attached to a stomach within the stomach within 6" of the gastroesophageal junction; (b) a lower intragastric ring which is configured to be attached to a stomach within the stomach within 6" of the pylorus; and (c) a plurality of longitudinal expandable members, wherein each longitudinal expandable member has an upper end which is attached to the upper intragastric ring and a lower end which is attached to the lower intragastric ring, and wherein each longitudinal expandable member is expanded within the stomach by being filled with one or more flowable substances selected from the group consisting of a gas, a liquid, a gel, and a foam.

In an example, a upper intragastric ring and/or the lower intragastric ring can be made from a flexibly resilient material which is sufficiently flexible to be deformed during insertion through an esophagus, but which is sufficiently resilient to self-expand into a ring shape after insertion into the stomach. In an example, a upper intragastric ring and/or the lower intragastric ring can be expanded within a stomach by being filled with one or more flowable substances selected from the group consisting of a gas, a liquid, a gel, and a foam. In an example, a longitudinal expandable member can be a balloon. In an example, a longitudinal expandable member can be folded or wrinkled for insertion into a stomach and then unfolded or unwrinkled within a stomach by being filled with a gas, liquid, gel, or foam.

In an example, a virtual lateral cross-section of a plurality of longitudinal expandable members can be made in a plane which is perpendicular to the longitudinal axes of the longitudinal expandable members and wherein connecting the lateral cross-sectional centers of these longitudinal expandable members in this plane forms a triangle, square, pentagon, hexagon, octagon, or decagon. In an example, longitudinal expandable members can be distributed around at least 50% of the perimeter of a food lumen. In an example, longitudinal expandable members can be distributed around at least 75% of the perimeter of a food lumen. In an example, longitudinal expandable members can be distributed around the entire perimeter of a food lumen.

An implantable expandable intragastric device for reducing food consumption and/or absorption can comprise: (a) a flexible mesh or net which is configured to be inserted into a stomach and attached to stomach walls, wherein this flexible mesh or net is attached to stomach walls by two or more intragastric attachment mechanisms, and wherein this flexible mesh or net is configured to span from an upper location within 6" of the gastroesophageal junction to a lower location within 6" of the pylorus; and (b) a longitudinal expandable member which is expanded within the flexible mesh or net within a stomach by being filled with a flowable substance selected from the group consisting of a gas, a liquid, a gel, and a foam.

I claim:

1. An implantable expandable intragastric device for reducing food consumption and/or absorption comprising:
a plurality of longitudinal expandable members, wherein these expandable members are configured to be inserted into and expanded within a person's stomach, wherein these expandable members are expanded by being filled with one or more flowable substances selected from the group consisting of a gas, a liquid, a gel, and a foam, wherein each expandable member has a proximal surface which is configured to be closer to the gastroesophageal junction, wherein each expandable member has a distal surface which is configured to be closer to the pylorus, and wherein each expandable member has a central axis which spans from its proximal surface to its distal surface, wherein the expandable members have lateral cross sections that are shaped like keystones or rounded trapezoids, and wherein first portions of walls of the expandable members that are closer to a food flow lumen are less elastic than second portions of the walls of the expandable members that are farther from the food flow lumen;
the food flow lumen, wherein this food flow lumen has a proximal opening which is configured to be closer to the gastroesophageal junction, wherein this food flow lumen has a distal opening which is configured to be closer to the pylorus, wherein food flows into the proximal opening and out of the distal opening, wherein this food flow lumen has a central axis which spans from its proximal opening to its distal opening, wherein there is at least one plane of this device which is intersected by the central axis of the food flow lumen and the central axes of the expandable members, wherein the points where the central axes of the expandable members intersect this plane can be geometrically connected to form a polygon, wherein the point where the central axis of the food flow lumen intersects this plane is located inside this polygon, and wherein the expandable members are arranged symmetrically around the food flow lumen in a first cross-sectional plane and in a second cross-sectional plane, but are arranged asymmetrically around the food flow lumen in a third cross-sectional plane which is in between the first and second cross-sectional planes.

2. The device in claim 1 wherein the plurality of expandable members are arranged in a circle.

3. The device in claim 2 wherein circle-center-facing portions of walls of the expandable members collectively form a food flow lumen.

4. The device in claim 1 wherein the plurality of expandable members further comprises at least three and no more than twelve expandable members.

5. The device in claim 1 wherein the plurality of expandable members are separate from each other.

6. The device in claim 1 wherein the plurality of expandable members are interconnected.

7. The device in claim 1 wherein the plurality of expandable members are distributed around at least 50% of the perimeter of a food flow lumen.

8. The device in claim 1 wherein the plurality of expandable members are distributed around at least 75% of the perimeter of a food flow lumen.

9. The device in claim 1 wherein the plurality of expandable members are distributed around the entire perimeter of a food flow lumen.

10. The device in claim 1 wherein the plurality of expandable members collectively comprise a ring of arcuate columns around a food flow lumen.

11. An implantable expandable intragastric device for reducing food consumption and/or absorption comprising:

a plurality of longitudinal expandable members, wherein these expandable members are configured to be inserted into and expanded within a person's stomach, wherein these expandable members are expanded by being filled with one or more flowable substances selected from the group consisting of a gas, a liquid, a gel, and a foam, wherein each expandable member has a proximal surface which is configured to be closer to the gastroesophageal junction, wherein each expandable member has a distal surface which is configured to be closer to the pylorus, wherein each expandable member has a central axis which spans from its proximal surface to its distal surface, wherein expandable members configured to be nearer the greater curve of the stomach have larger cross sections and expandable members configured to be nearer the lesser curve of the stomach have smaller cross sections, wherein the expandable members have lateral cross sections that are shaped like keystones or rounded trapezoids, and wherein first portions of walls of the expandable members that are closer to a food flow lumen are less elastic than second portions of the walls of the expandable members that are farther from the food flow lumen; and the food flow lumen, wherein this food flow lumen has a proximal opening which is configured to be closer to the gastroesophageal junction, wherein this food flow lumen has a distal opening which is configured to be closer to the pylorus, wherein food flows into the proximal opening and out of the distal opening, wherein this food flow lumen has a central axis which spans from its proximal opening to its distal opening, wherein there is at least one plane of this device which is intersected by the central axis of the food flow lumen and the central axes of the expandable members, wherein the points where the central axes of the expandable members intersect this plane can be geometrically connected to form a polygon, and wherein the point where the central axis of the food flow lumen intersects this plane is located inside this polygon.

* * * * *